(12) United States Patent
Chen et al.

(10) Patent No.: US 10,377,755 B2
(45) Date of Patent: Aug. 13, 2019

(54) BCL-2 INHIBITORS

(71) Applicant: Newave Pharmaceutical Inc., Pleasanton, CA (US)

(72) Inventors: Yi Chen, Pleasanton, CA (US); Yan Lou, Pleasanton, CA (US)

(73) Assignee: Newave Pharmaceutical Inc., Pleasanton, CA (US)

(*) Notice: Subject to any disclaimer, the term of this patent is extended or adjusted under 35 U.S.C. 154(b) by 0 days.

(21) Appl. No.: 16/045,736

(22) Filed: Jul. 26, 2018

(65) Prior Publication Data

US 2019/0040062 A1 Feb. 7, 2019

Related U.S. Application Data

(63) Continuation of application No. PCT/US2017/015281, filed on Jan. 27, 2017.

(60) Provisional application No. 62/289,209, filed on Jan. 30, 2016.

(51) Int. Cl.
| | |
|---|---|
| *C07D 471/14* | (2006.01) |
| *A61P 35/02* | (2006.01) |
| *A61P 35/00* | (2006.01) |

(52) U.S. Cl.
CPC .......... *C07D 471/14* (2013.01); *A61P 35/00* (2018.01); *A61P 35/02* (2018.01)

(58) Field of Classification Search
CPC ......... C07D 471/14; A61P 35/02; A61P 35/00
See application file for complete search history.

(56) References Cited

U.S. PATENT DOCUMENTS

2010/0305122 A1  12/2010  Bruncko et al.

FOREIGN PATENT DOCUMENTS

WO    2009/036035 A1   3/2009

OTHER PUBLICATIONS

PubChem, SCHEMBL17897155, Compound Summary for CID 24729558. 14 pages. Retrieved online at: https://pubchem.ncbi.nlm.nih.gov/compound/24729558. Mar. 4, 2017.
Souers et al., ABT-199, a potent and selective BCL-2 inhibitor, achieves antitumor activity while sparing platelets. Nat Med. Feb. 2013;19(2):202-8.

*Primary Examiner* — Rebecca L Anderson
(74) *Attorney, Agent, or Firm* — McCarter & English, LLP; Yu Lu; Wei Song

(57) ABSTRACT

The disclosure includes compounds of Formula (I)

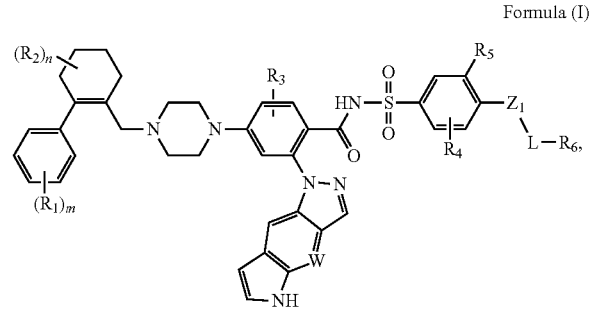

Formula (I)

wherein W, $R_1$, $R_2$, $R_3$, $R_4$, $R_5$, $R_6$, m, n, L, and $Z_1$, are defined herein. Also disclosed is a method for treating a neoplastic disease and autoimmune disease with these compounds.

13 Claims, No Drawings
Specification includes a Sequence Listing.

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Leu Trp Ala Ala Gln Arg Tyr Gly Arg Glu Leu Arg Arg Met Ser
1               5                   10                  15

Asp Lys Phe Val Asp
            20

BCL-2 INHIBITORS

CROSS-REFERENCE TO RELATED APPLICATIONS

This application is a continuation of International Patent Application No. PCT/US2017/015281, filed on Jan. 27, 2017, which claims the benefit of the filing date of U.S. Provisional Application No. 62/289,209, filed on Jan. 30, 2016. The entire contents of each of the aforementioned applications are incorporated herein by reference.

SEQUENCE LISTING

The instant application contains a Sequence Listing which has been filed electronically in ASCII format and is hereby incorporated by reference in its entirety. Said ASCII copy, created on Oct. 25, 2018, is named 125569-00502_SL.txt and is 632 bytes in size.

BACKGROUND OF THE INVENTION

Apoptosis, or programmed cell death, is a conserved and regulated process that is the primary mechanism for the removal of aged, damaged and unnecessary cells. The ability to block apoptotic signaling is a key hallmark of cancer and is thus important for oncogenesis, tumor maintenance and chemoresistance [Hanahan, D. & Weinberg, R. A. The hallmarks of cancer. Cell 100, 57-70 (2000).]. Dynamic binding interactions between prodeath (for example, BCL-2-associated X protein (BAX), BCL-2 antagonist/killer 1 (BAK), BCL-2-associated agonist of cell death (BAD), BCL-2-like 11 (BIM), NOXA and BCL-2 binding component 3 (PUMA)) and prosurvival (BCL-2, BCL-XL, BCL-2-like 2 (BCL-W), myeloid cell leukemia sequence 1 (MCL-1) and BCL-2-related protein A1 (BFL-1)) proteins in the BCL-2 family control commitment to programmed cell death. Altering the balance among these opposing factions provides one means by which cancer cells undermine normal apoptosis and gain a survival advantage [Youle, R. J. & Strasser, A. The BCL-2 protein family: opposing activities that mediate cell death. Nat. Rev. Mol. Cell Biol. 9, 47-59 (2008)].

BCL-2, the first identified apoptotic regulator, was originally cloned from the breakpoint of a t(14;18) translocation present in human B cell lymphomas[Tsujimoto, Y., et al. Science 228, 1440-1443 (1985); Cleary, M. L., et al Cell 47, 19-28 (1986); Boise, L. H. et al. Cell 74, 597-608 (1993)]. This protein has since been shown to have a dominant role in the survival of multiple lymphoid malignancies [Vaux, D. L., et al pre-B cells. Nature 335, 440-442 (1988)]. Overexpression of Bcl-2 proteins correlates with resistance to chemotherapy, clinical outcome, disease progression, overall prognosis or a combination thereof in various cancers and disorders of the immune system. Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT/US2004/36770, published as WO 2005/049593, and PCT/US/2004/37911, published as WO 2005/024636. Involvement of Bcl-2 proteins in immune and autoimmune diseases is described in Current Allergy and Asthma Reports 2003, 3, 378-384; British Journal of Hematology 2000, 110(3), 584-90; Blood 2000, 95(4), 1283-92; and New England Journal of Medicine 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

In the last decade, several Bcl-2 inhibitors such as ABT-737, ABT-263, and ABT-199 as shown below have been identified and entered human clinical trials for cancers treatment.

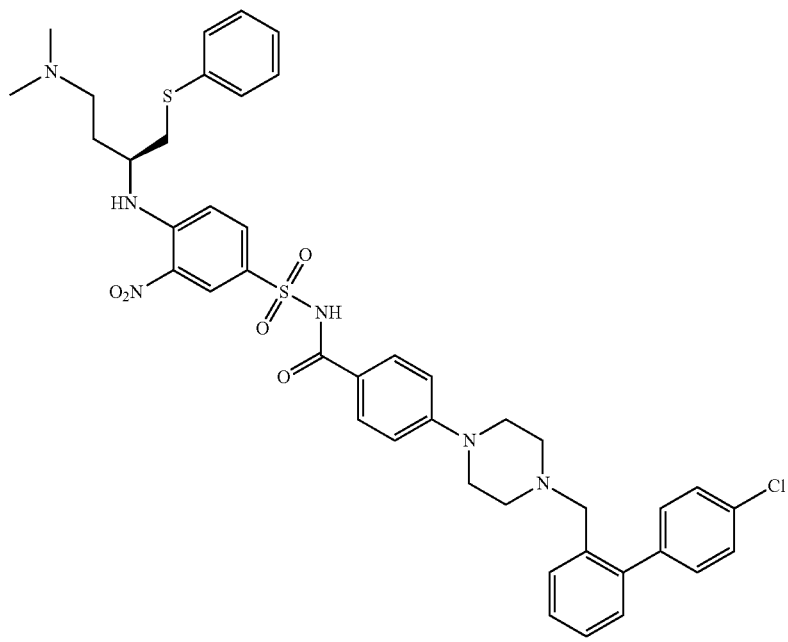

ABT-737

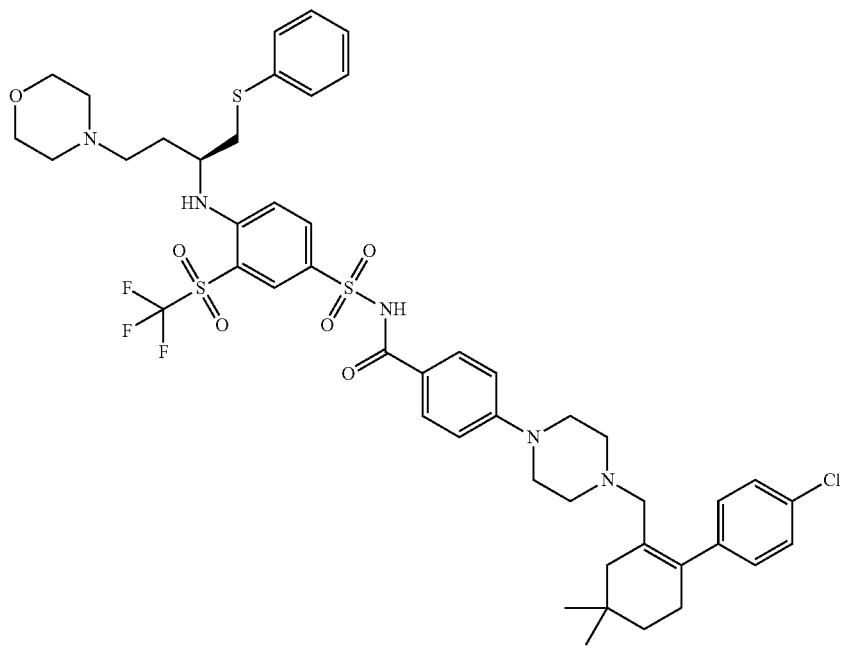

ABT-263

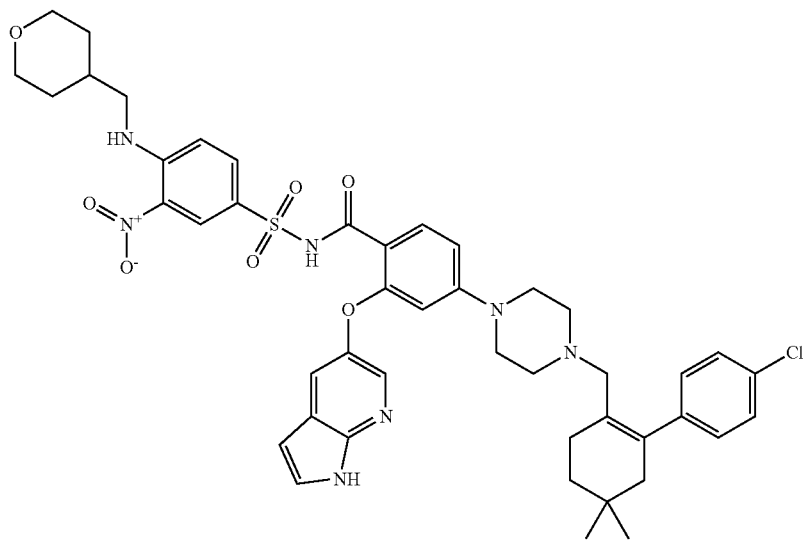

ABT-199

ABT-737 is discovered by nuclear magnetic resonance (NMR)-based screening, parallel synthesis and structure based fragment drug design [Tilman Oltersdorf, et al, Nature, Vol 435, 2005, p 677]. ABT-737 a small-molecule inhibitor of the anti-apoptotic proteins Bcl-2, Bcl-XL and Bcl-w, with an affinity two to three orders of magnitude more potent than previously reported compounds. Mechanistic studies reveal that ABT-737 does not directly initiate the apoptotic process, but enhances the effects of death signals, displaying synergistic cytotoxicity with chemotherapeutics and radiation. ABT-737 exhibits single-agent-mechanism-based killing of cells from lymphoma and small-cell lung carcinoma lines, as well as primary patient-derived cells, and in animal models, ABT-737 improves survival, causes regression of established tumors, and produces cures in a high percentage of the mice. Unfortunately, ABT-737 is not orally bioavailable and its low aqueous solubility makes formulation for intravenous delivery extremely difficult.

After extensive MedChem effort, an orally bioavailable Bcl-2 inhibitor ABT-263 (Navitoclax) has been developed [Cheol-Min Park, et al J. Med. Chem. 2008, 51, 6902-6915]. ABT-263 is a potent inhibitor of Bcl-xL, Bcl-2 and Bcl-w with Ki of ≤0.5 nM, ≤1 nM and ≤1 nM. ABT-263 has a $IC_{50}$ of 110 nM against SCLC H146 cell line, When ABT-263 is administered at 100 mg/kg/day in the H345 xenograft model, significant antitumor efficacy is observed with 80% TGI and 20% of treated tumors indicating at least a 50% reduction in tumor volume. Oral administration of ABT-263 alone causes complete tumor regressions in xenograft models of small-cell lung cancer and acute lymphoblastic leukemia [Tse C, et al. Cancer Res. 2008, 68(9), 3421-3428]. Unfortunately, in the clinical trial, the inhibition of BCL-XL by ABT-263 (navitoclax) induces a rapid, concentration-dependent decrease in the number of circulating platelets. This mechanism-based thrombocytopenia is the dose-limiting toxicity of single-agent navitoclax treatment in patients and limits the ability to drive drug concentrations into a highly efficacious range.

Thus, a BCL-2 selective (BCL-XL sparing) inhibitor would culminate in substantially reduced thrombocytopenia while maintaining efficacy in lymphoid malignancies. The resulting increase in the therapeutic window should allow for greater BCL-2 suppression and clinical efficacy in BCL-2-dependent tumor types, After extensive MedChem, ABT-199 (GDC-0199) has been successfully developed[Andrew J Souers, et al, Nature Medicine, Volume 19, 22, p 202, 2013]. ABT-199 is a Bcl-2-selective inhibitor with Ki of <0.01 nM, >4800-fold more selective versus Bcl-xL and Bcl-w, and no activity to Mcl-1. ABT-199 potently inhibits RS4;11 cells with $EC_{50}$ of 8 nM. In addition, ABT-199 induces a rapid apoptosis in RS4;11 cells with cytochrome c release, caspase activation, and the accumulation of sub-G0/G1 DNA. Quantitative immunoblotting reveals that sensitivity to ABT-199 correlated strongly with the expression of Bcl-2, including NHL, DLBCL, MCL, AML and ALL cell lines. ABT-199 also induces apoptosis in CLL with an average $EC_{50}$ of 3.0 nM. A single dose of 100 mg/kg of ABT-199 causes a maximal tumor growth inhibition of 95% and tumor growth delay of 152% in RS4;11 xenografts. ABT-199 also inhibits xenograft growth (DoHH2, Granta-519) as a single agent or in combination with Bendamustine and other agents. Human Phase I and II data showed that ABT-199 is highly efficacious for CLL, however, ABT-199 causes lethal tumour lysis syndrome in which the debris of dying cancer cells overwhelms the kidney and other organs.

Although the Bcl-2 inhibitors, particularly the Bcl-2 selective inhibitor ABT-199 have made a significant contribution to the art, there is a continuing search in this field of art for improved pharmaceuticals.

SUMMARY OF THE INVENTION

In a first embodiment, this invention provides compounds of the Formula (I) or an N-oxide thereof, or a pharmaceutically acceptable salt, solvate, polymorph, tautomer, stereoisomer, an isotopic form, or a prodrug of said compound of Formula (I) or N-oxide thereof:

wherein $Z_1$ is absent, $(CH_2)_p$, N(H), O, S, C(O), $S(O)_2$, OC(O), C(O)O, $OS(O)_2$, $S(O)_2O$, C(O)S, SC(O), C(O)C(O), C(O)N(H), N(H)C(O), $S(O)_2N(H)$, $N(H)S(O)_2$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

W is CH or N, and the tricyclic

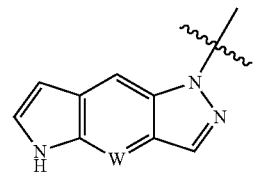

is optionally substituted with one or more $R_7$;

each of $R_1$, $R_2$, $R_3$, $R_4$, $R_5$, $R_6$, and $R_7$, independently, is H, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $P(O)R_bR_c$, $C(O)N(R_b)R_c$, $N(R_b)C(O)R_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

optionally, two of $R_2$ group, taken together with the atom to which they are attached, may optionally form a cycloalkyl or heterocycloalkyl optionally substituted with one or more $R_d$;

$R_a$, $R_b$, $R_c$ and $R_d$, independently, is H, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of $R_1$, $R_2$, independently, is H or alkyl; or two of $R_2$ group, taken together with the atom to which they are attached, may optionally form a cycloalkyl;

L is absent, alkylene, alkenylene, alkynylene, cycloalkylene, cycloalkenylene, heterocycloalkylene, heterocycloalkenylene, wherein said alkylene, alkenylene, alkynylene, cycloalkylene, cycloalkenylene, heterocycloalkylene, or heterocycloalkenylene is optionally substituted with one or more $R_d$; and each of m, p, and q, independently, is 0, 1, 2, 3, or 4.

Formula (I)

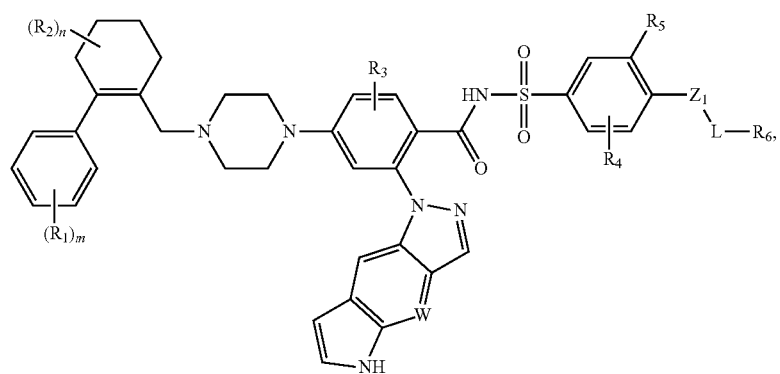

In a second embodiment, the invention provides the compounds according to the previous embodiment, wherein the compound is represented by Formula (II):

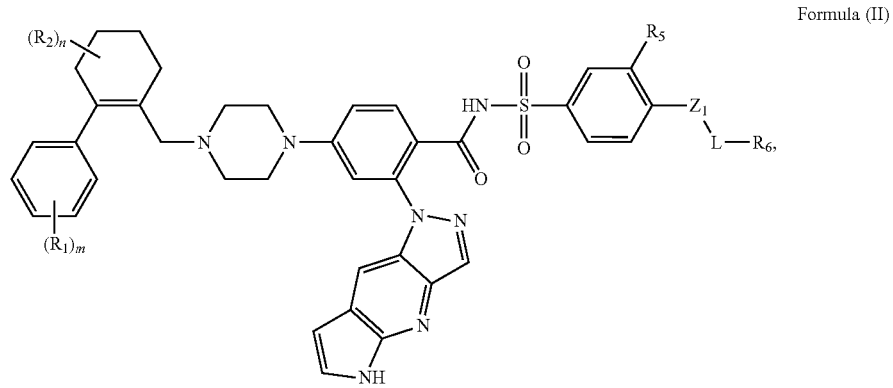

Formula (II)

wherein the tricyclic

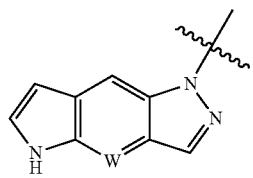

is unsubstituted, wherein the reminder of the variables are as defined in the first embodiment.

In a third embodiment, the invention provides the compounds according to the previous embodiments, wherein the compound is represented by Formula (III):

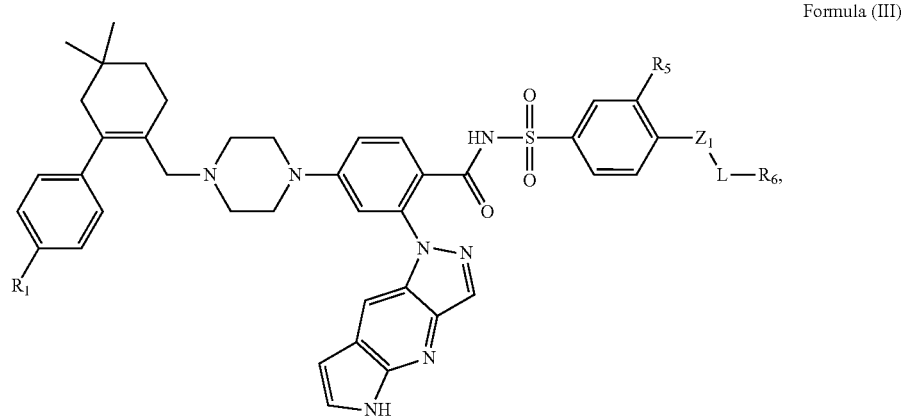

Formula (III)

wherein the reminder of the variables are as defined in the first embodiment.

In a fourth embodiment, the invention provides the compounds according to the previous embodiments, wherein $R_1$ is halo (e.g., Cl), wherein the reminder of the variables are as defined in the first, second or third embodiment.

In a fifth embodiment, the invention provides the compounds according to the previous embodiments, wherein $R_5$ independently, is nitro, halo, or $SO_2R_a$, wherein the reminder of the variables are as defined in the first, second, third or fourth embodiment.

In a sixth embodiment, the invention provides the compounds according to the previous embodiments, wherein $Z_1$ is absent, NH, O, or S, wherein the reminder of the variables are as defined in the first, second, third, fourth, or fifth embodiment. In a seventh embodiment, the invention provides the compounds according to the previous embodiments, wherein L is absent or $C_{1-3}$alkylene, wherein the reminder of the variables are as defined in the first, second, third, fourth, fifth, or sixth embodiment.

In an eighth embodiment, the invention provides the compounds according to the previous embodiments, wherein $R_6$ is H, 4-6 membered cycloalkyl or 4-6 membered heterocyclyl, wherein the 4-6 membered cycloalkyl or 4-6 membered heterocyclyl is optionally substituted with one or more substituents selected from the group consisting of halo, $C_{1-4}$alkyl, CN, —OH, $C_{1-4}$alkoxy, —S(O)$_2$CH$_3$, —COCH$_3$, 3-6 membered cycloalkyl, and 3-6 membered heterocyclyl, wherein the reminder of the variables are as defined in the first, second, third, fourth, fifth, sixth, or seventh embodiment Compounds of the invention may contain one or more asymmetric carbon atoms. Accordingly, the compounds may exist as diastereomers, enantiomers, or mixtures thereof.

Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, therapeutic uses thereof, and use of the compounds for the manufacture of a medicament for treating the disease/disorder.

This invention also relates to a method of treating a neoplastic disease or an autoimmune disease by administering to a subject in need thereof an effective amount of one or more of the compounds, modifications, and/or salts, and compositions thereof described above. The neoplastic disease or the autoimmune disease can be ameliorated by inhibition of bcl-2. In one embodiment, the neoplastic disease is leukemia, lymphoma, or multiple myeloma.

Also provided herein is the use of one or more of the disclosed compounds, or a pharmaceutically acceptable salt thereof, or the pharmaceutical composition thereof, for the preparation of a medicament for the treatment of a neoplastic disease or an autoimmune disease.

In another embodiment provided herein, the disclosed compounds, or a pharmaceutically acceptable salt thereof, or the pharmaceutical composition thereof are for use in treating a neoplastic disease or an autoimmune disease.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

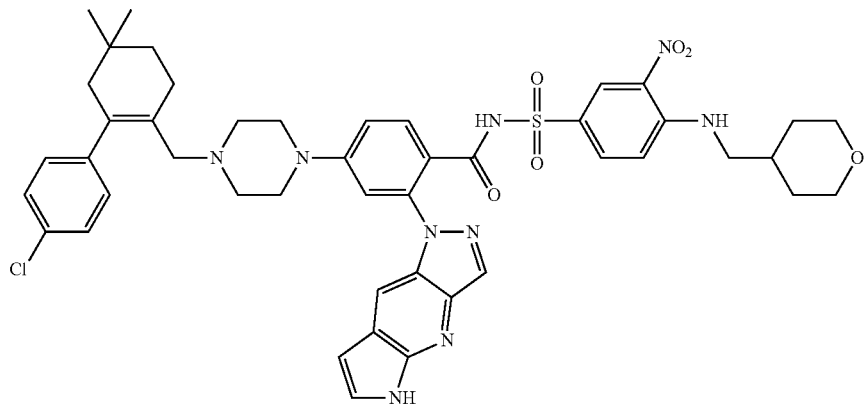

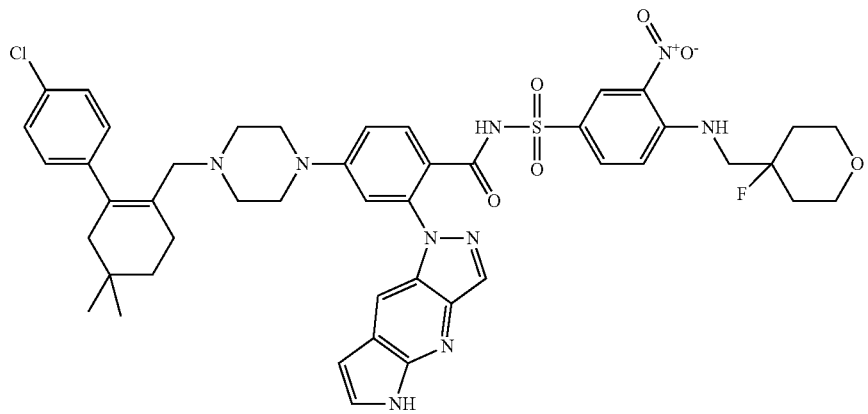

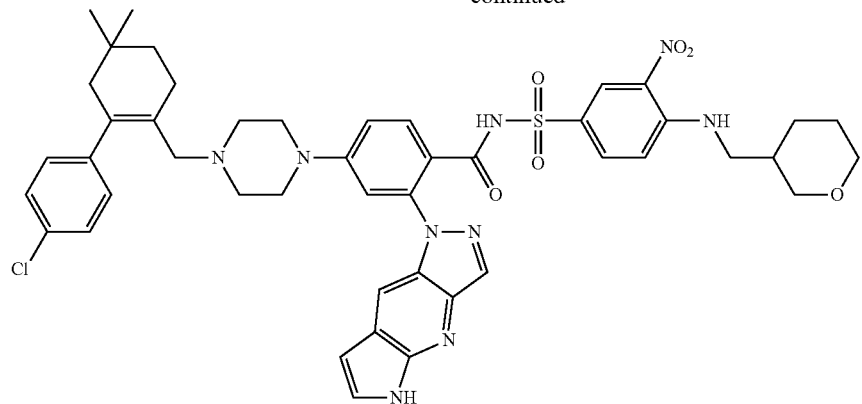
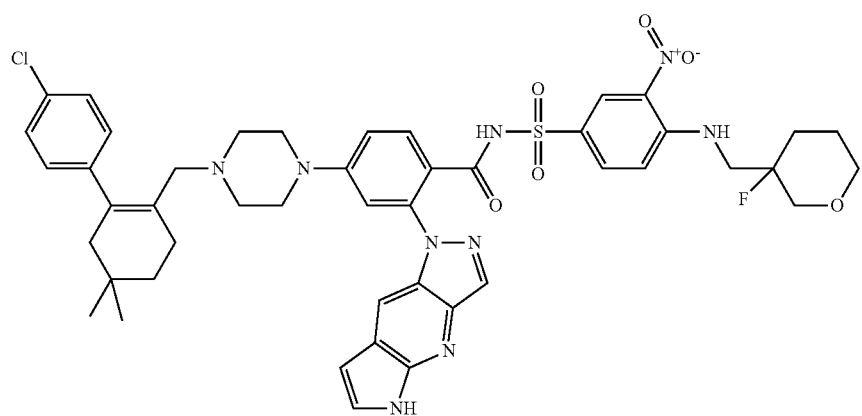
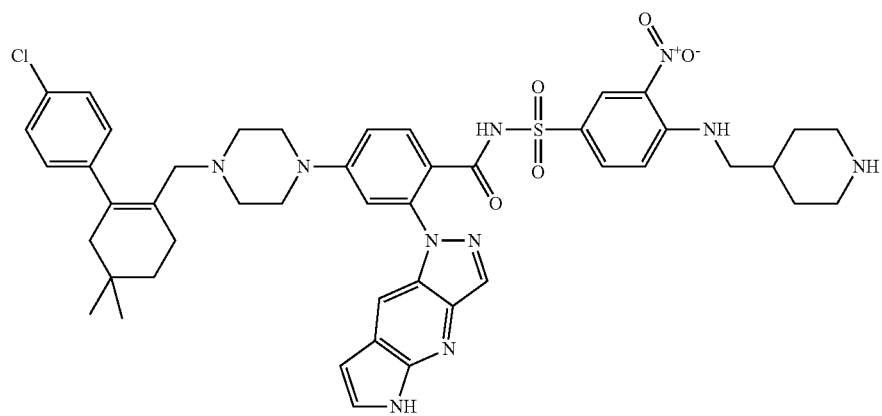
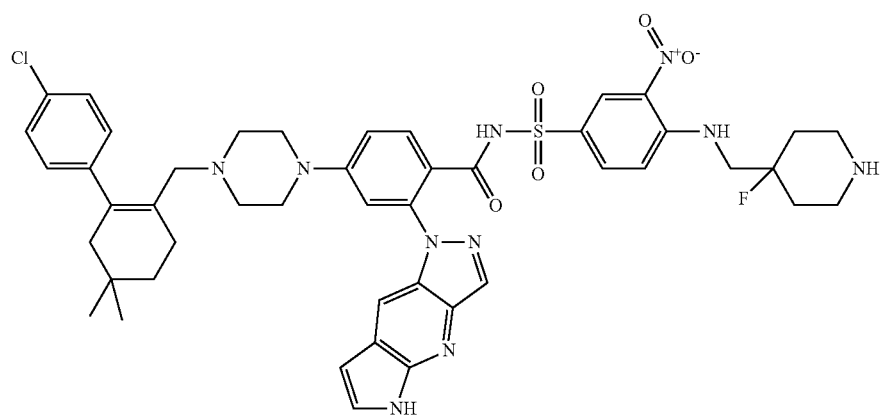

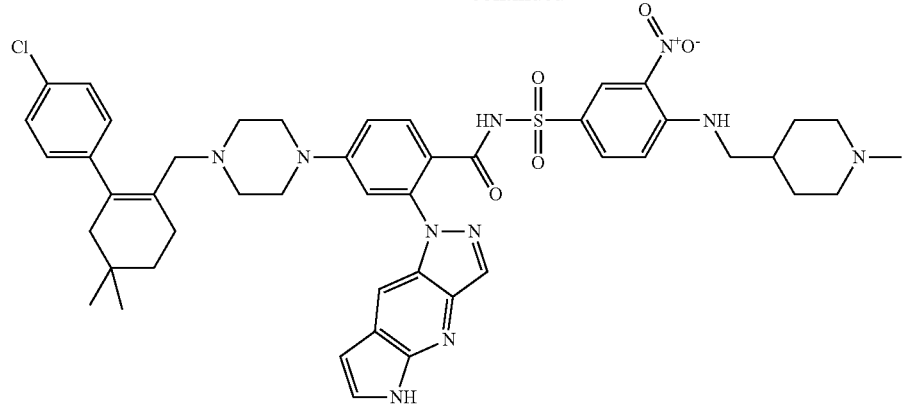
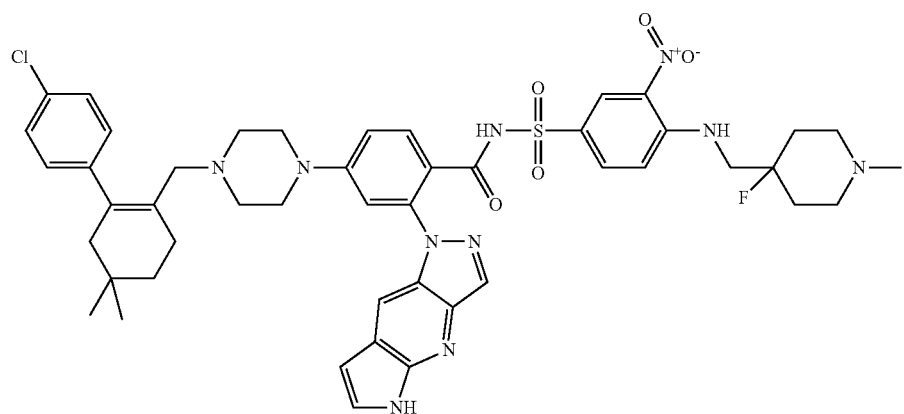
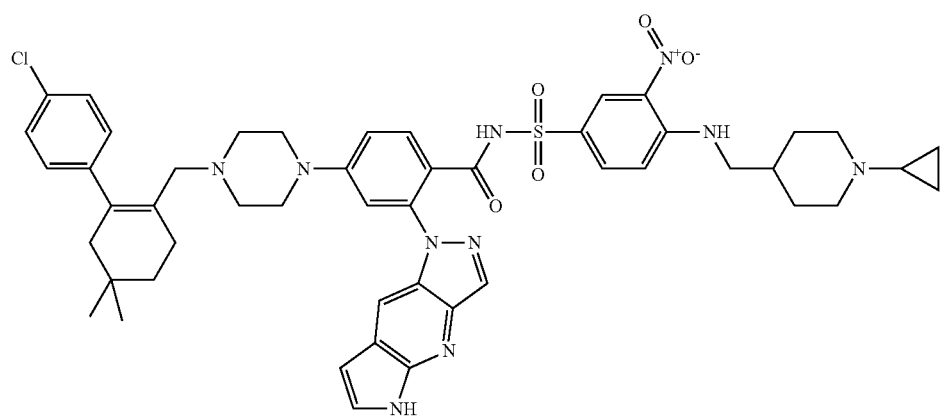
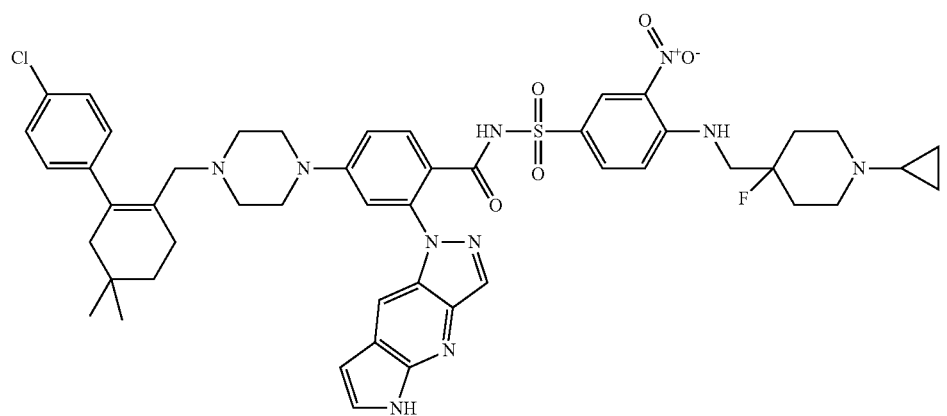

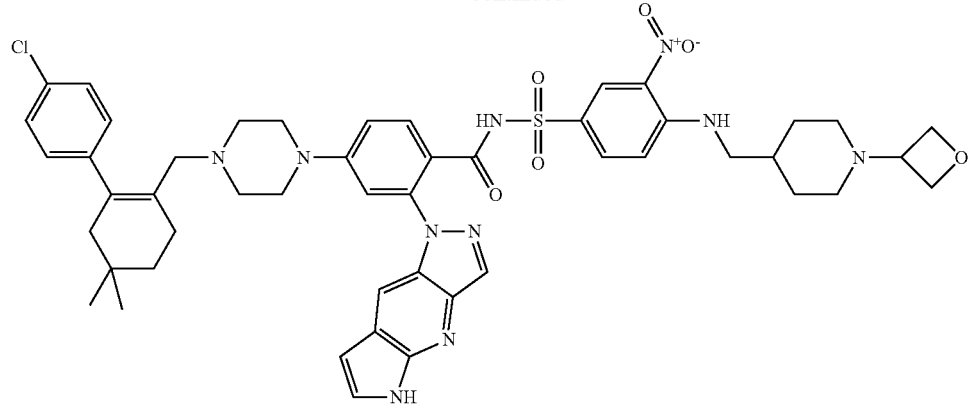
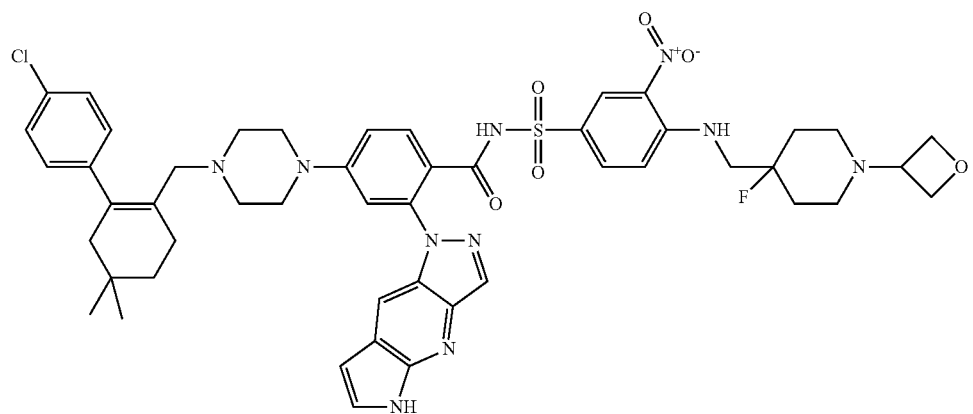
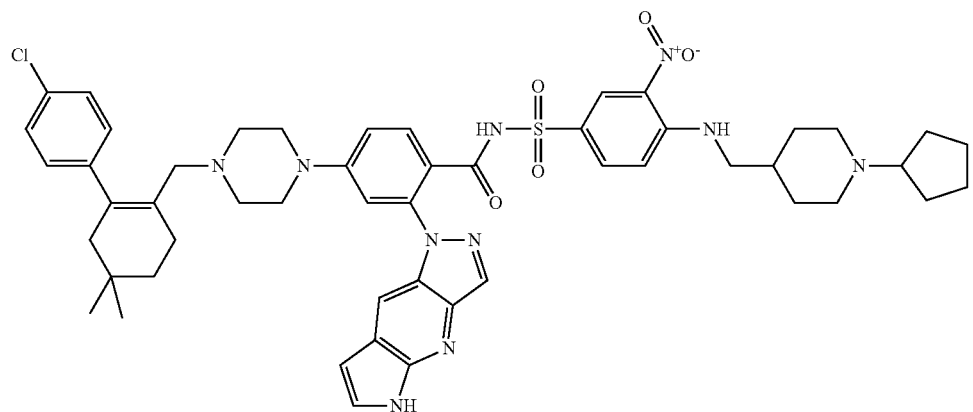
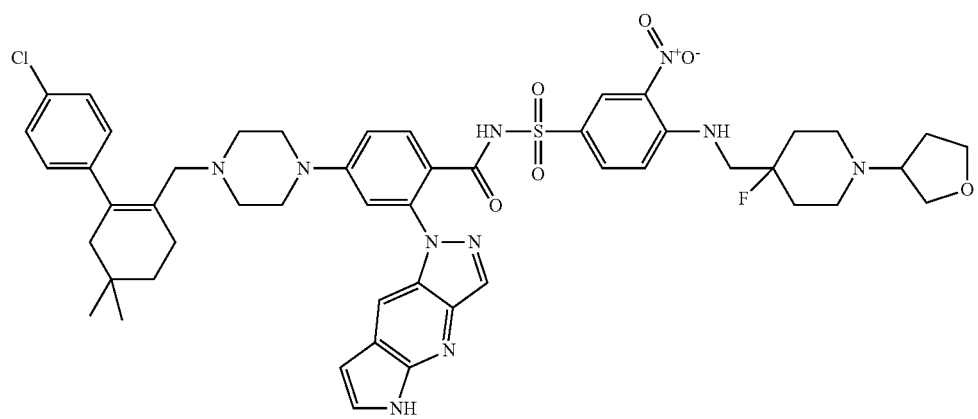

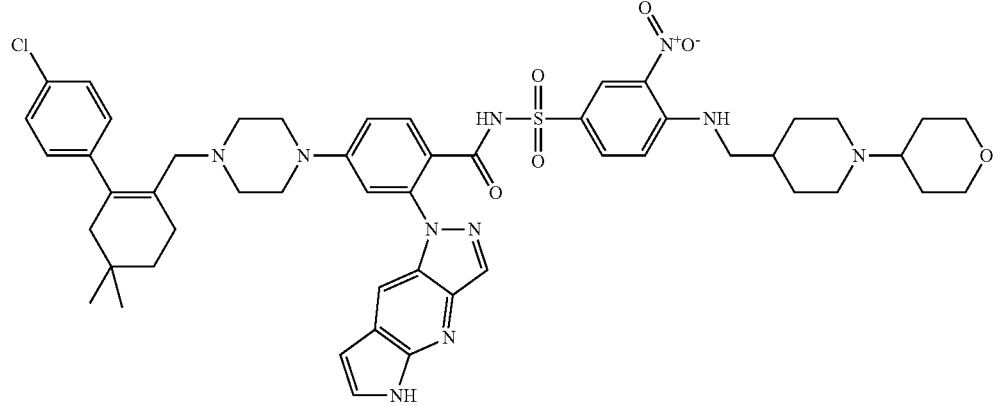
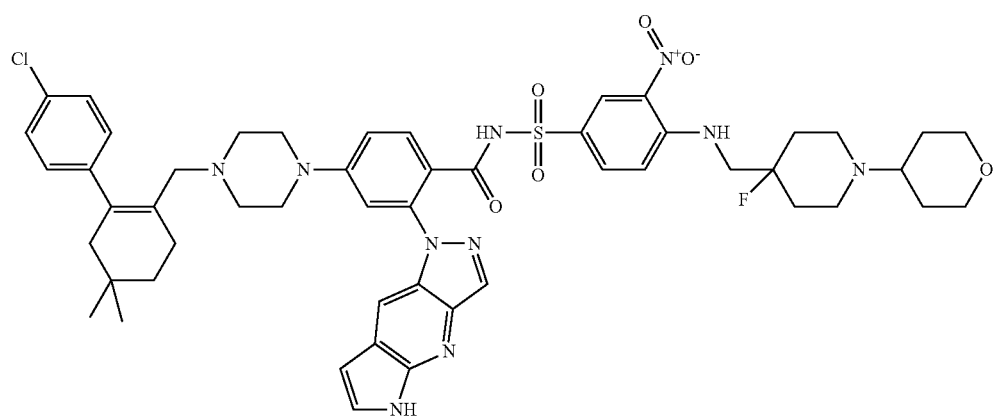
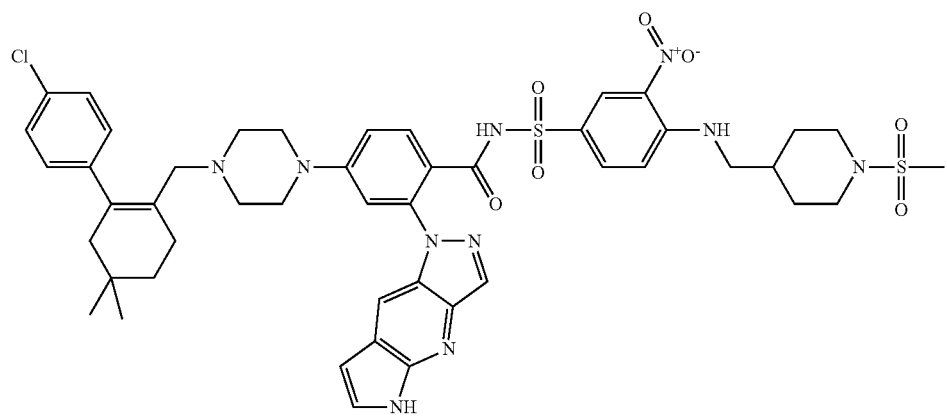
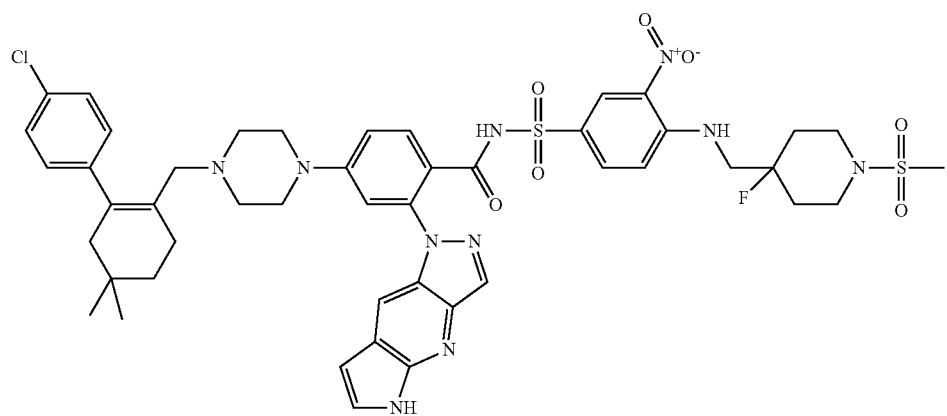

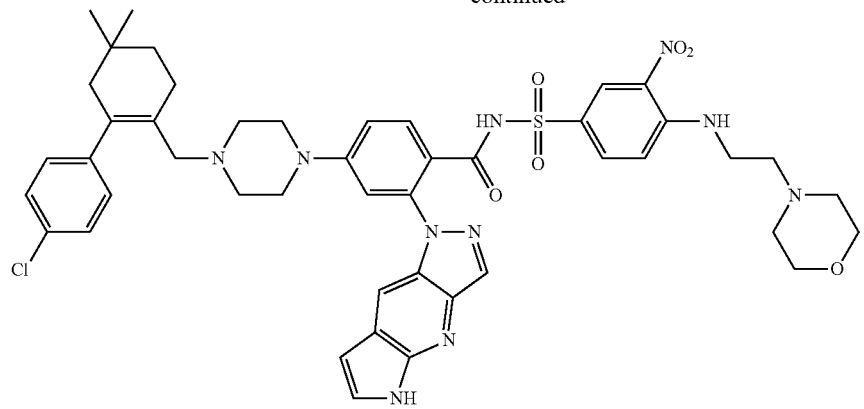
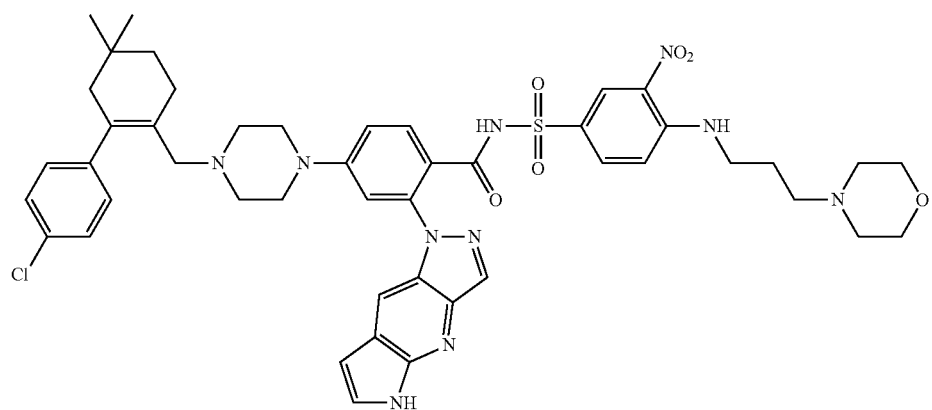
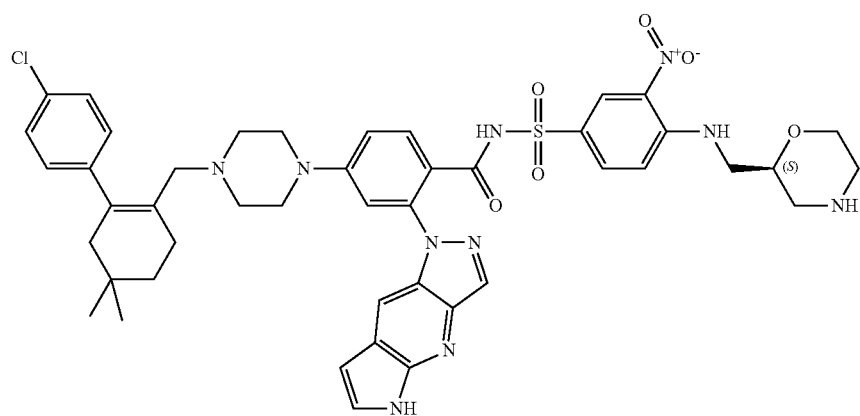
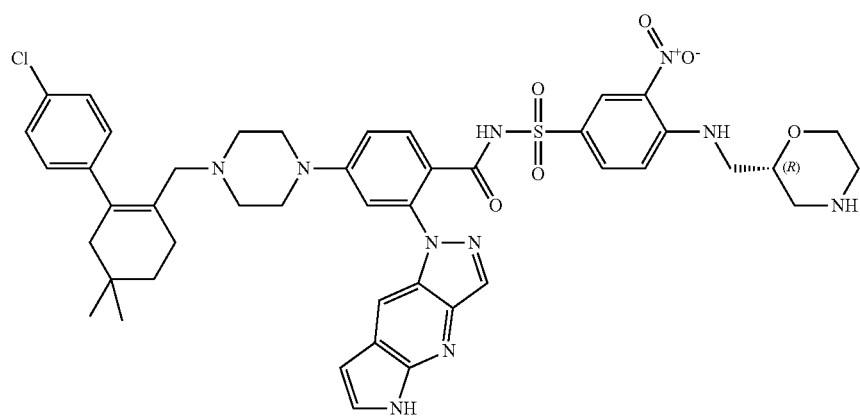

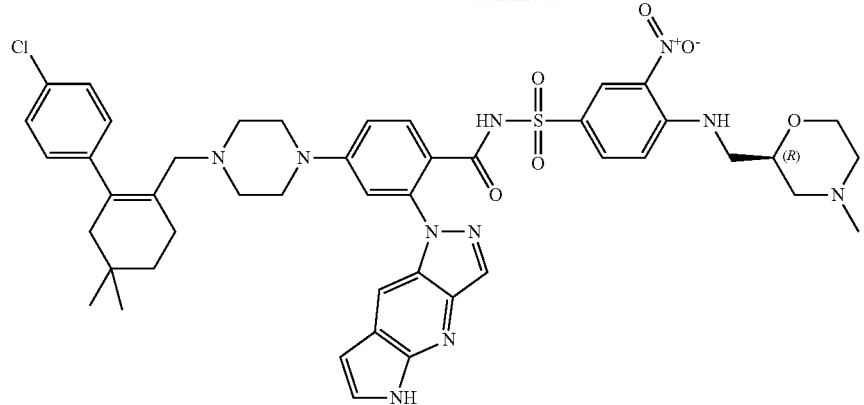
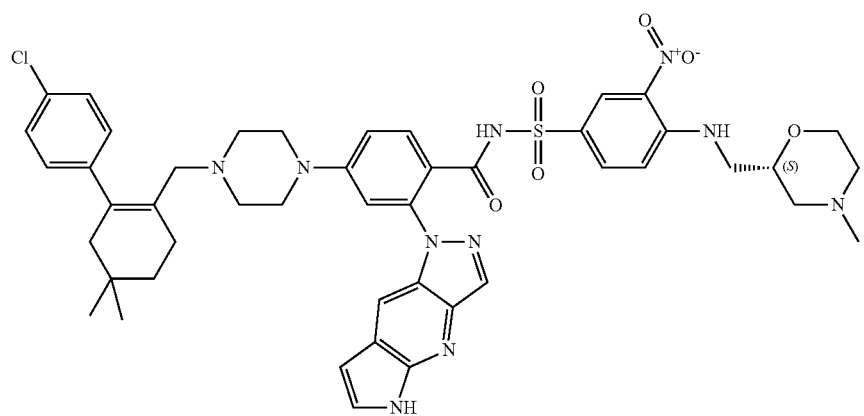
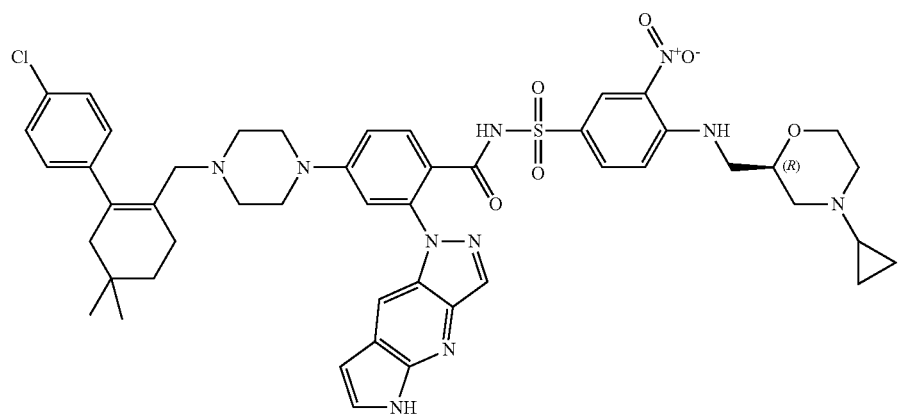
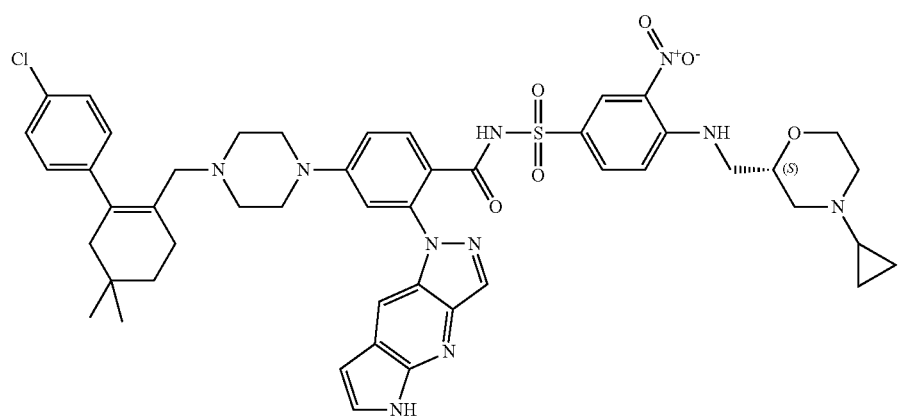

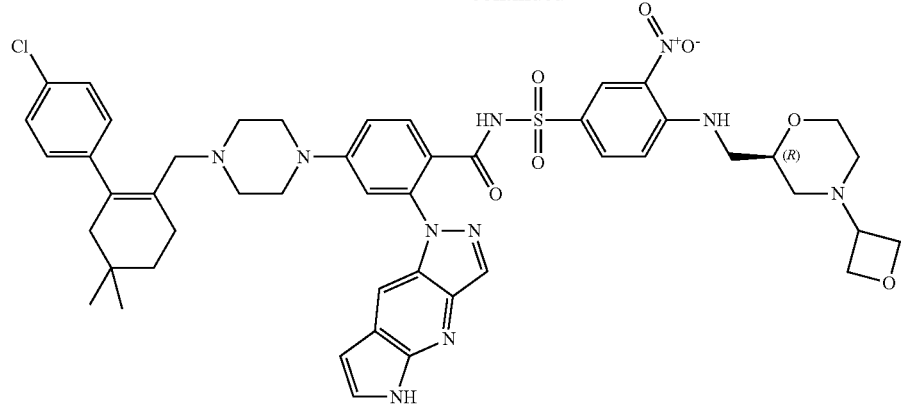
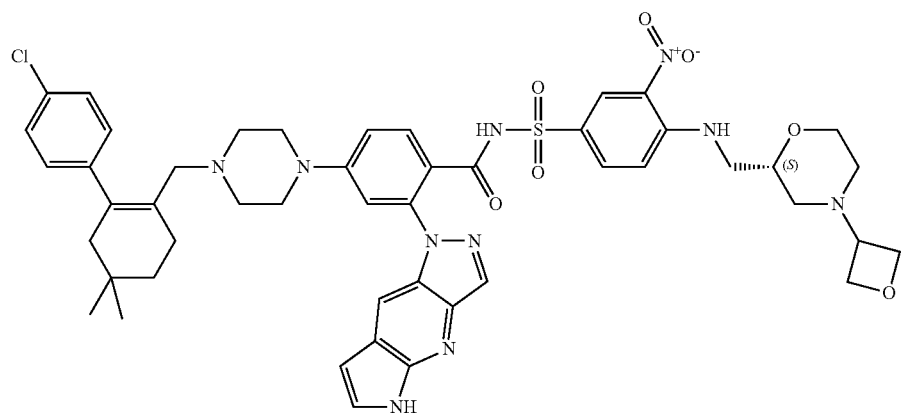
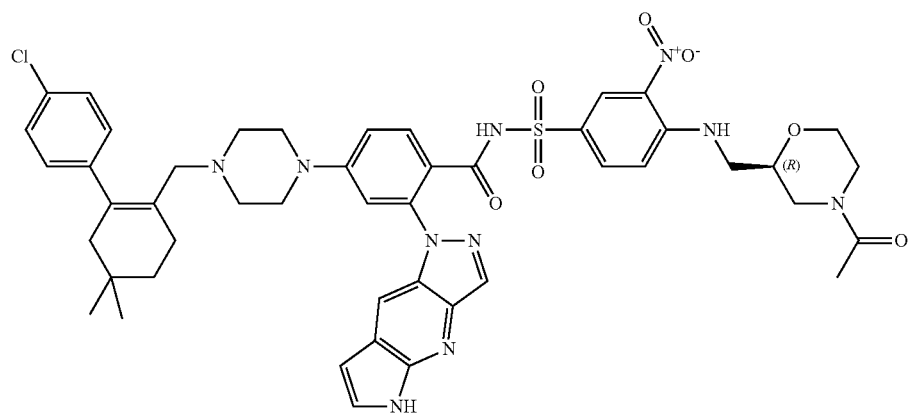
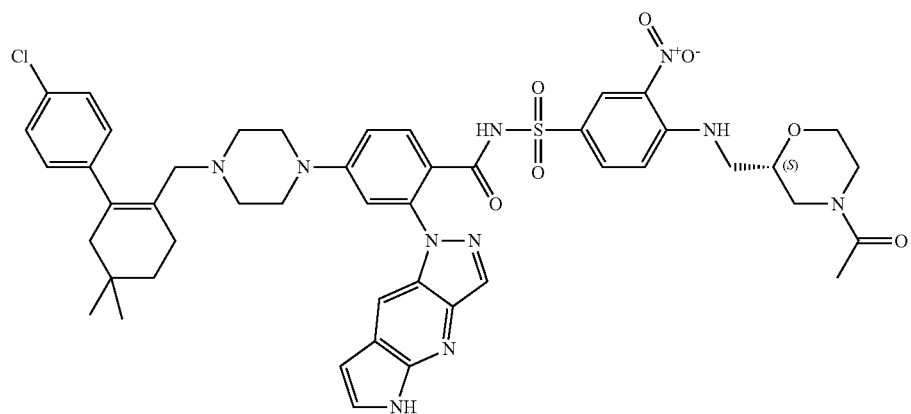

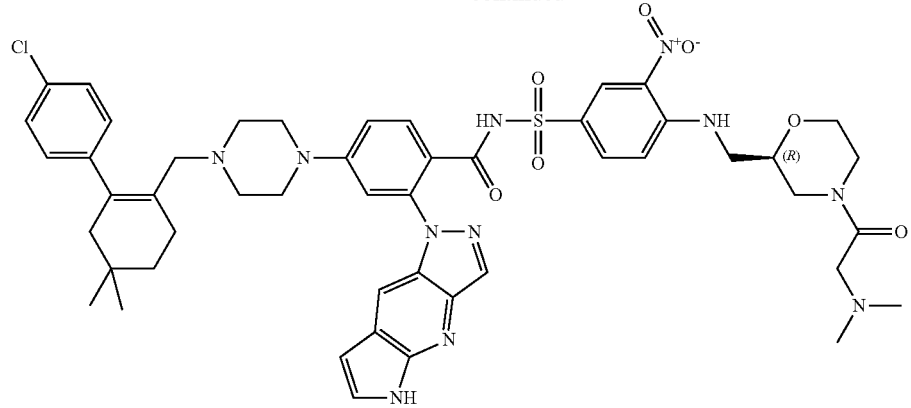
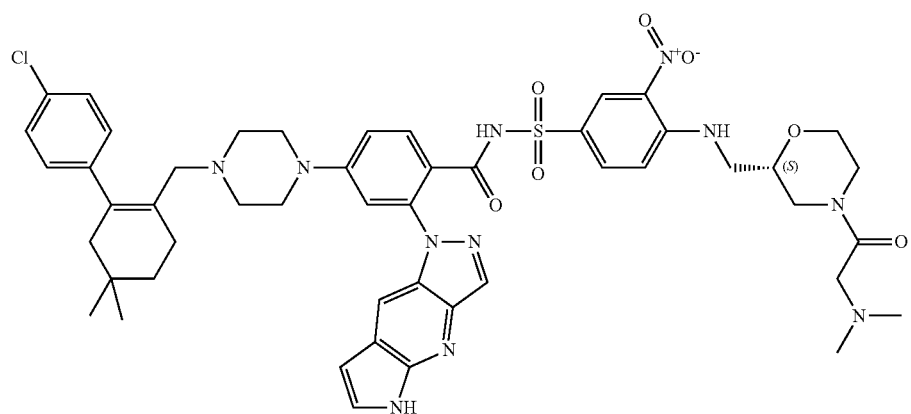
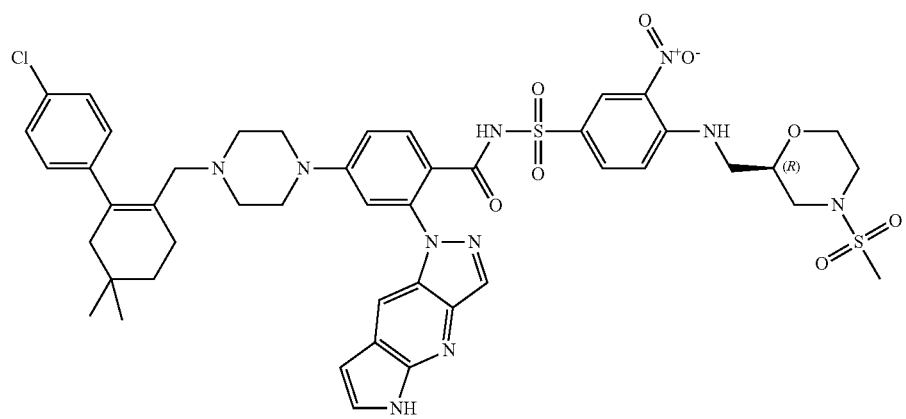
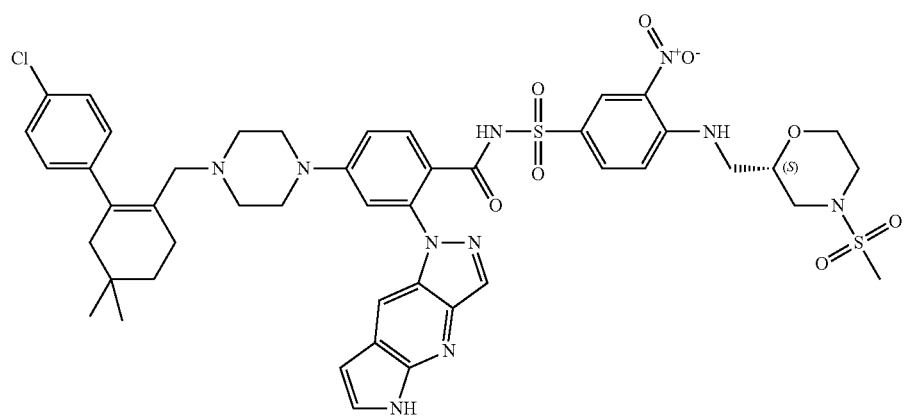

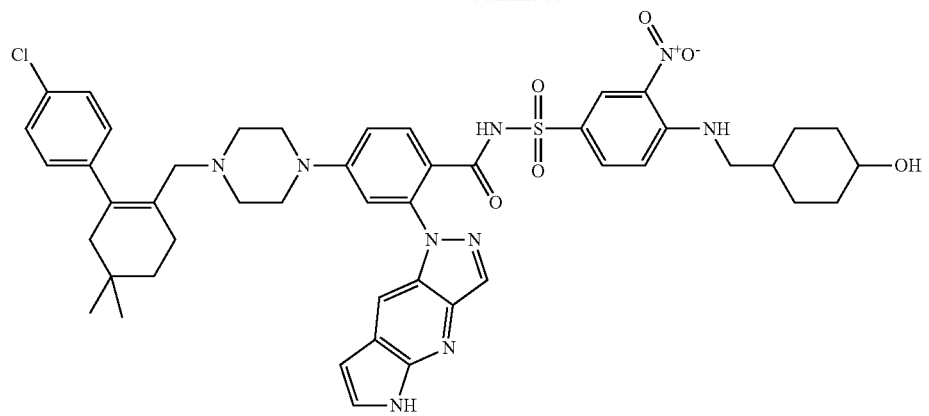
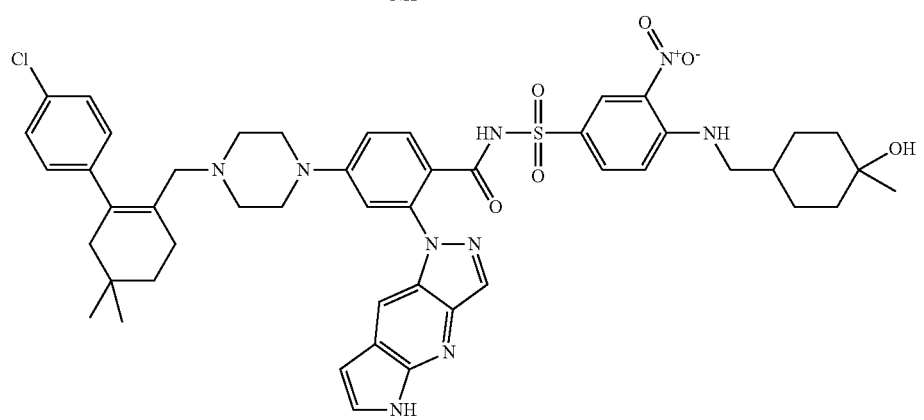
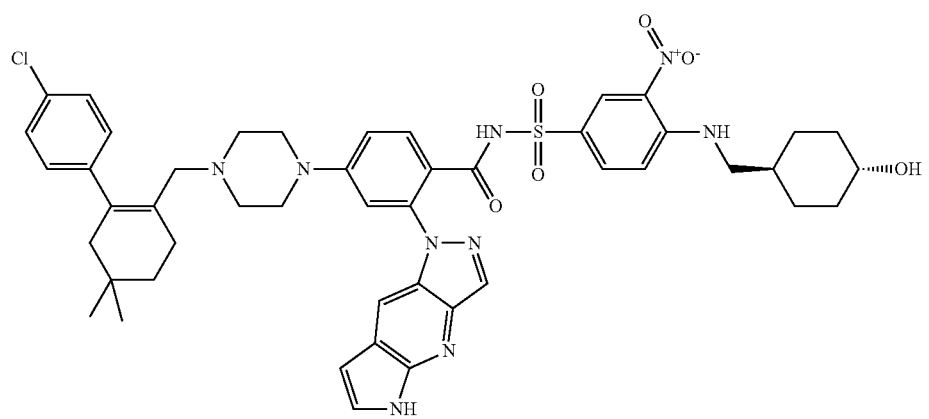
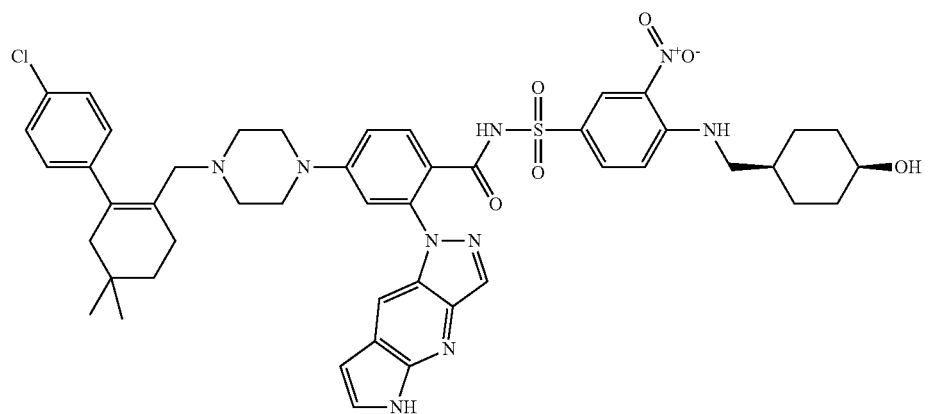

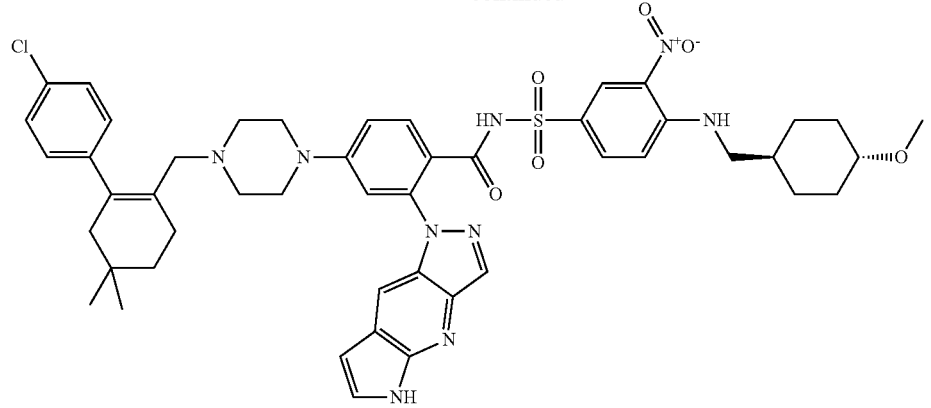
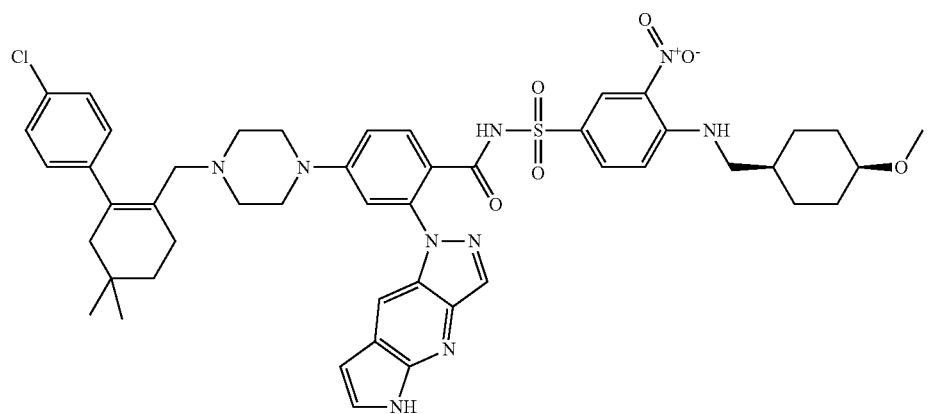
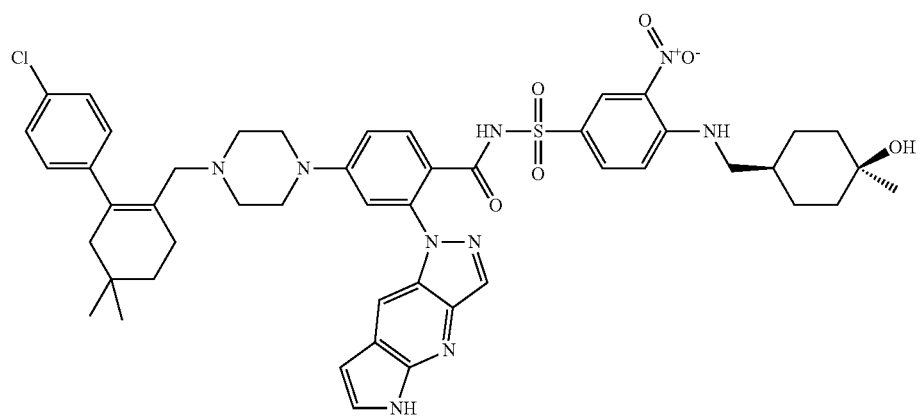
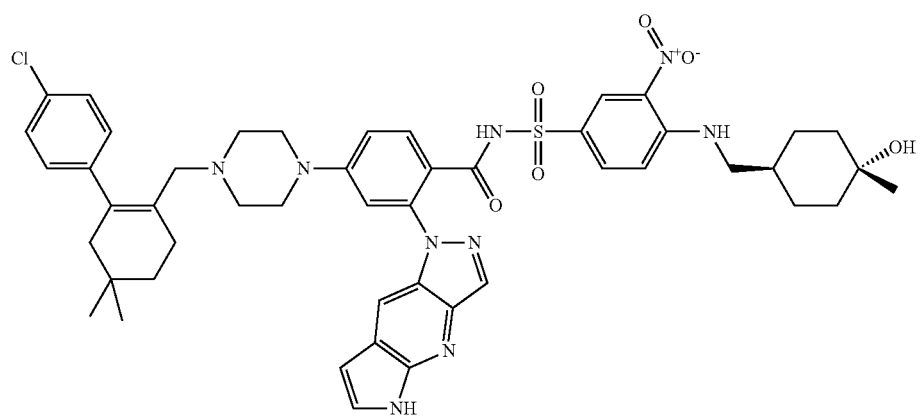

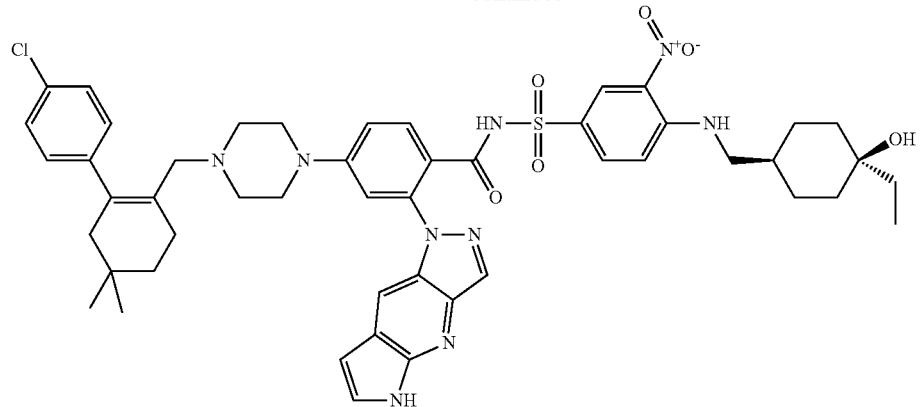
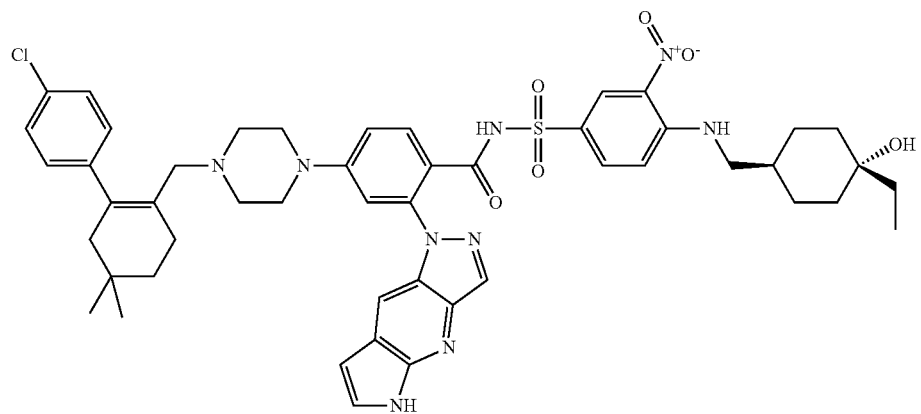
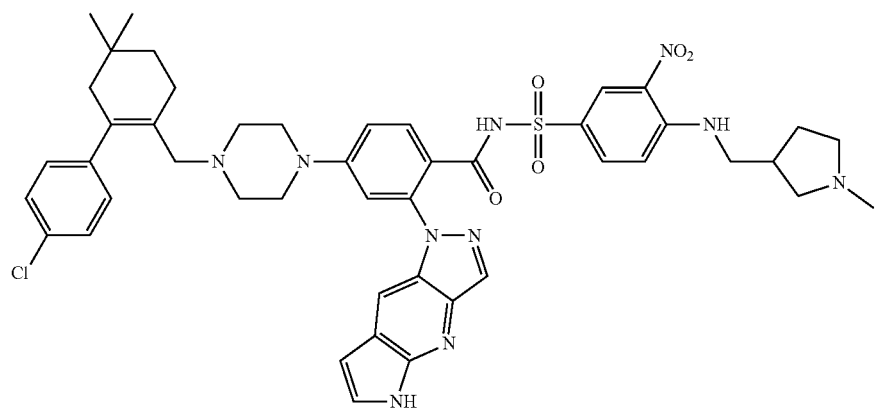
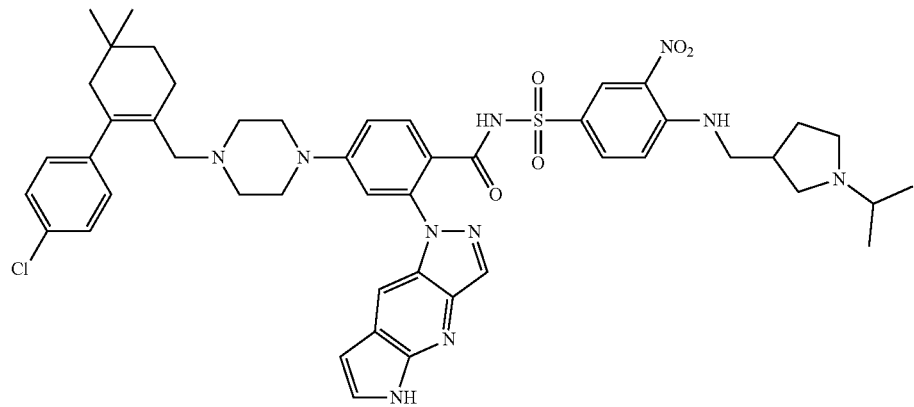

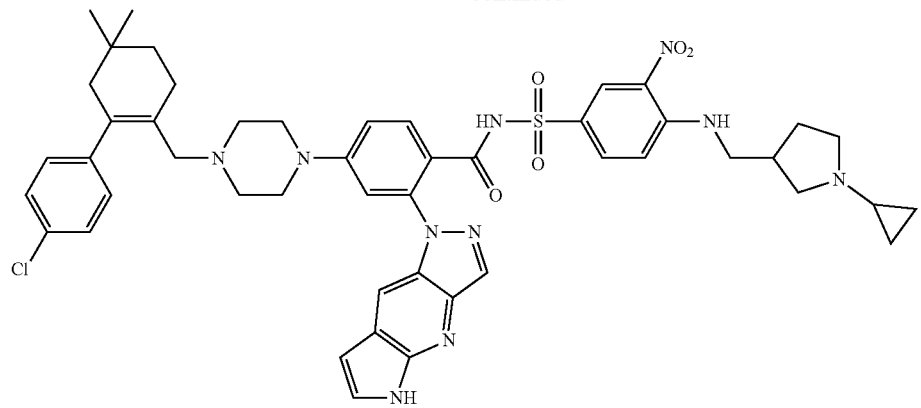
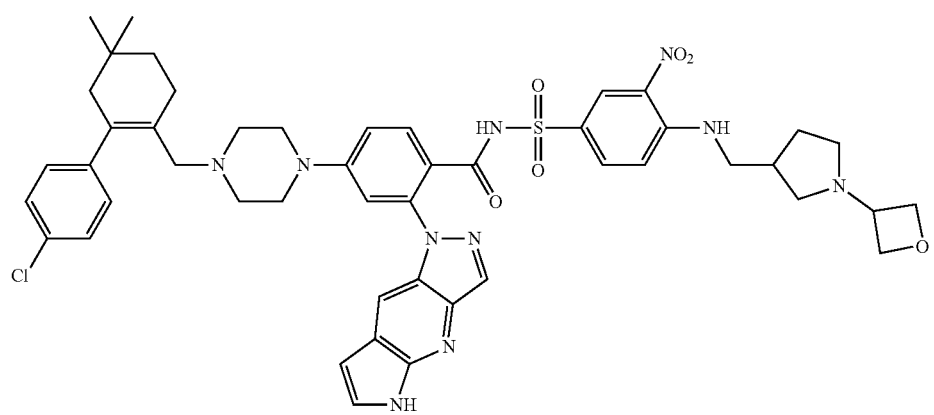
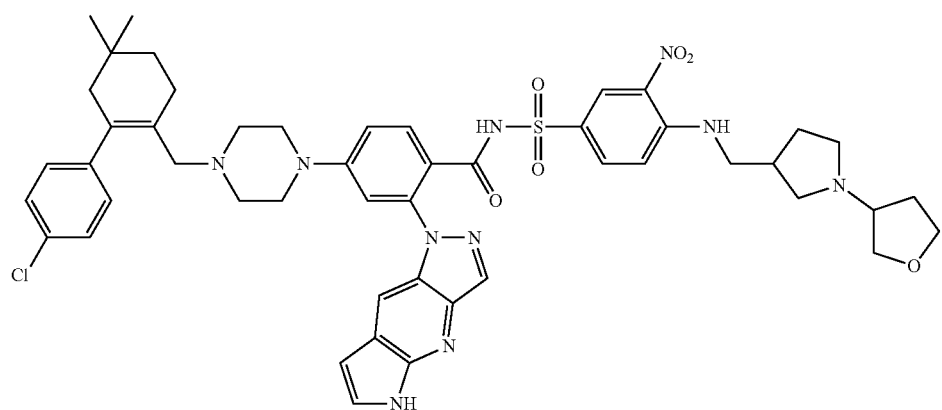
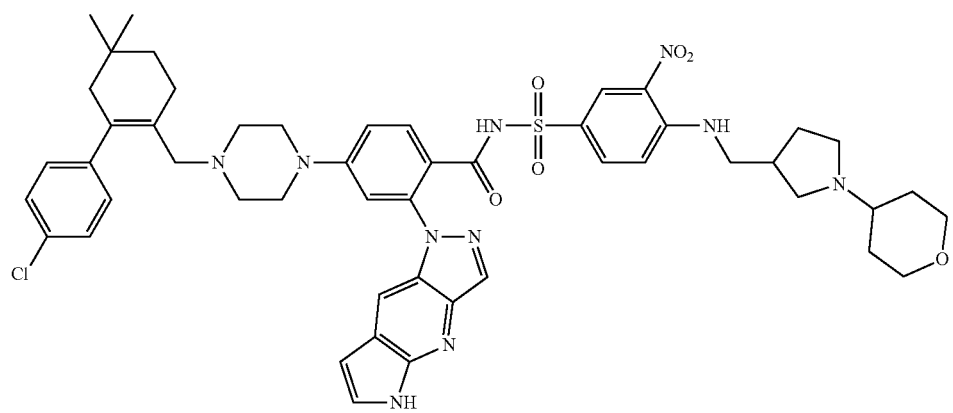

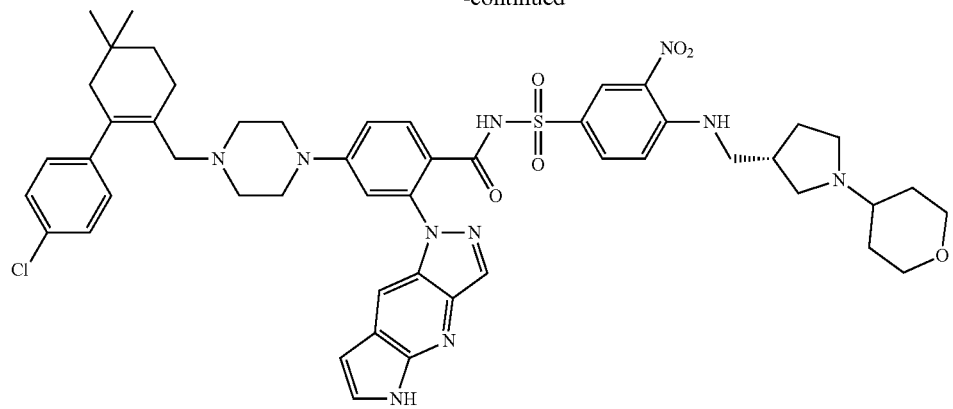
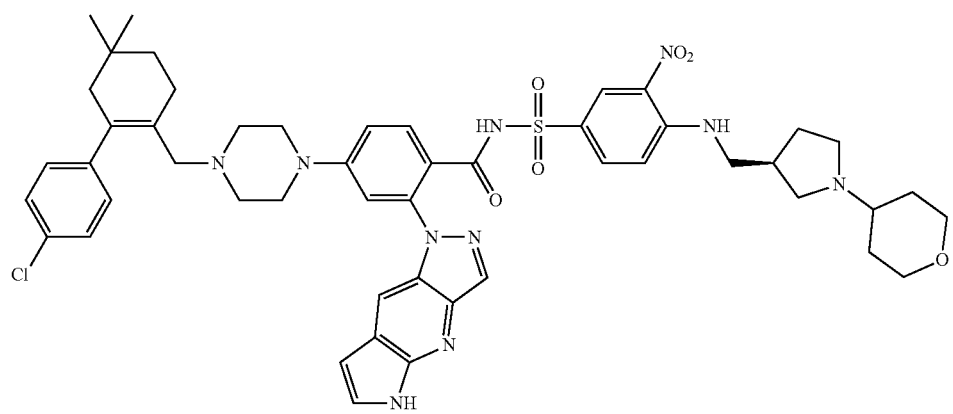
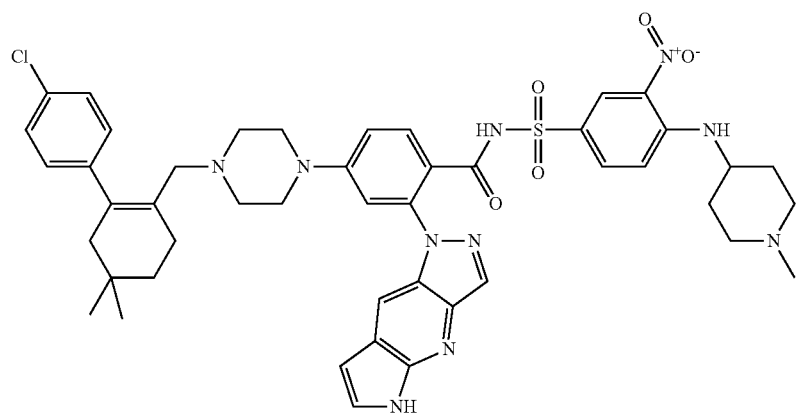
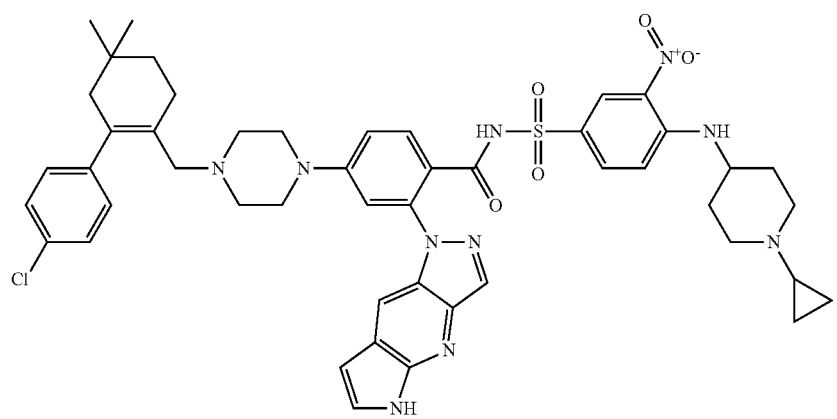

-continued
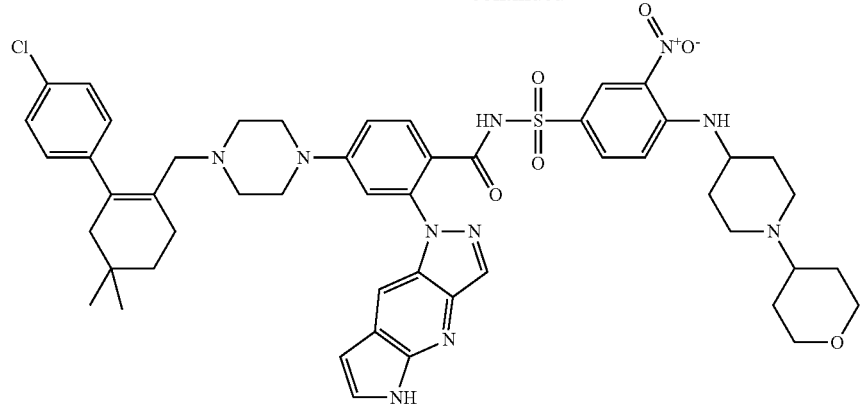
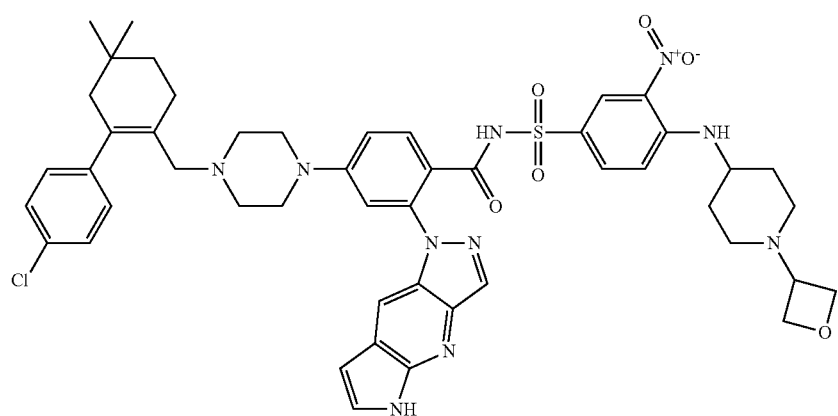
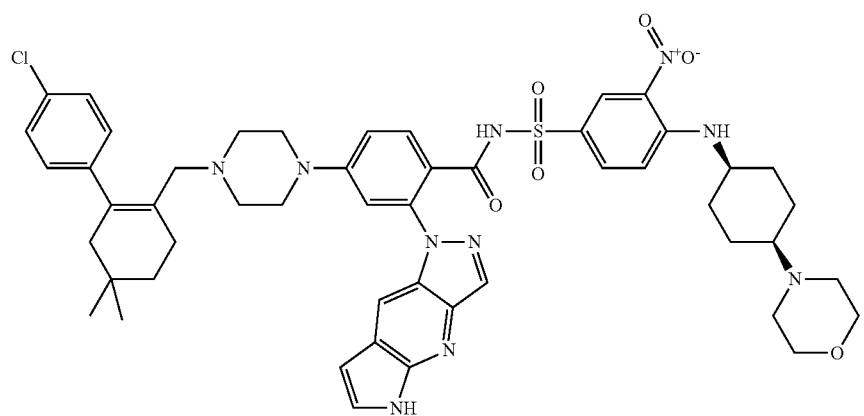
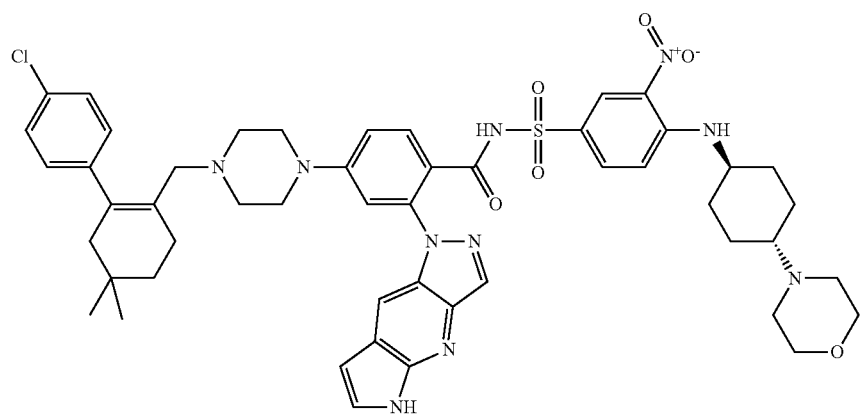

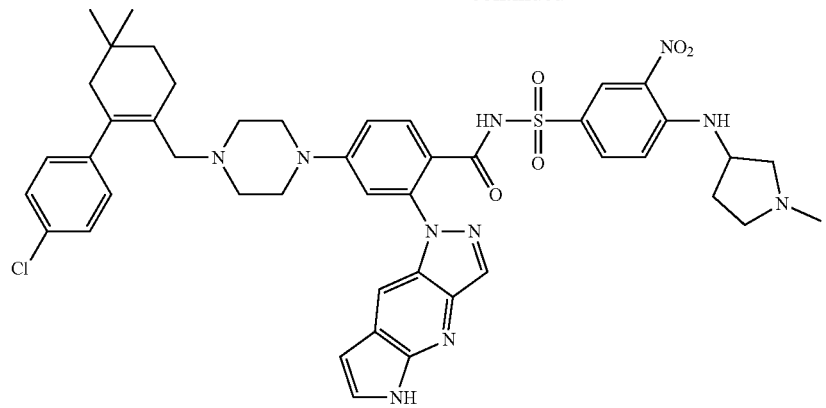
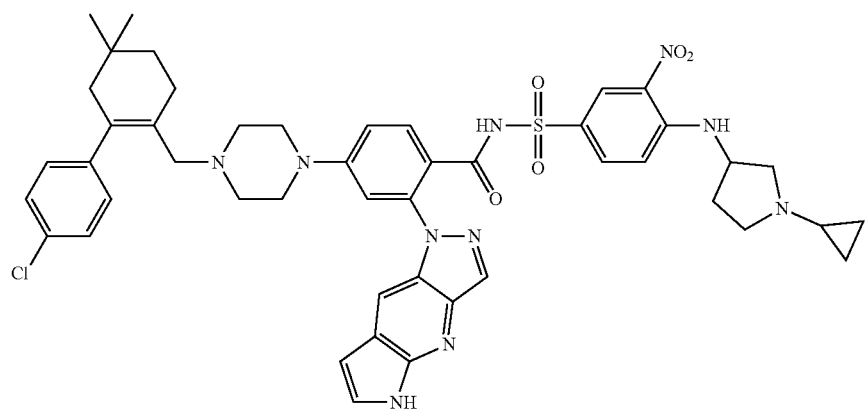
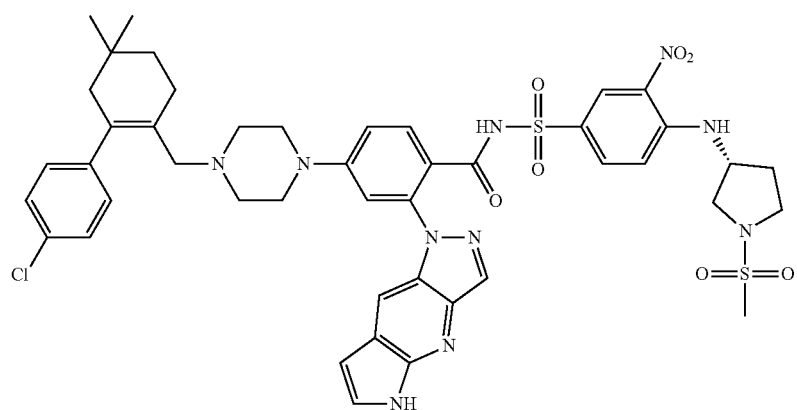
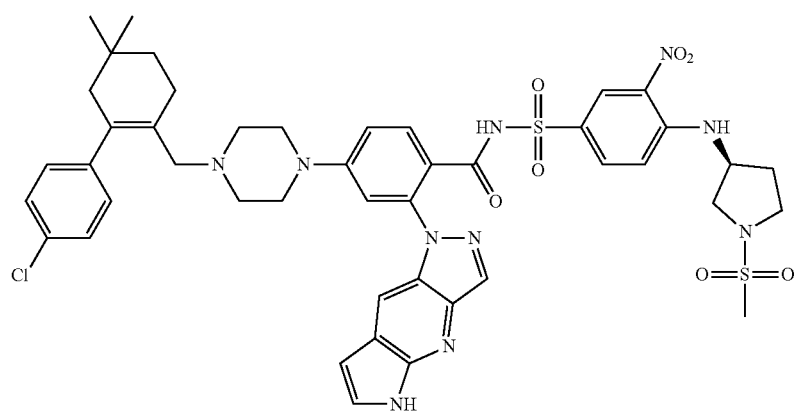

-continued
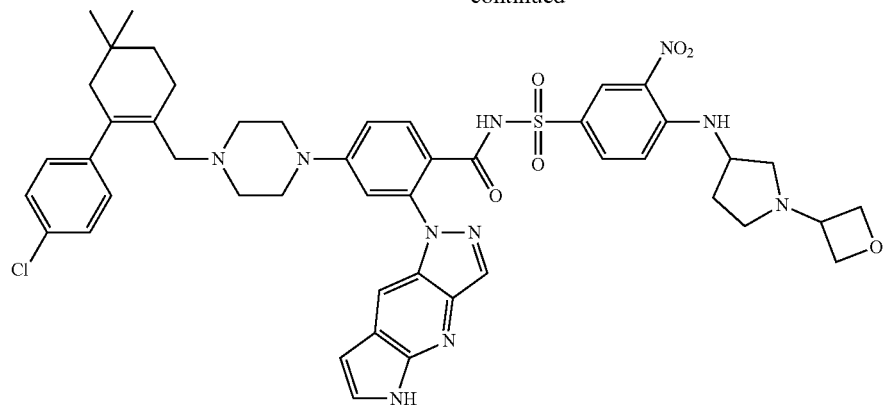
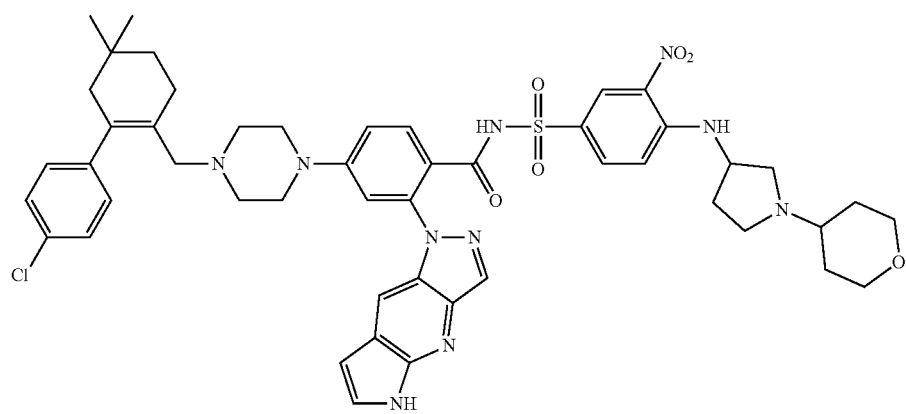
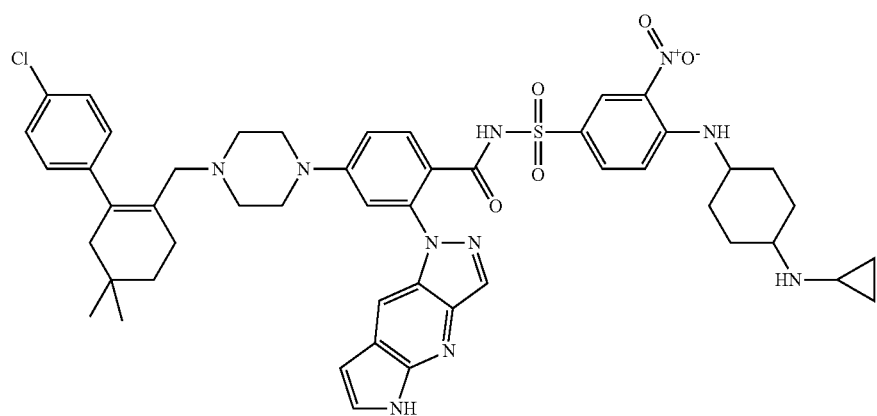
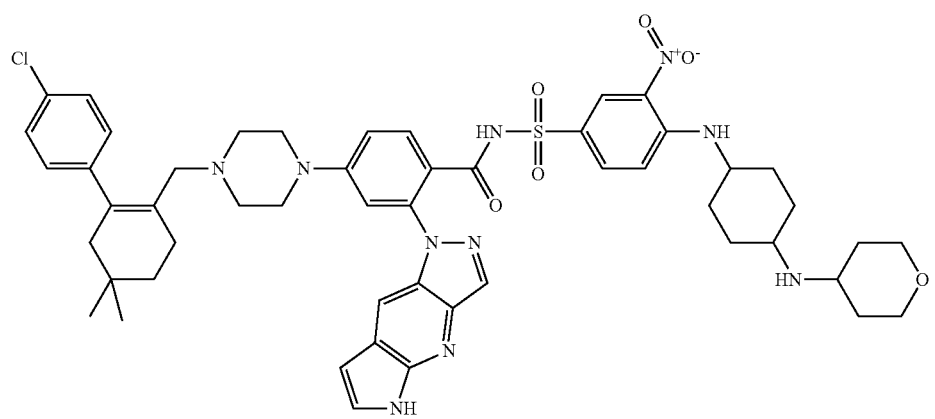

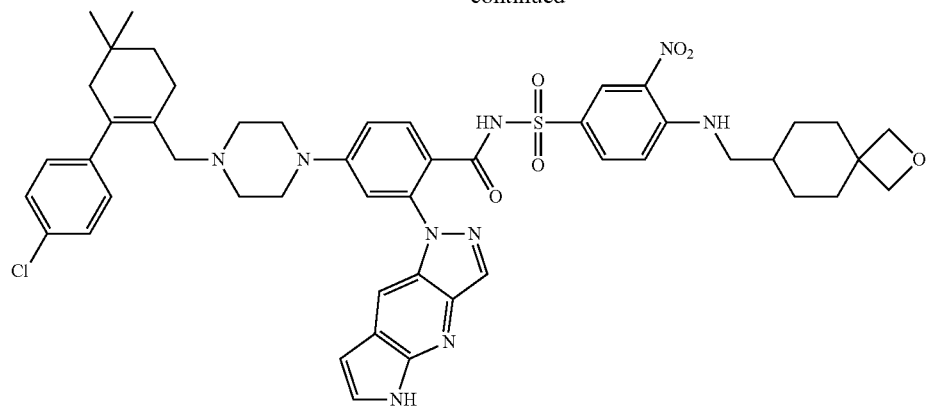
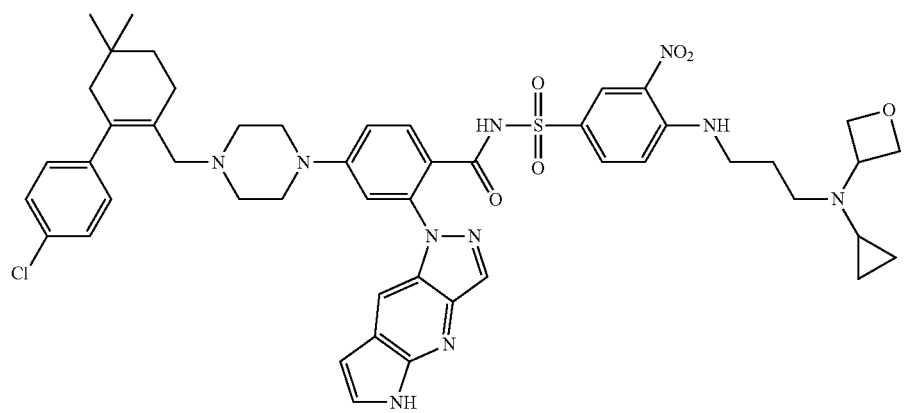
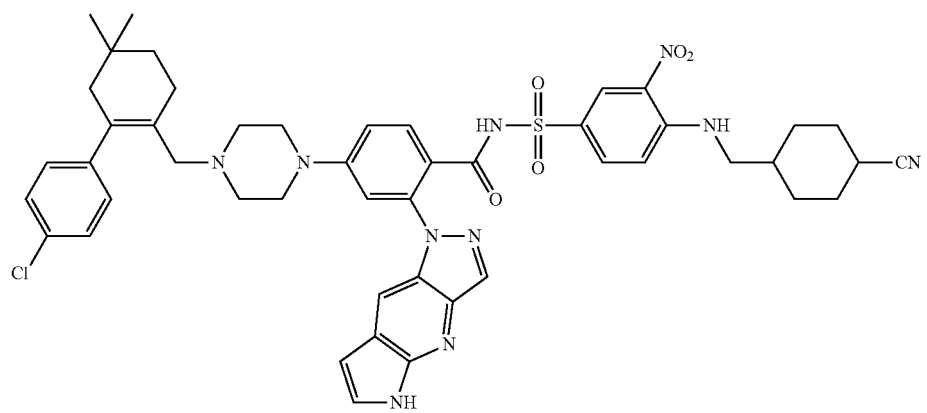
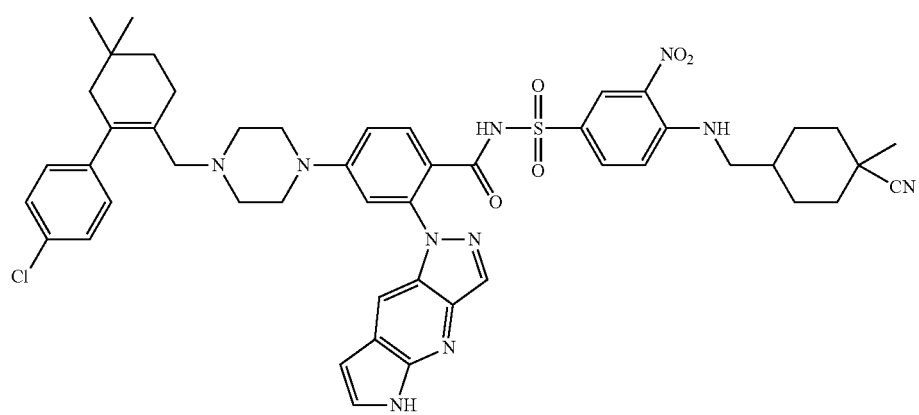

-continued
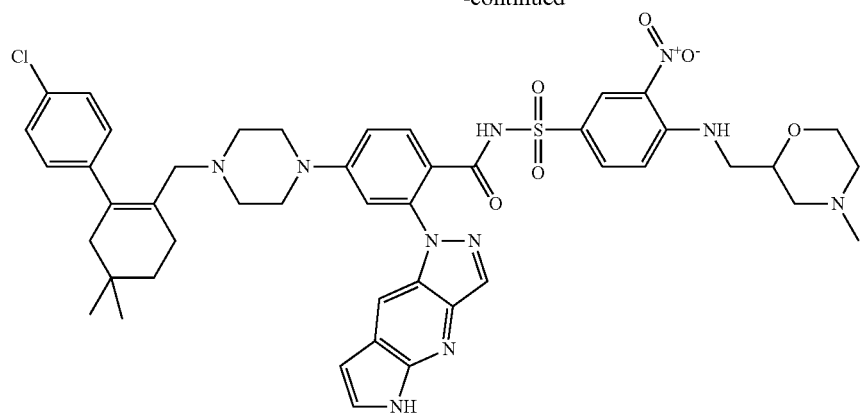
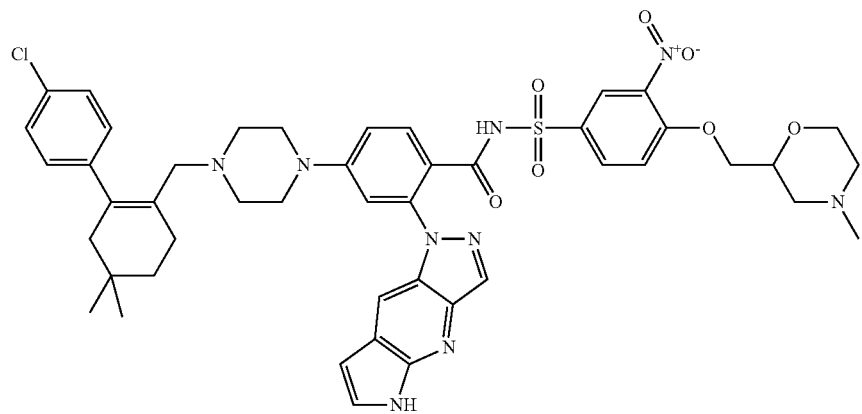
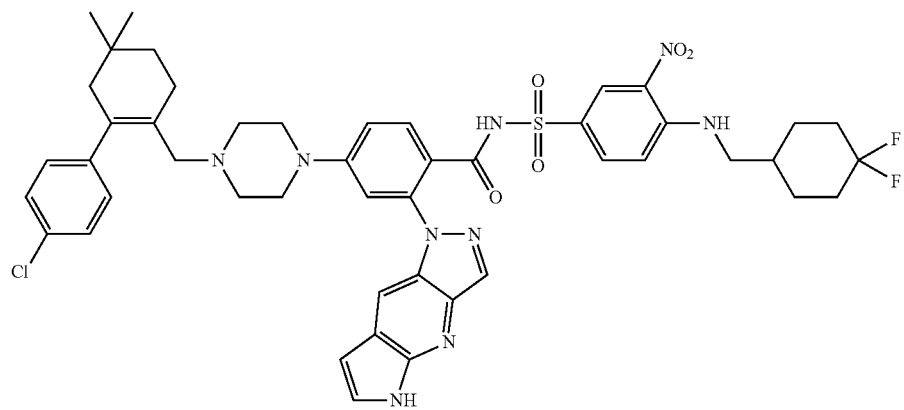
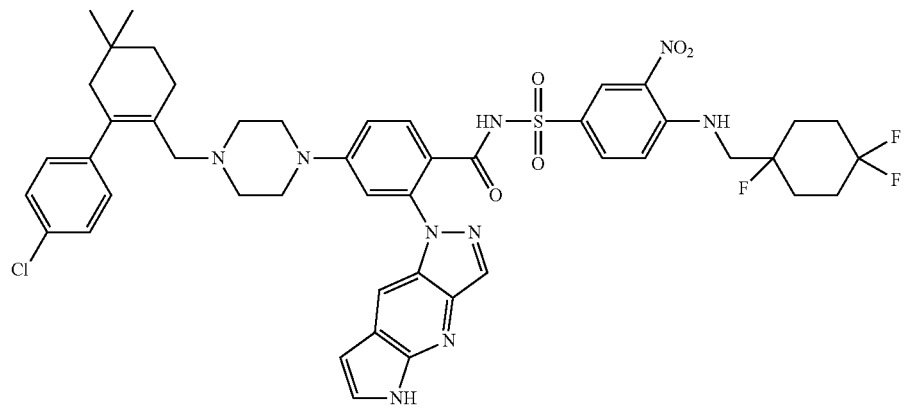

-continued
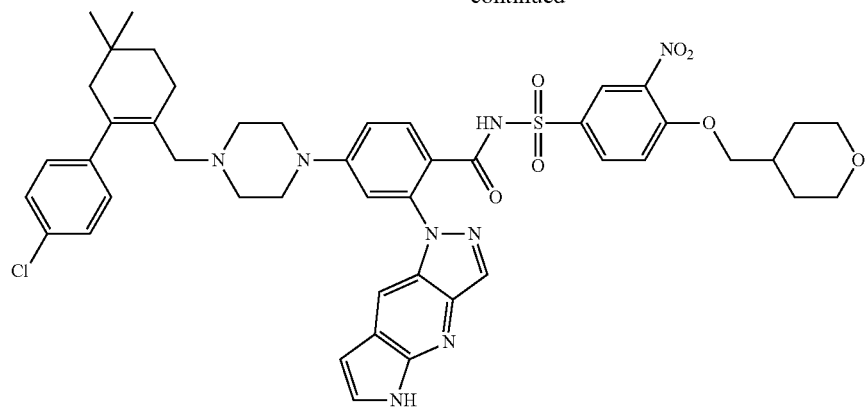
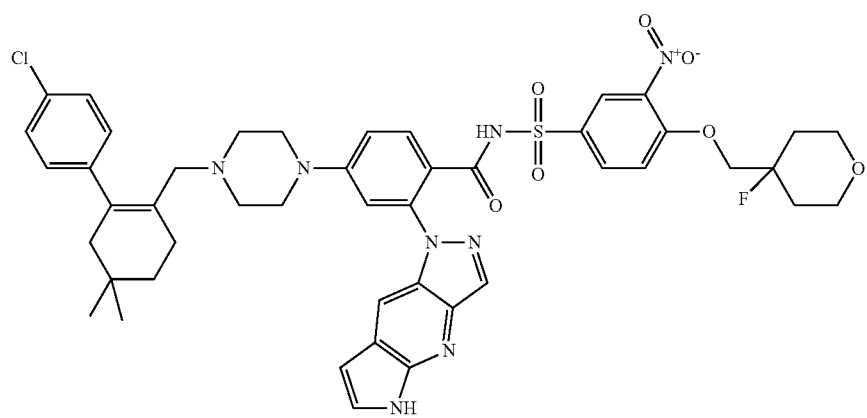
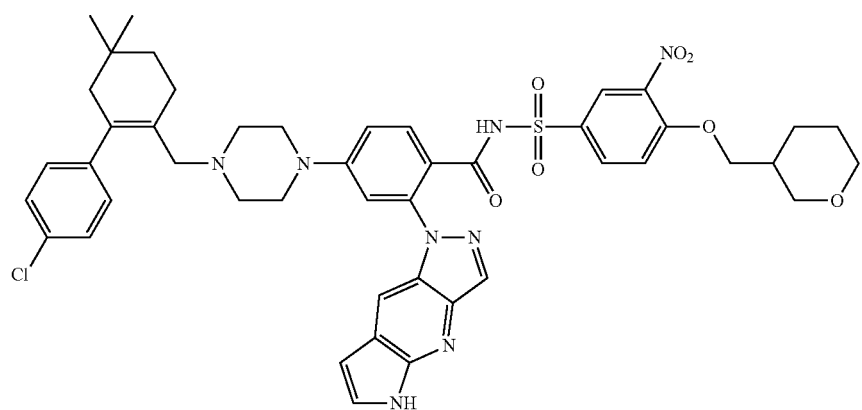
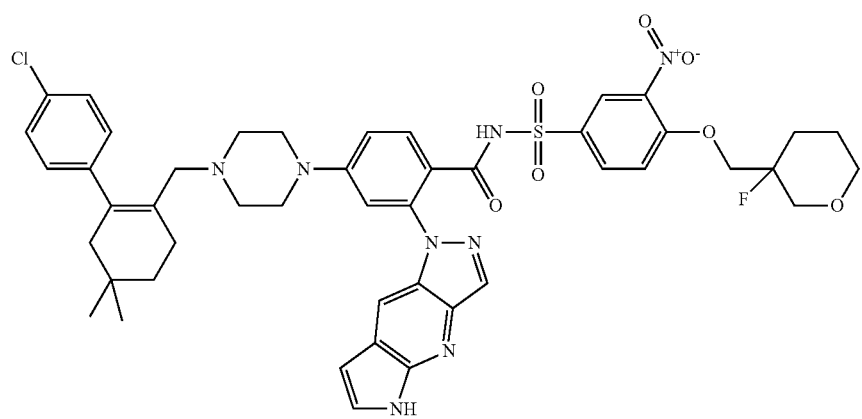

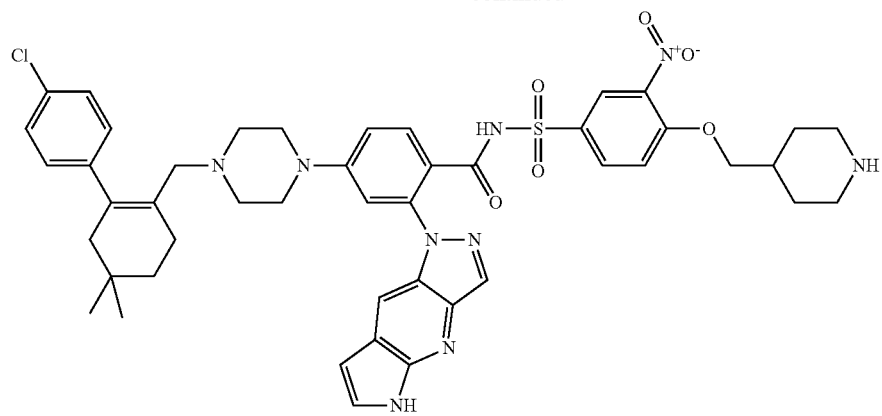
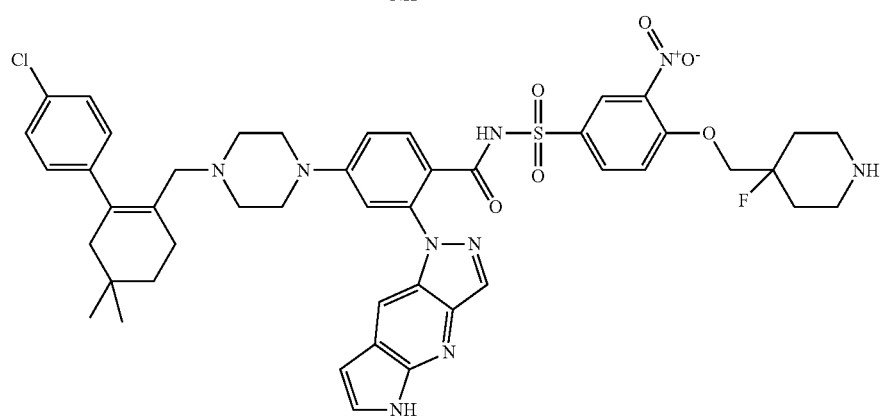
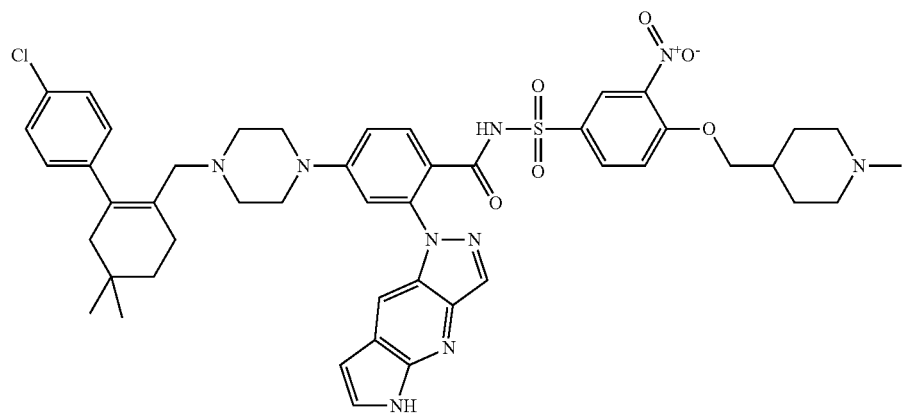
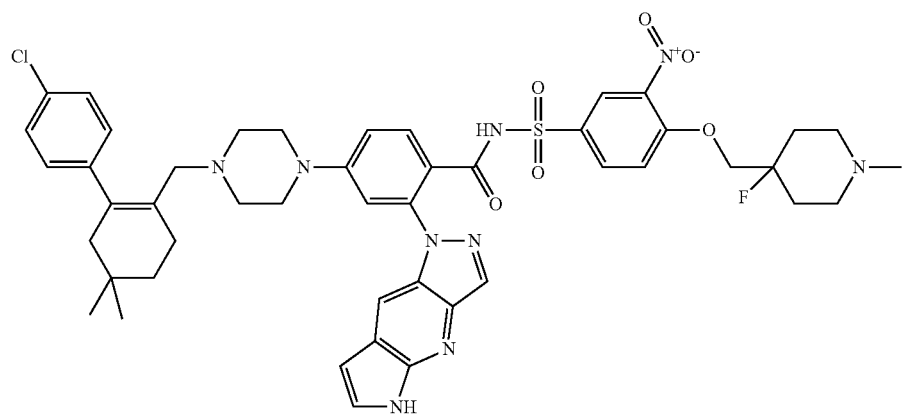

-continued
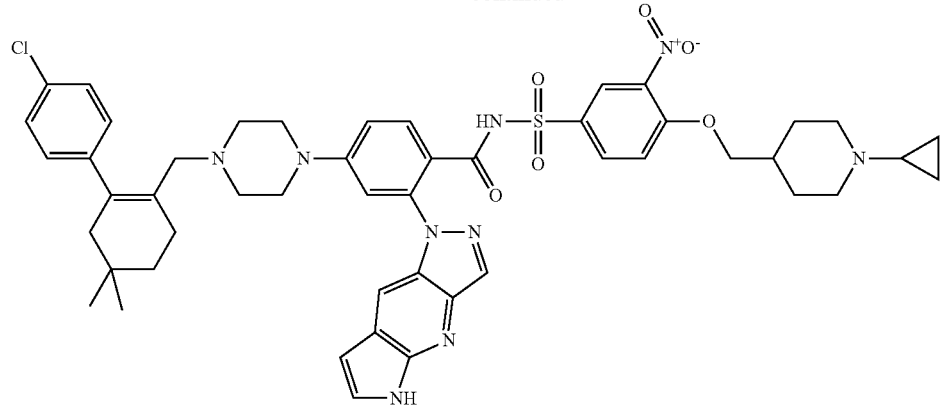
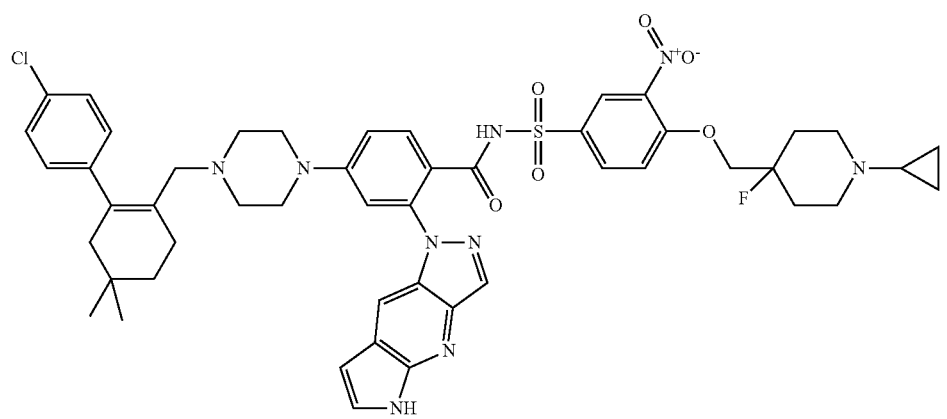
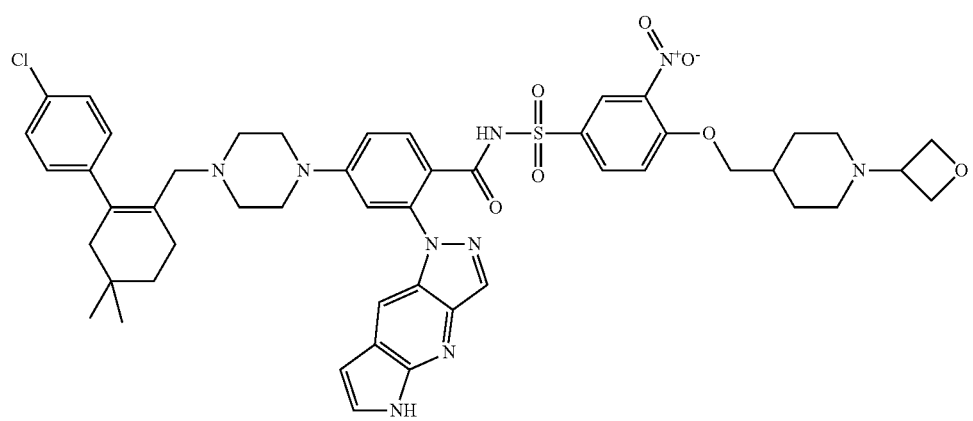
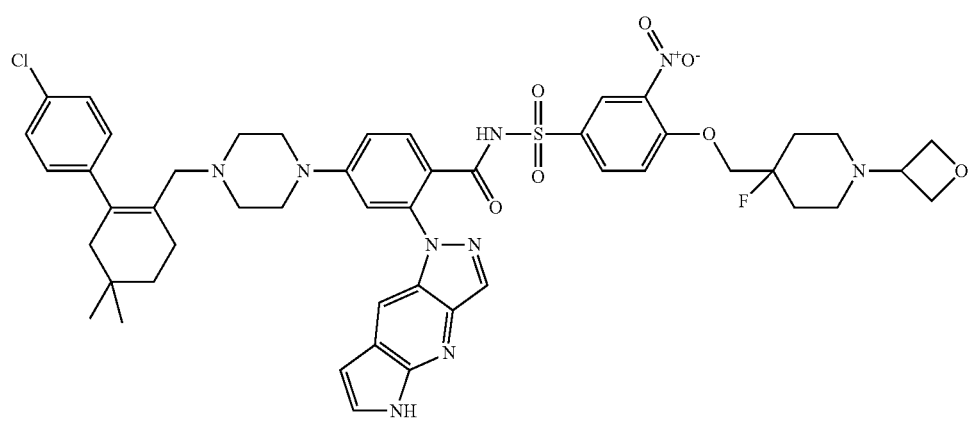

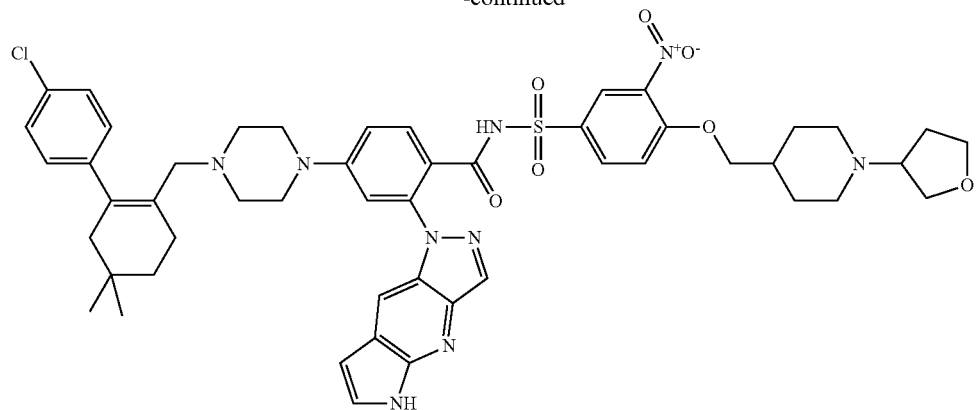
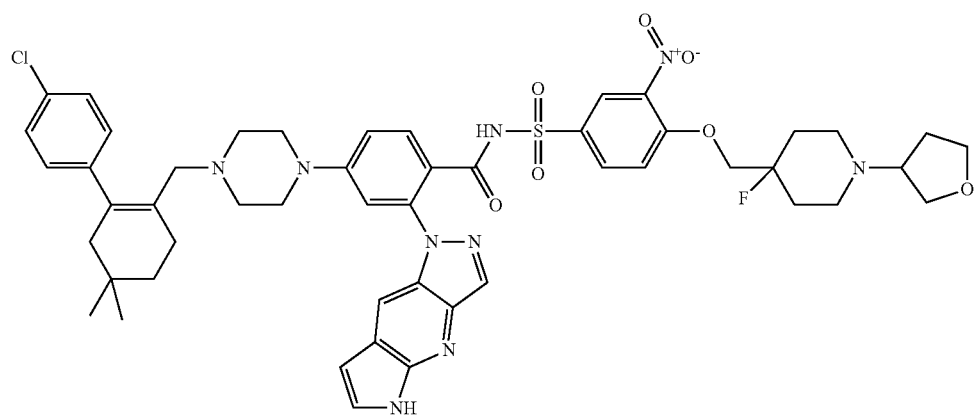
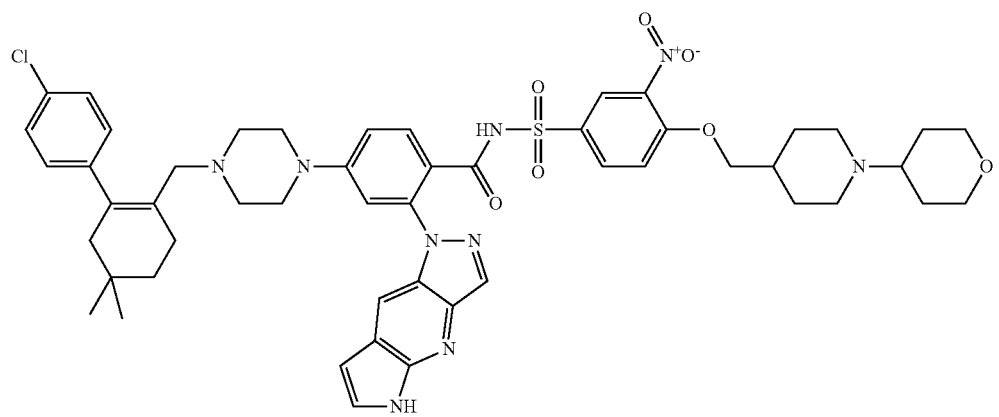
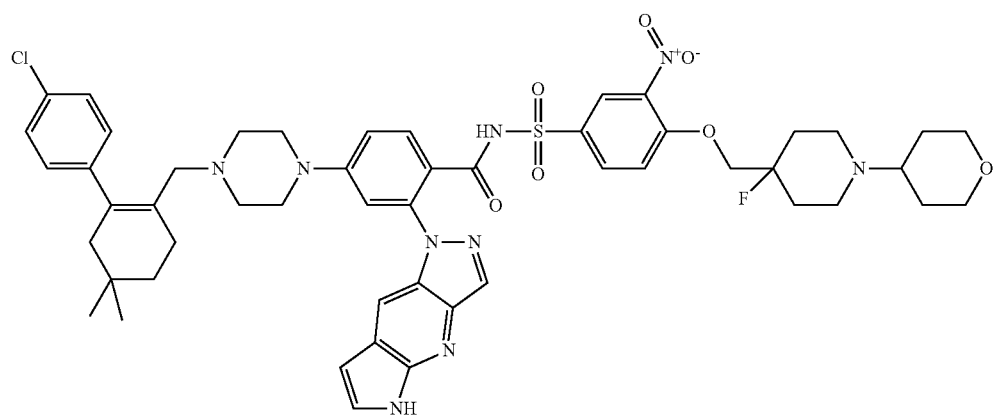

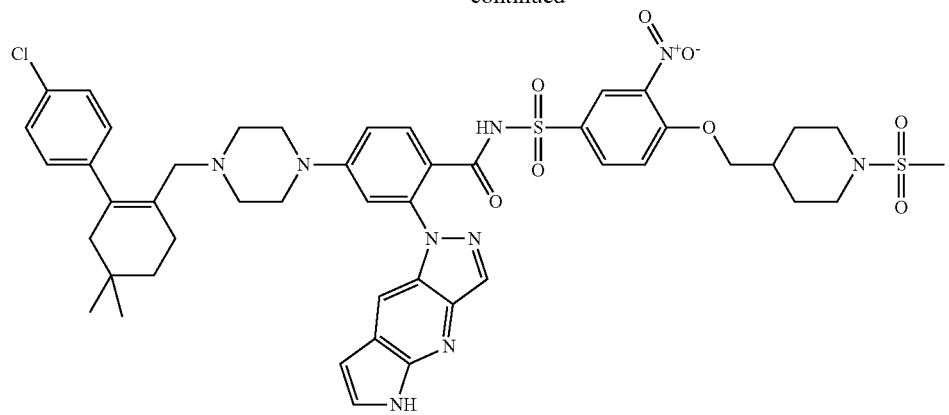
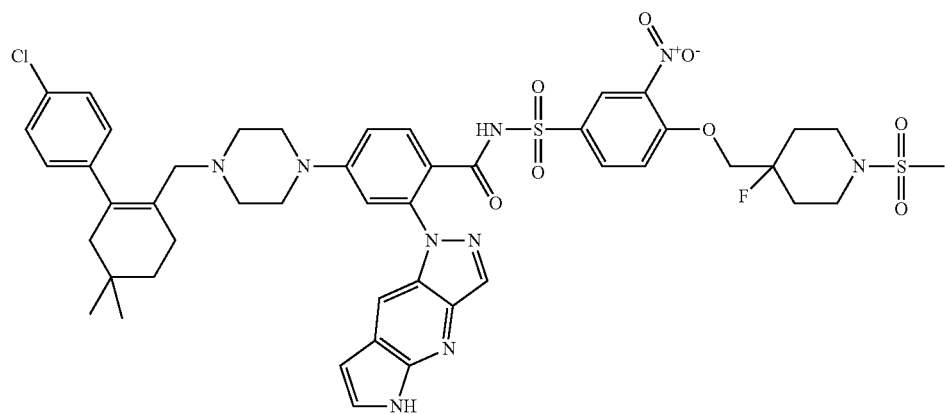
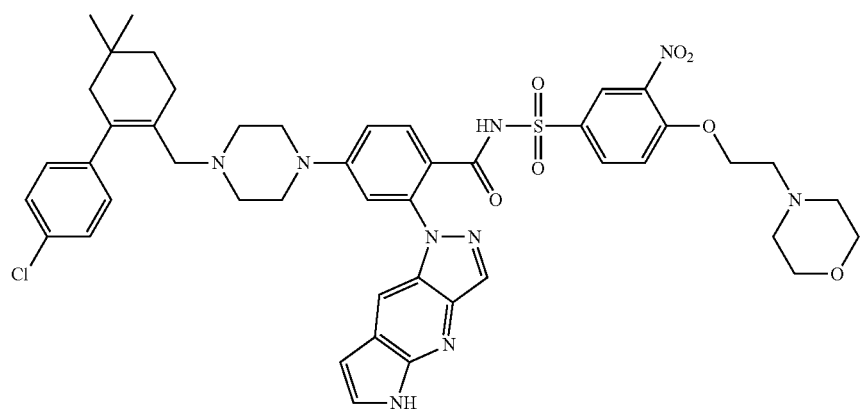
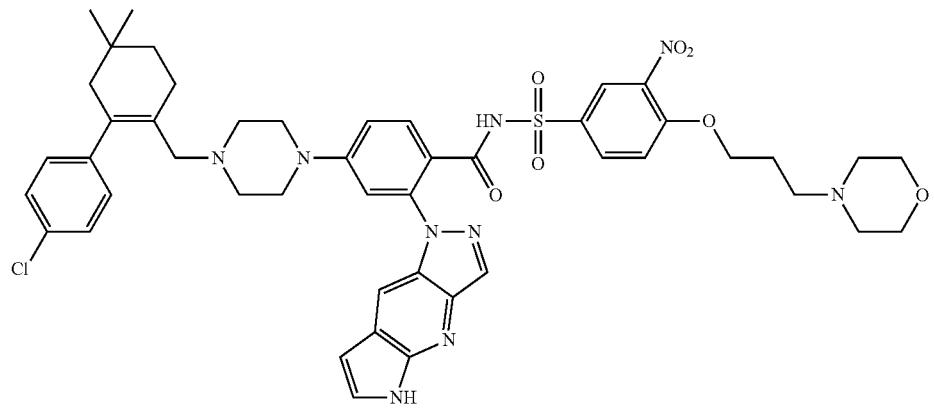

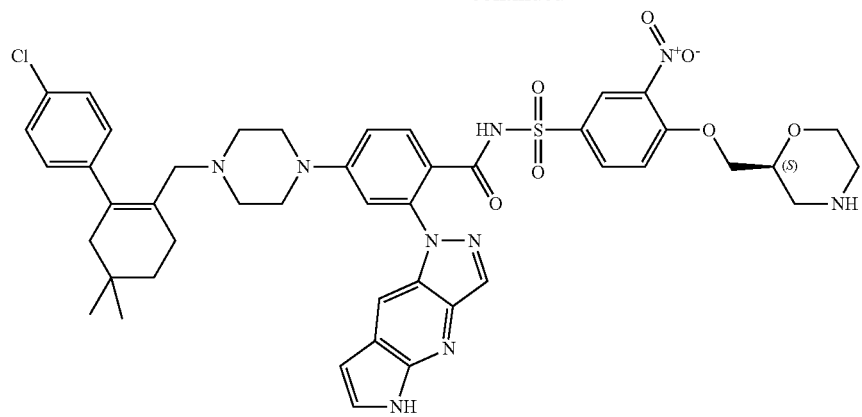
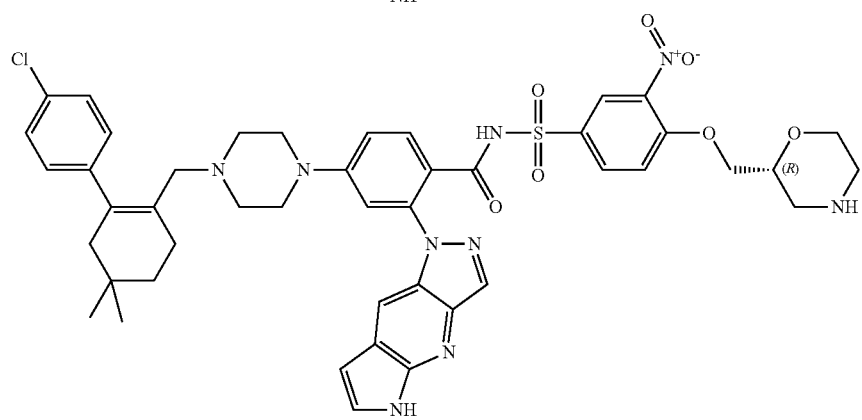
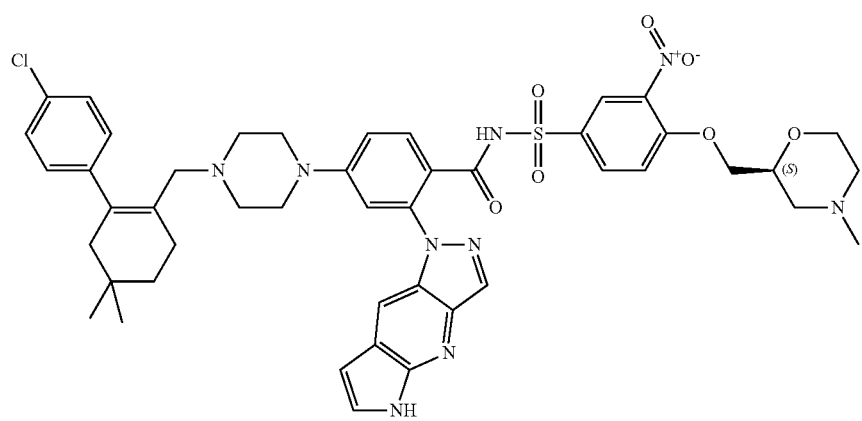
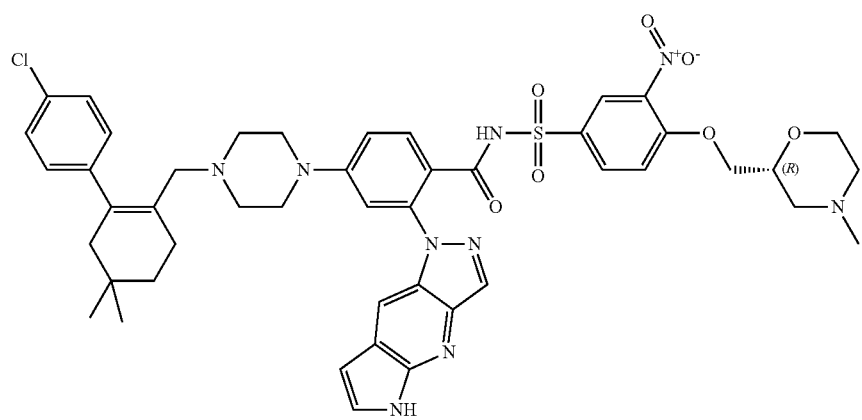

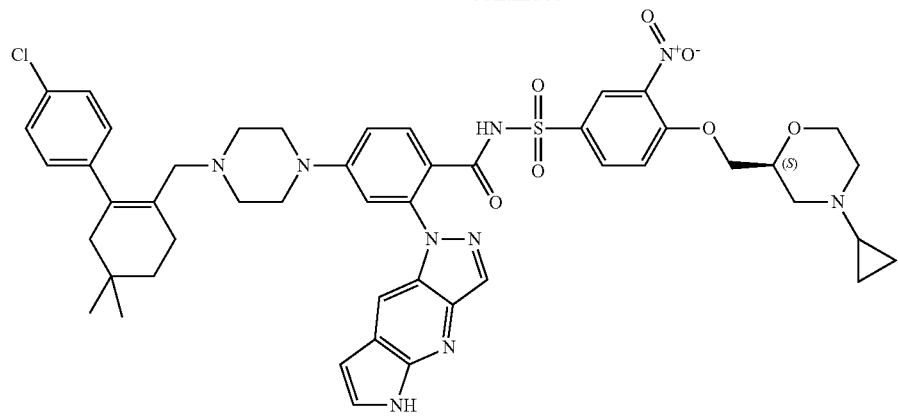
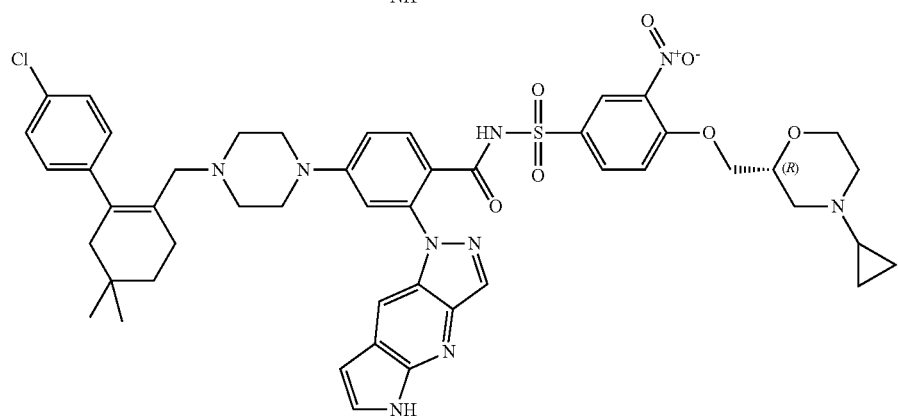
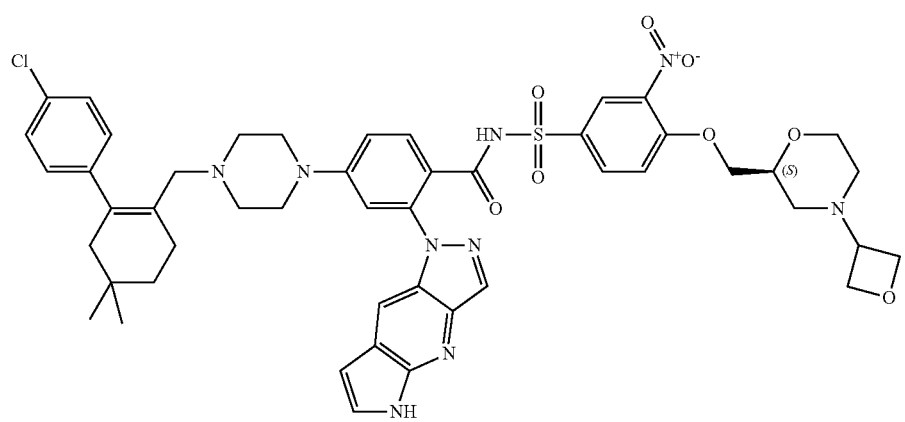
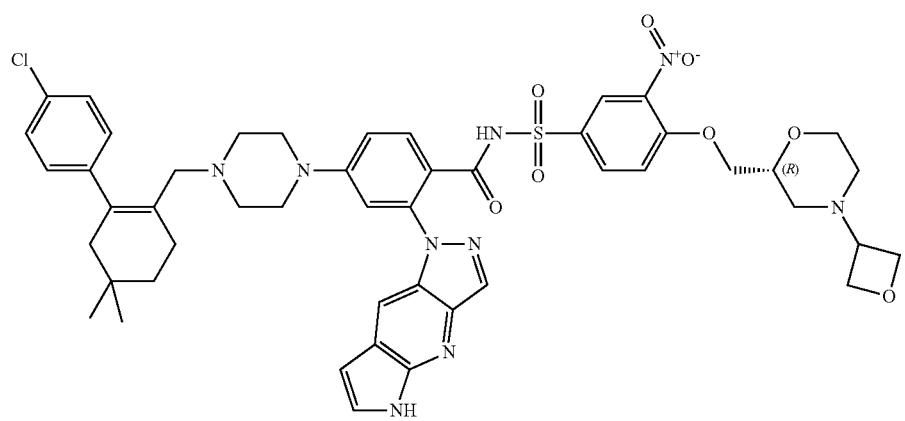

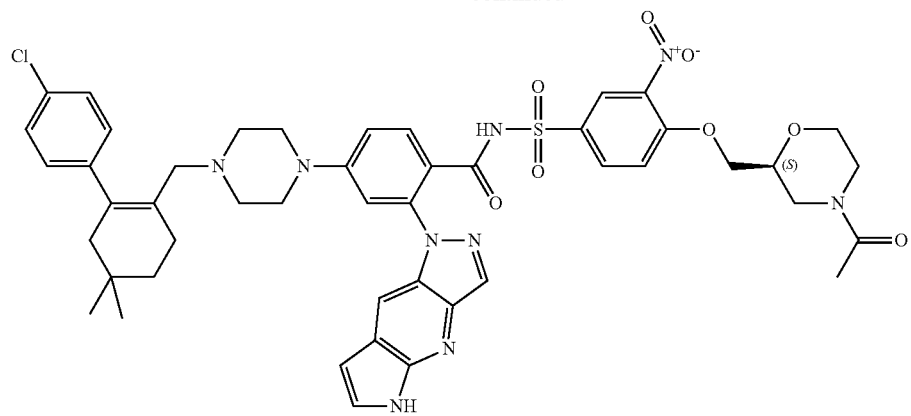
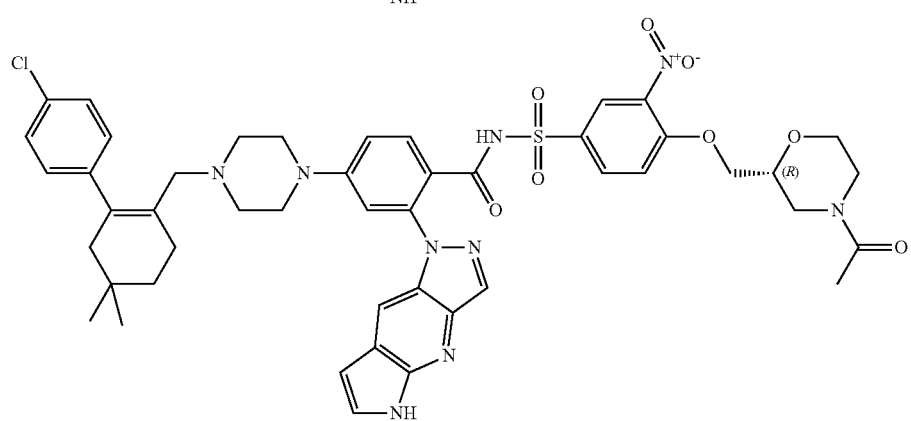
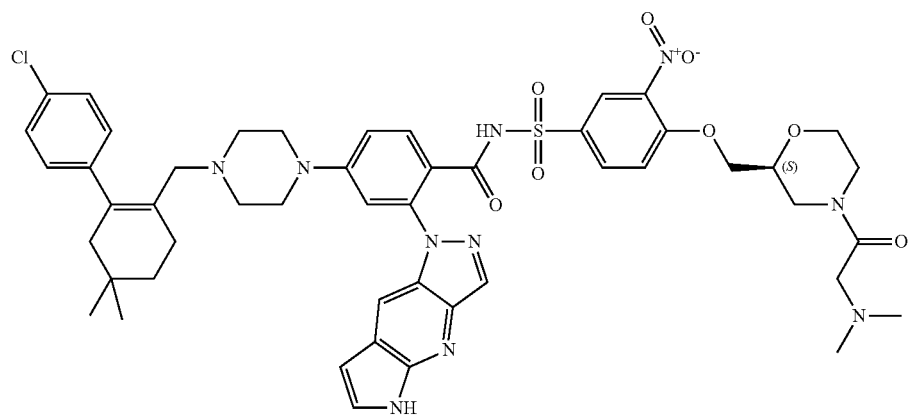
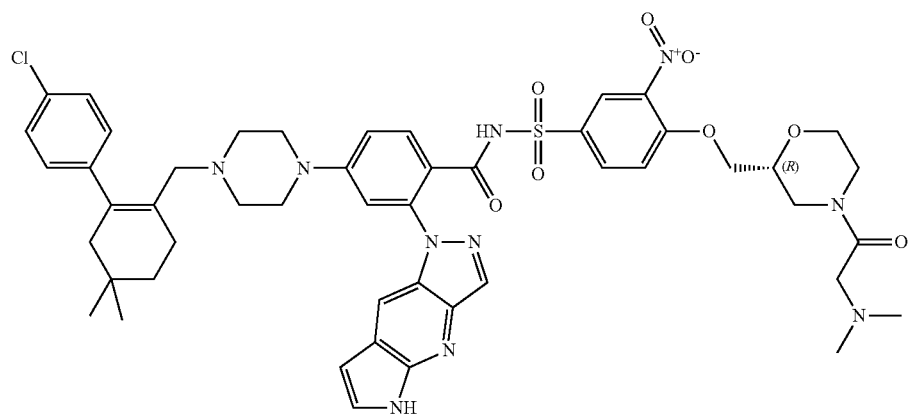

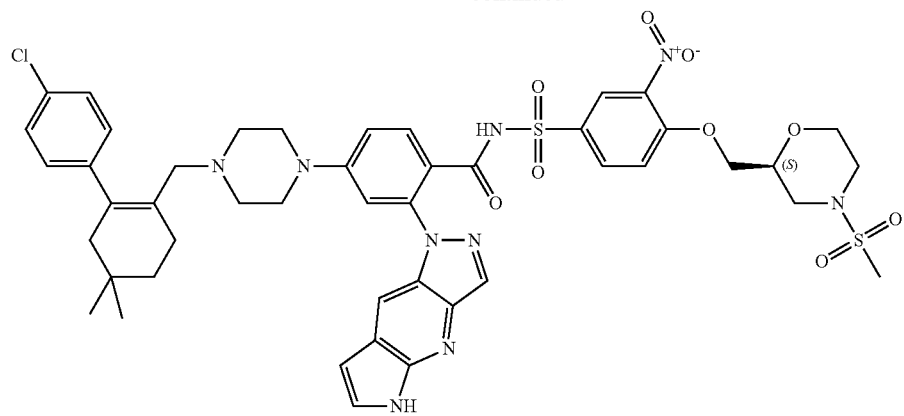
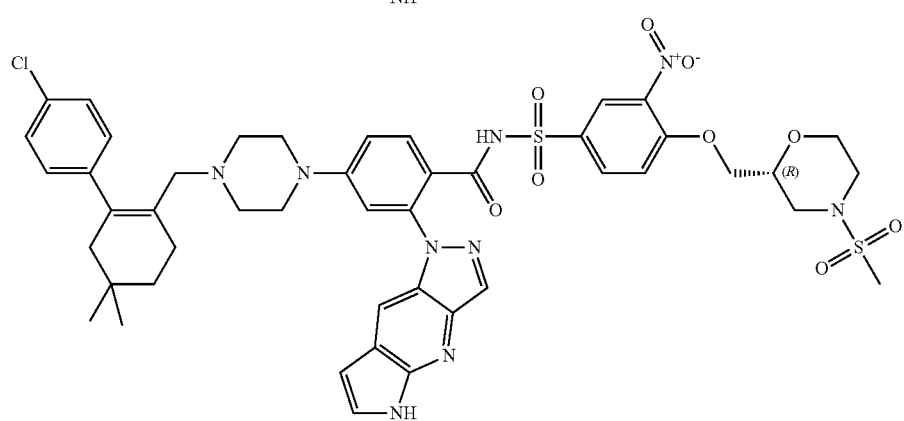
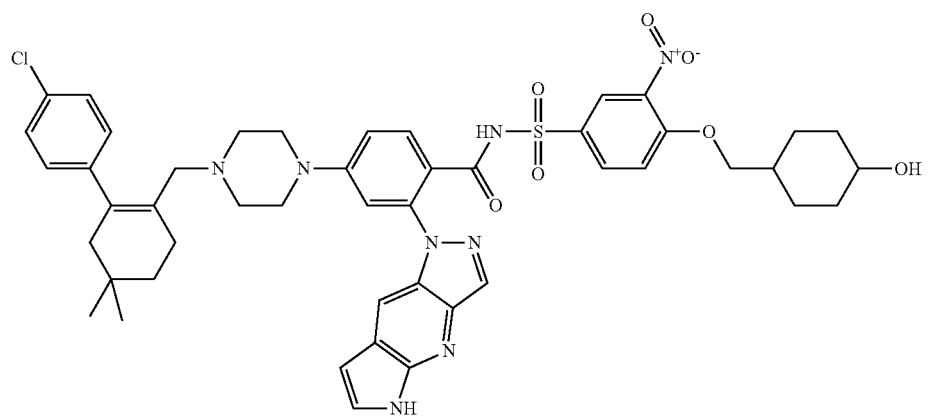
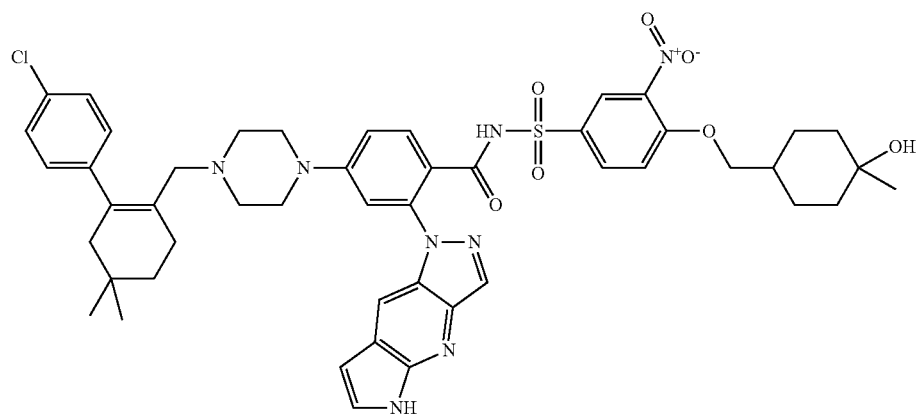

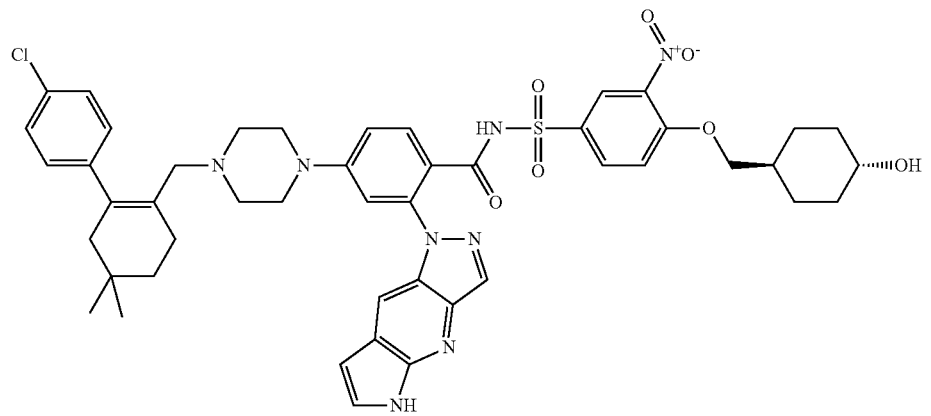
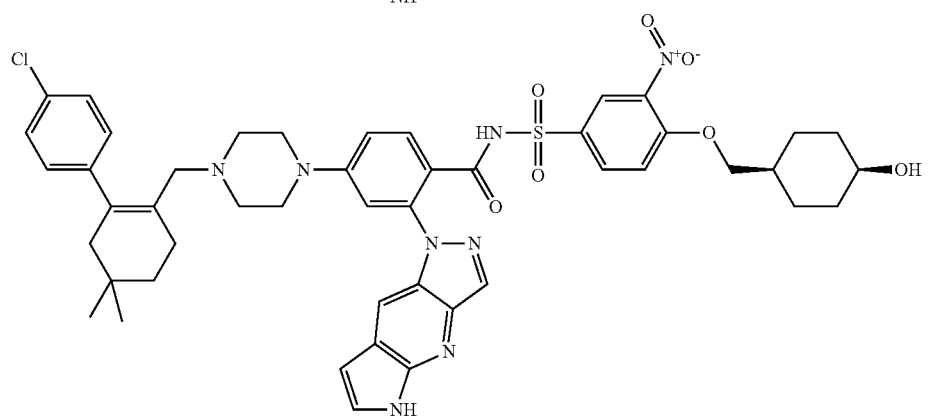
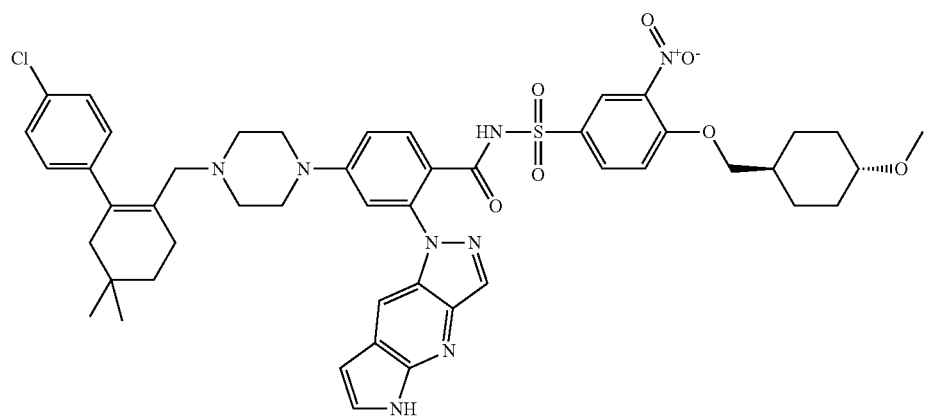
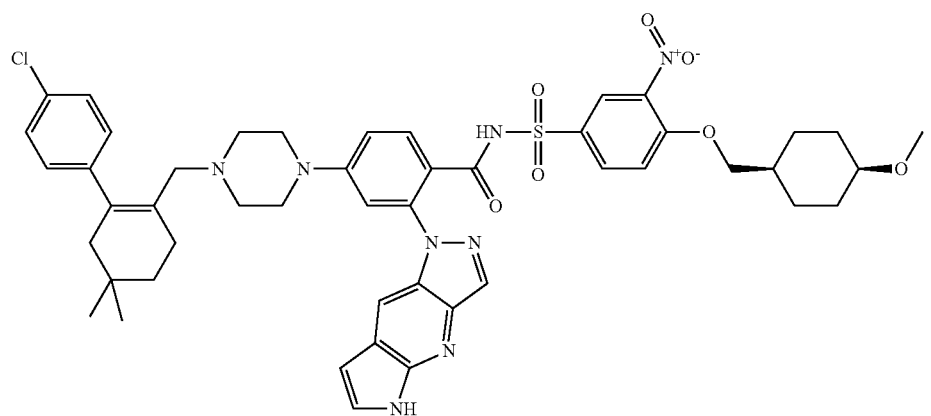

-continued
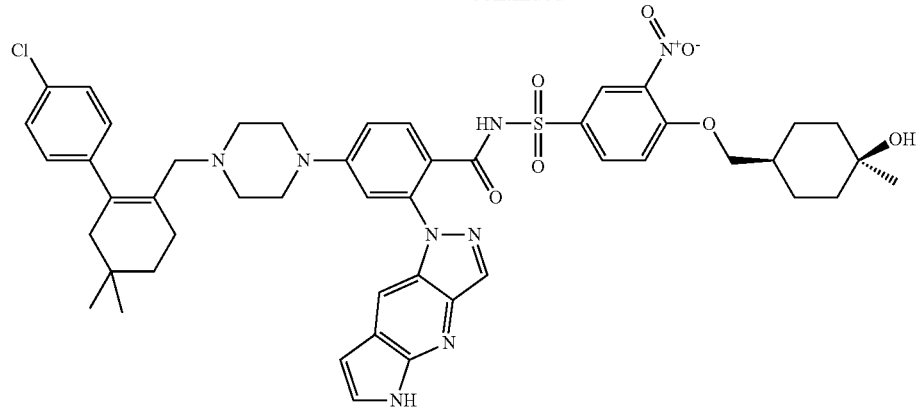
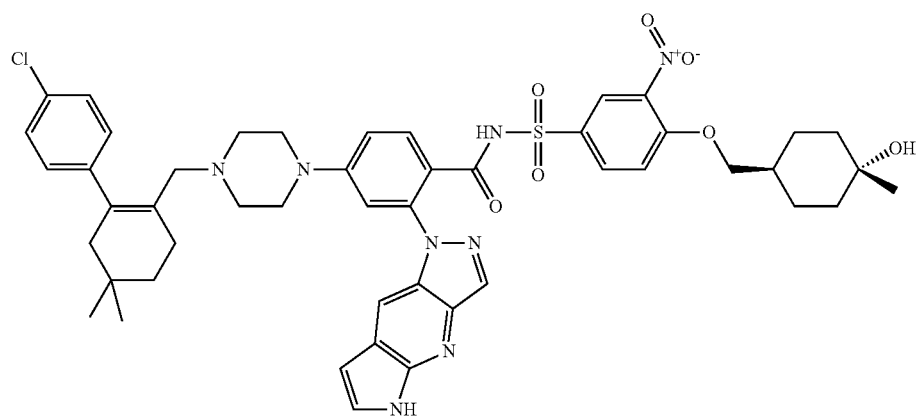
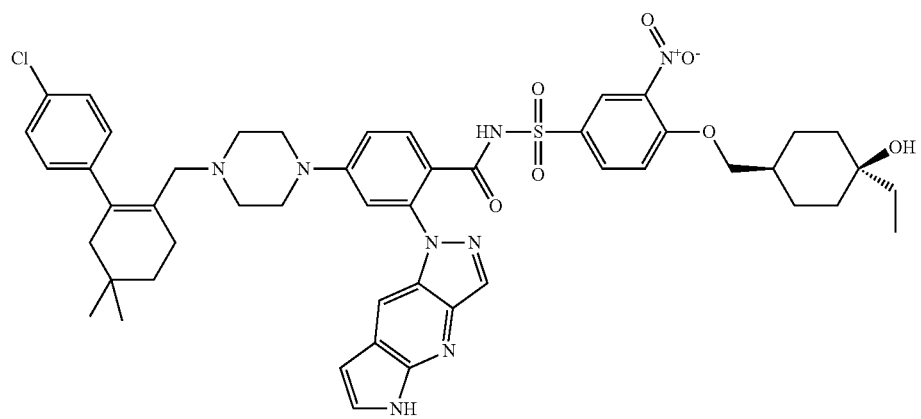
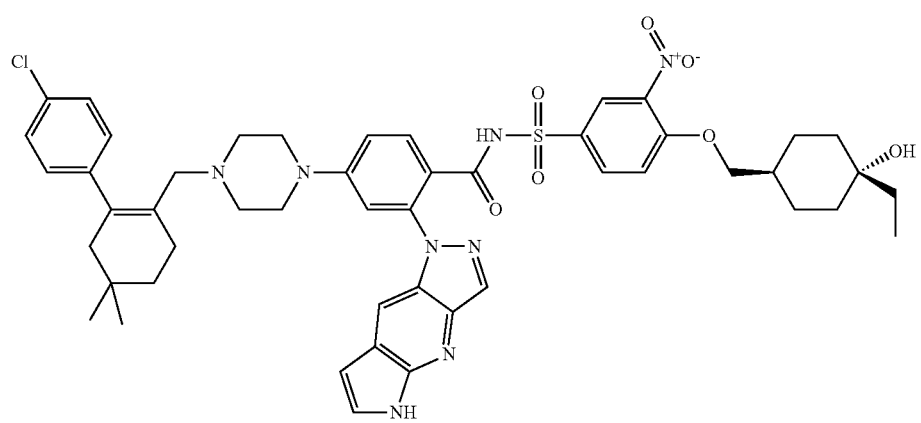

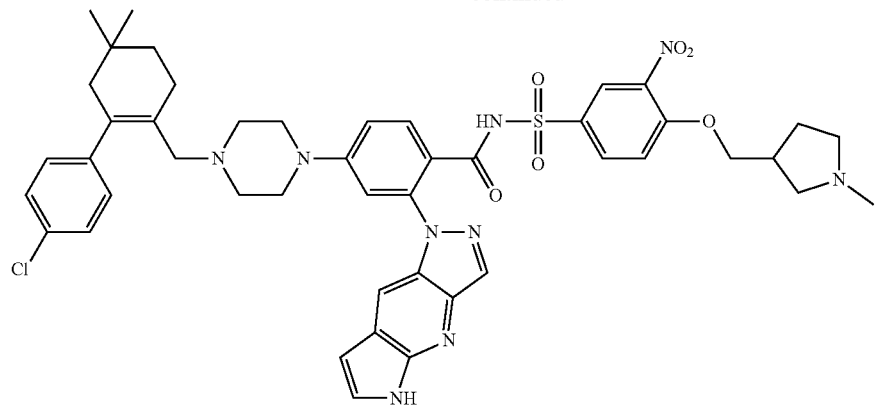
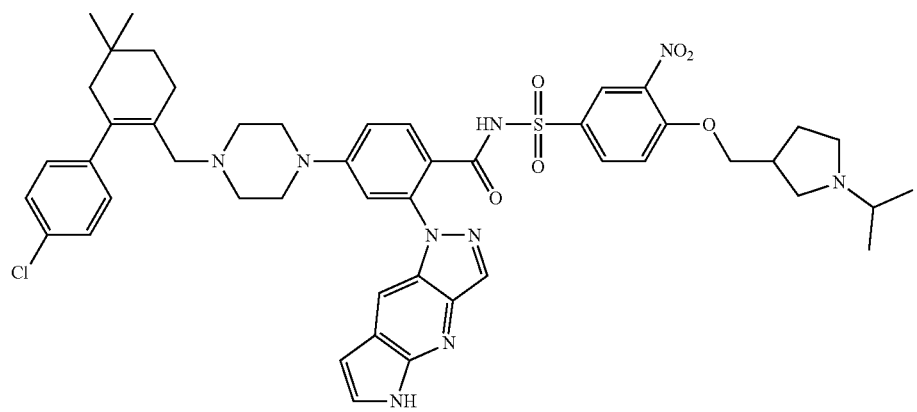
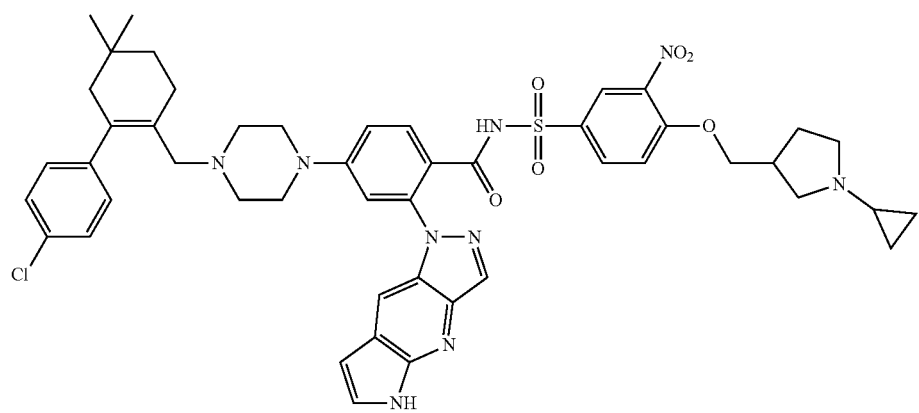
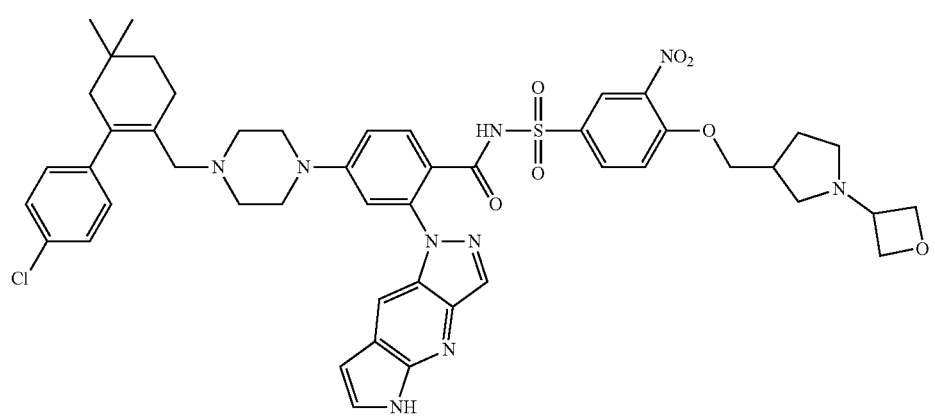

-continued
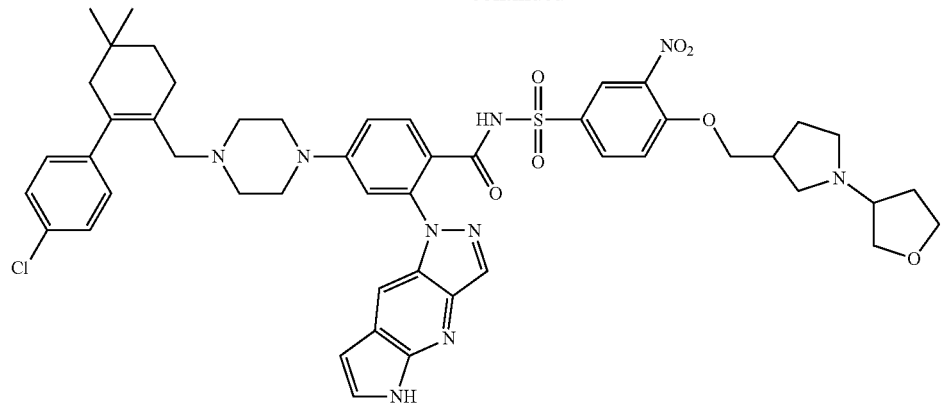
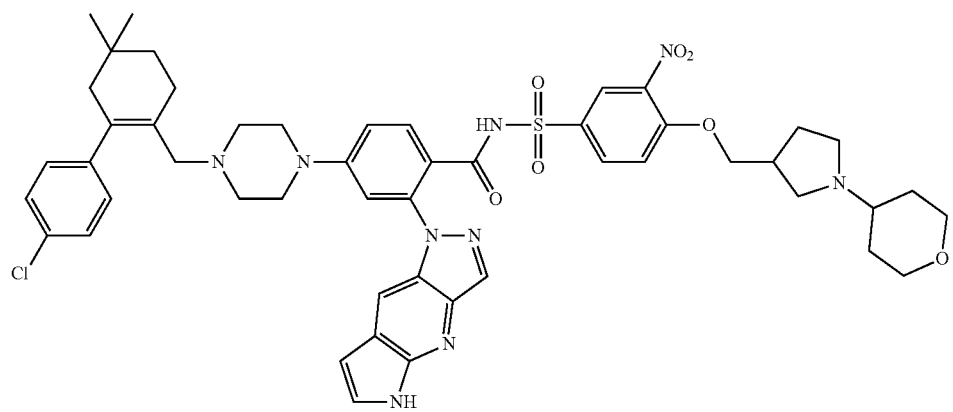
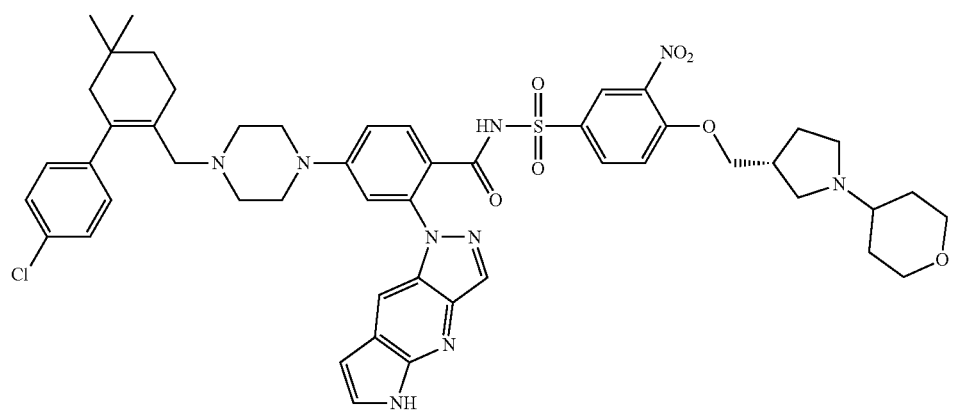
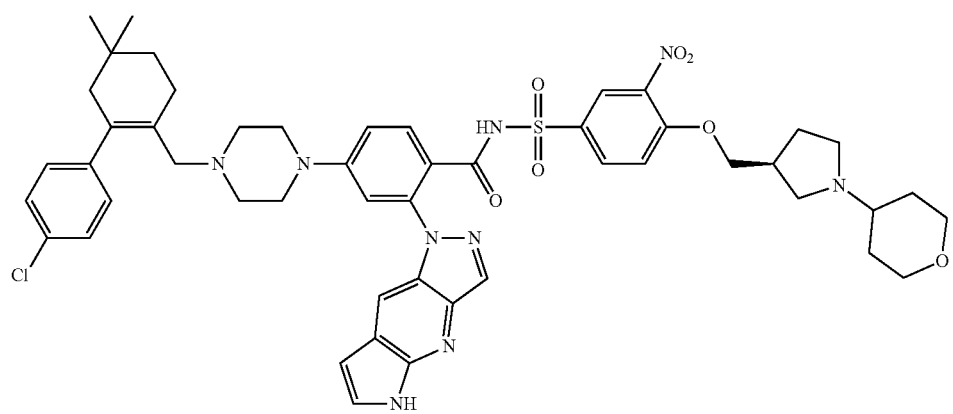

-continued
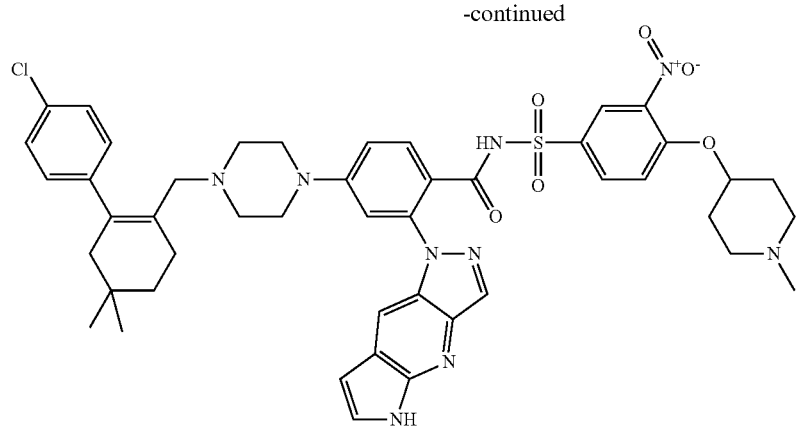
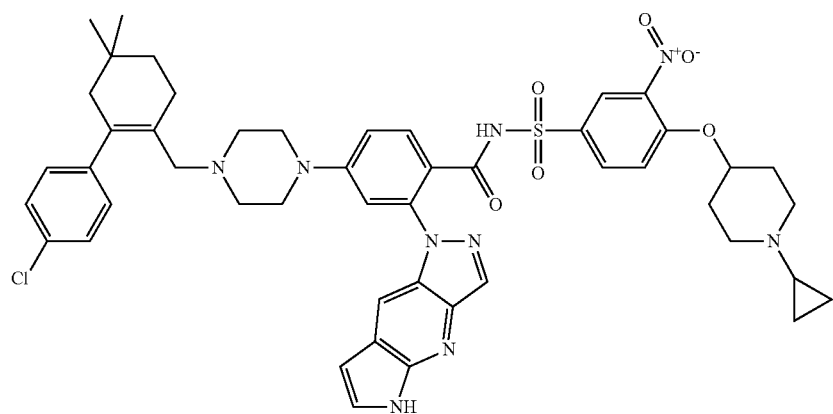
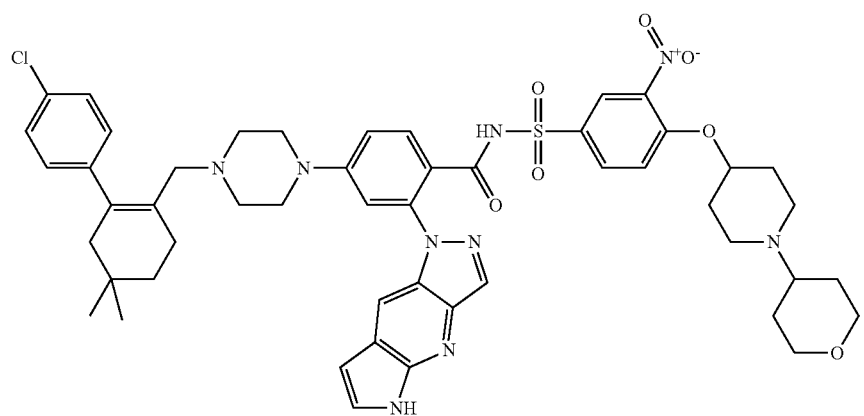
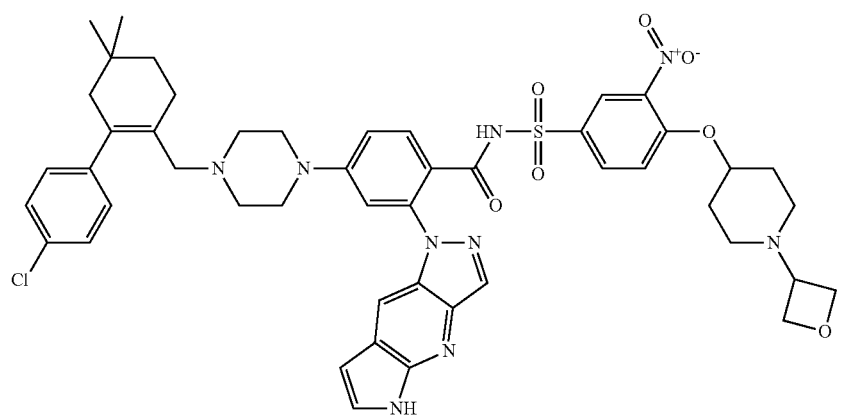

-continued
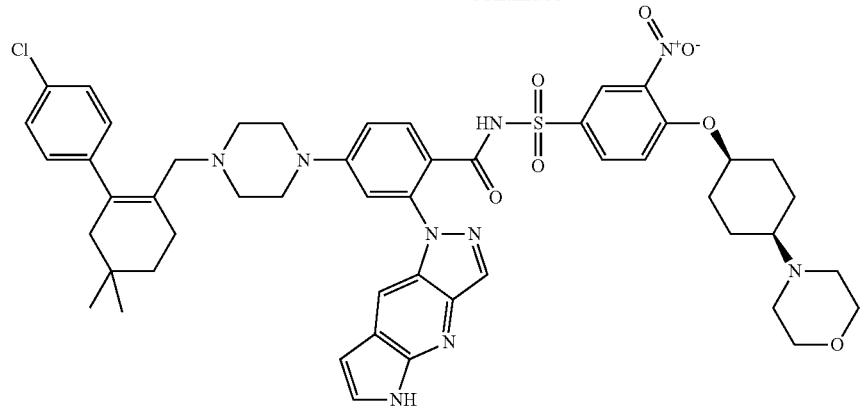
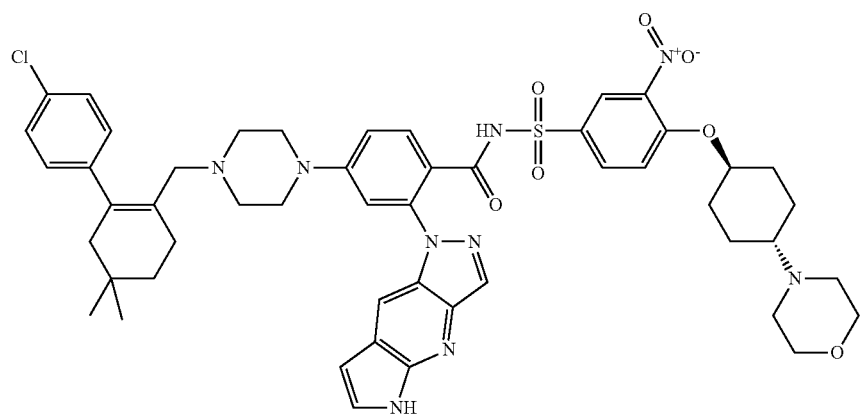
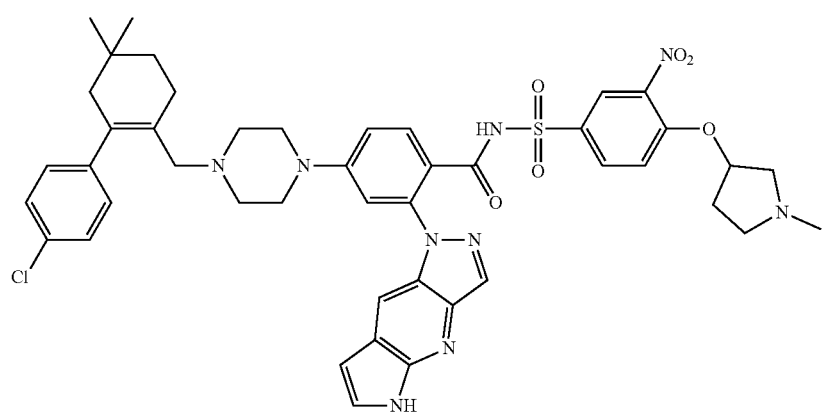
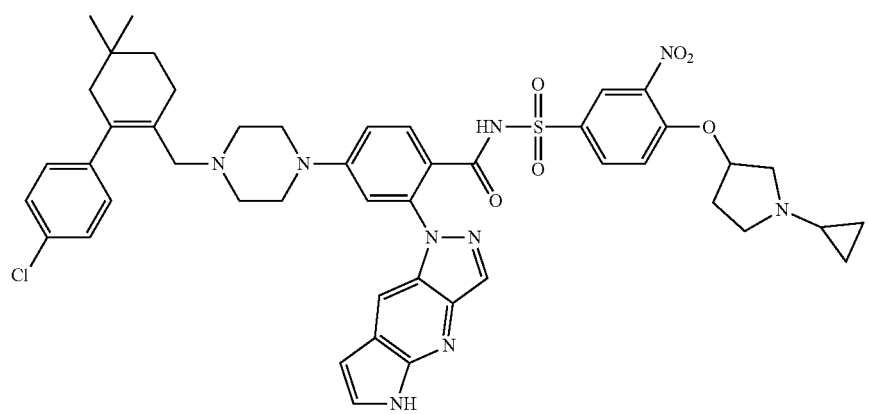

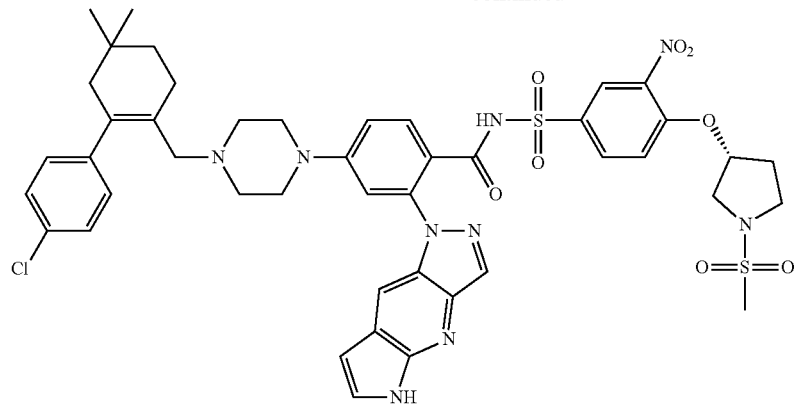
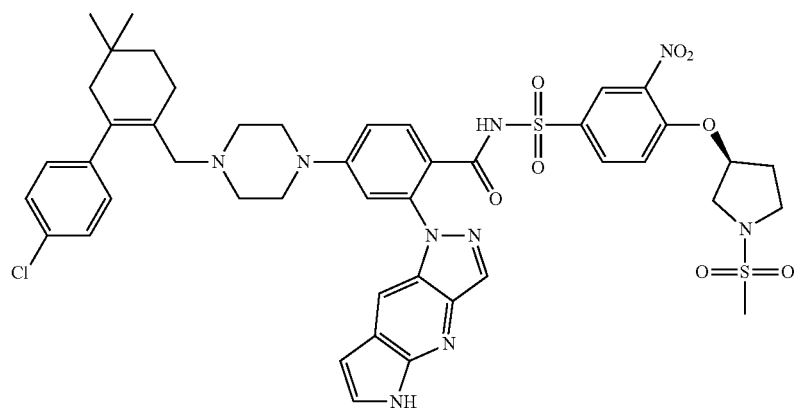
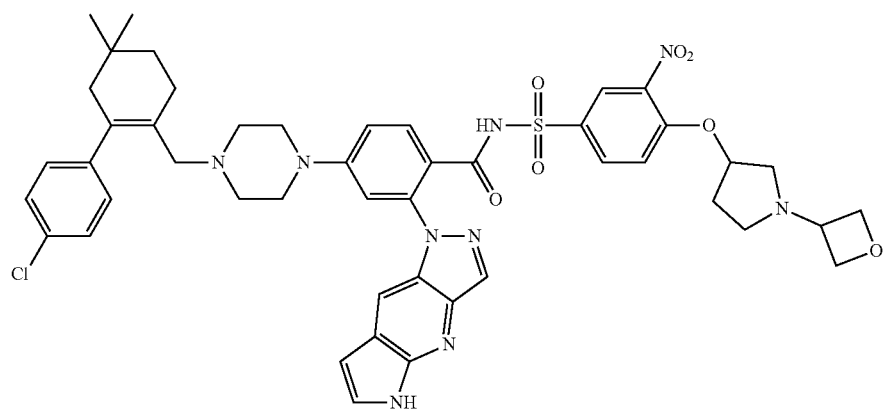
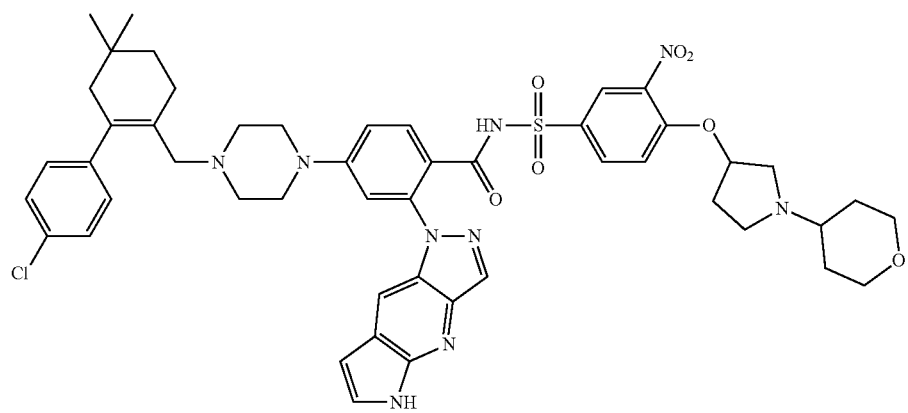

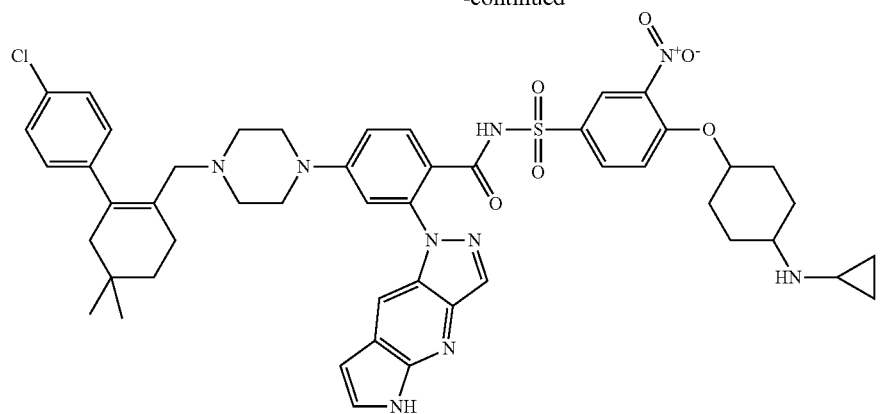
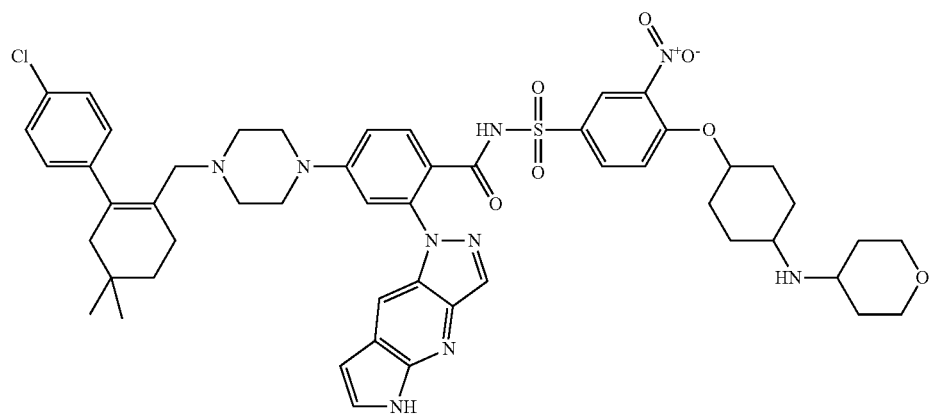
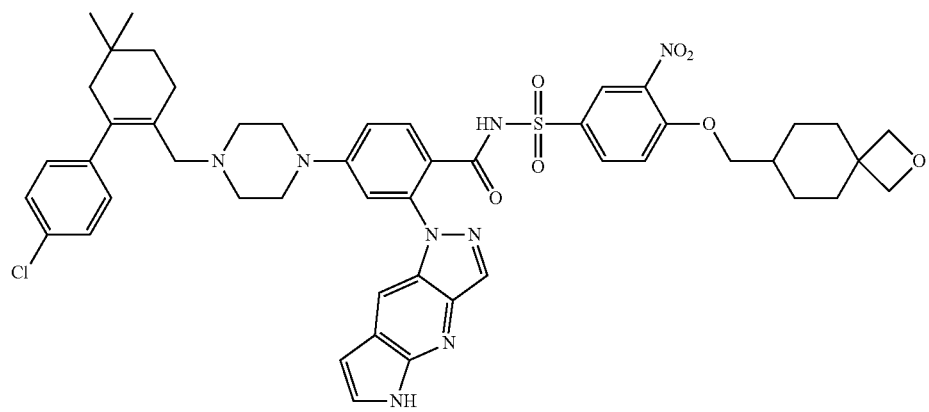
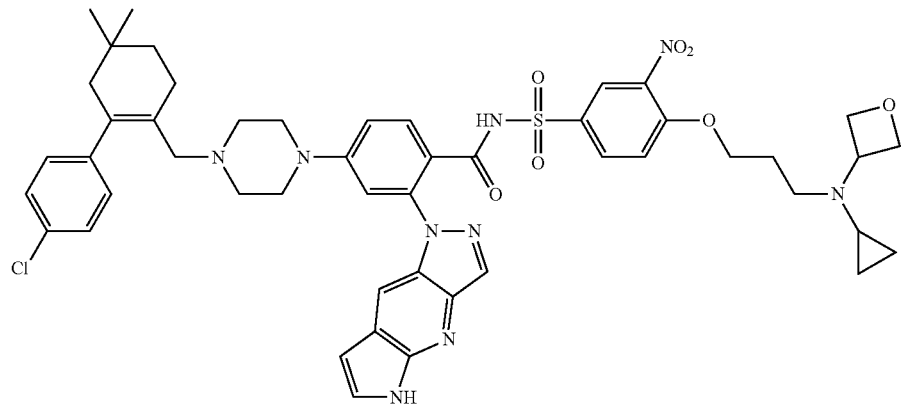

-continued
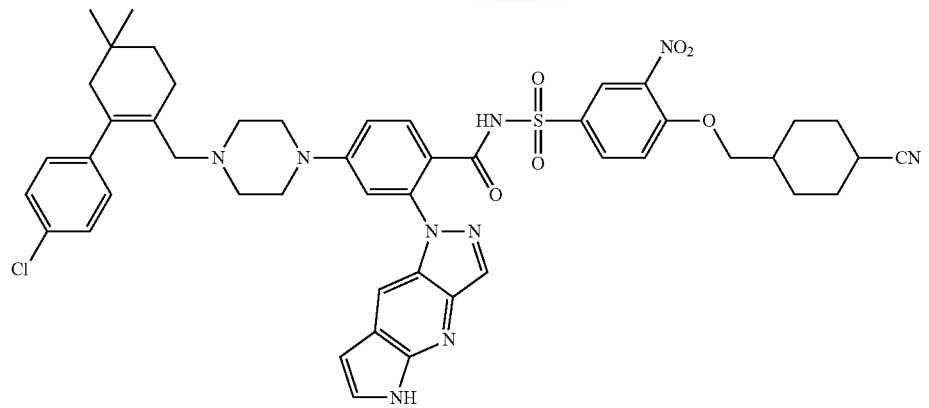
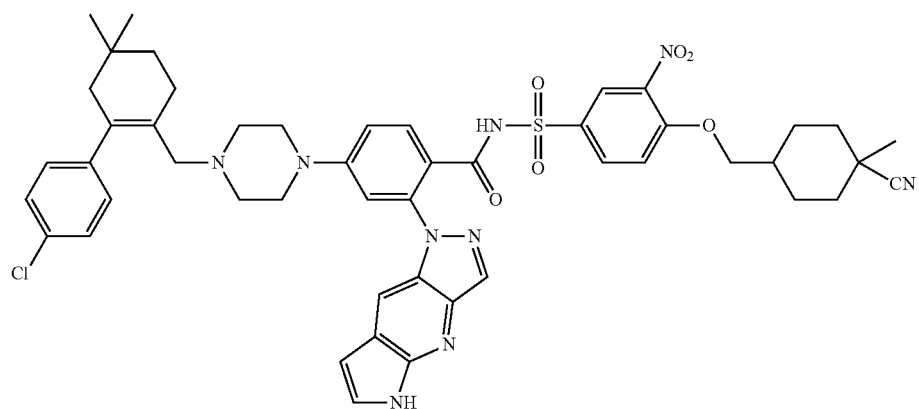
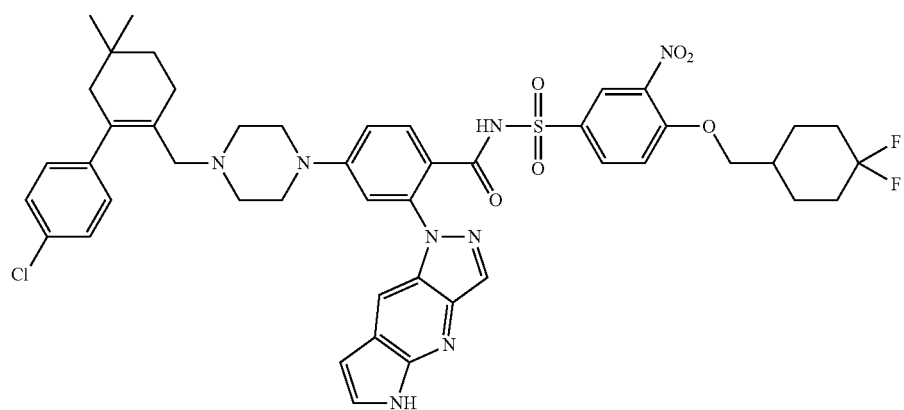
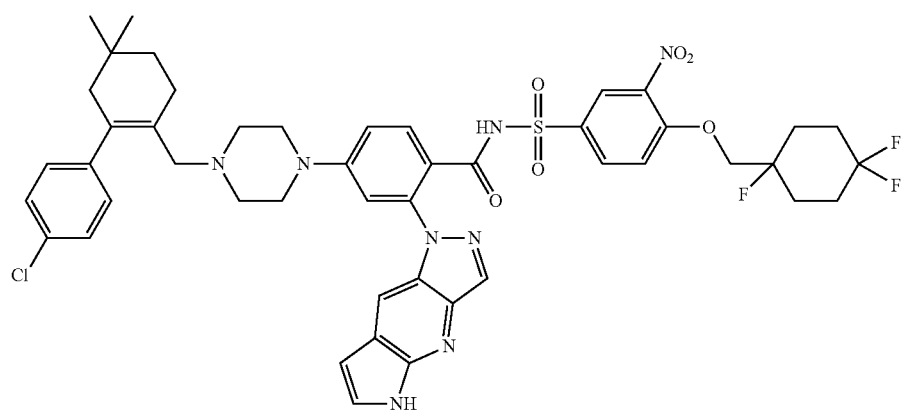

-continued
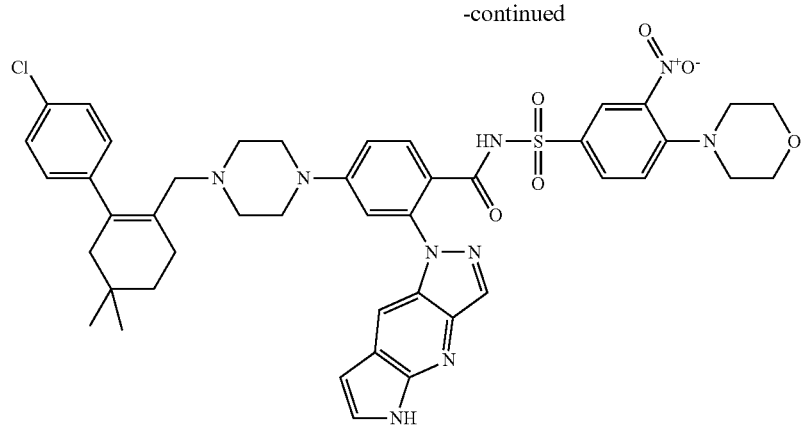
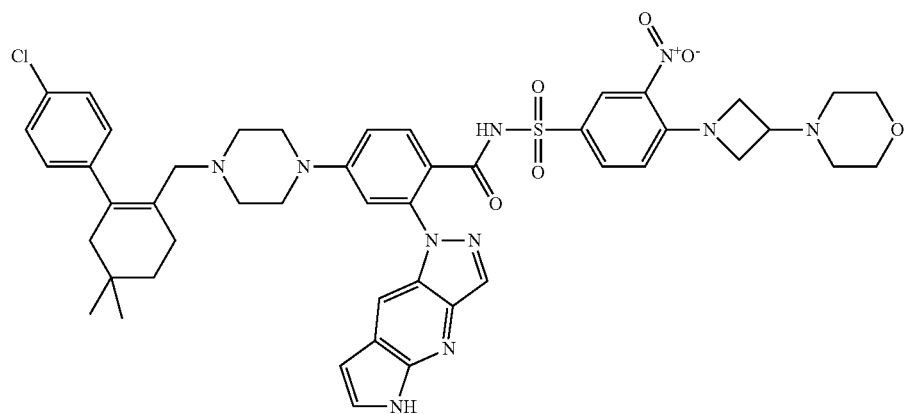
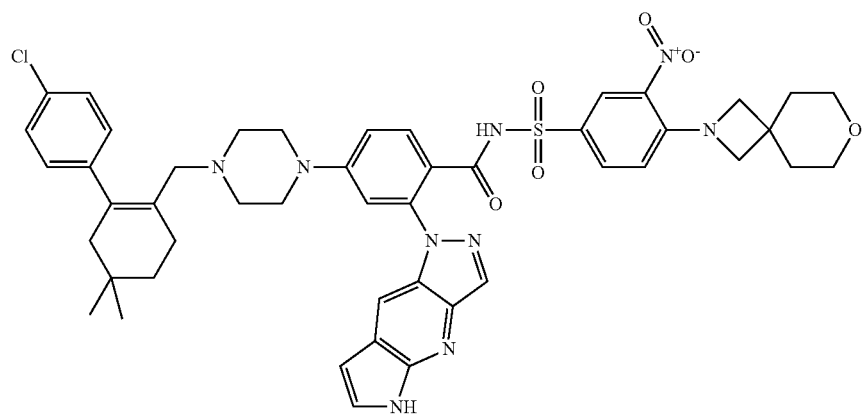
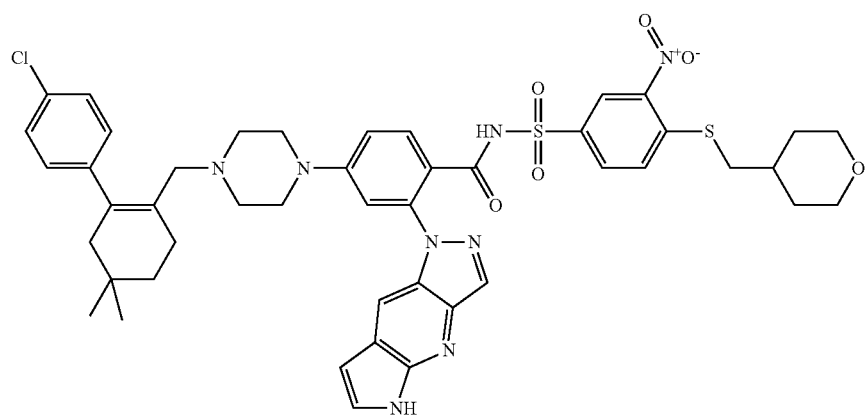

-continued
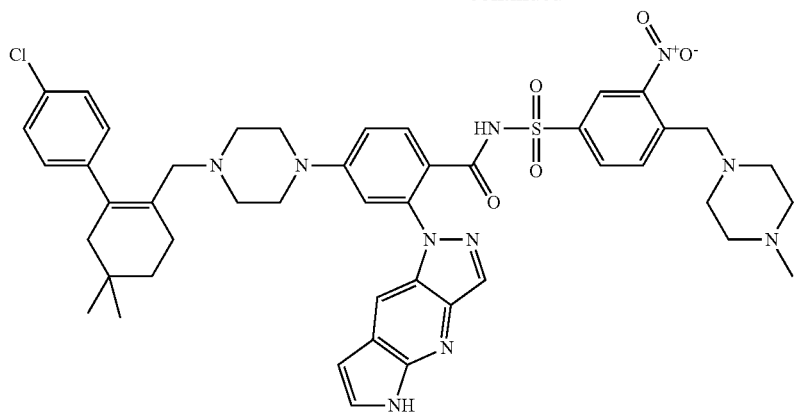
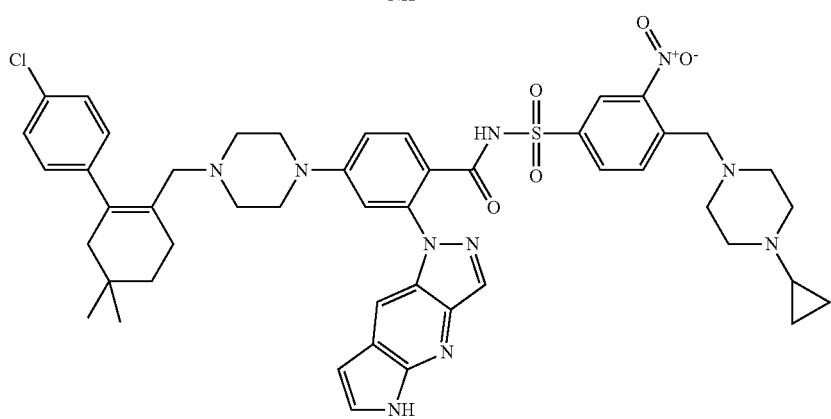
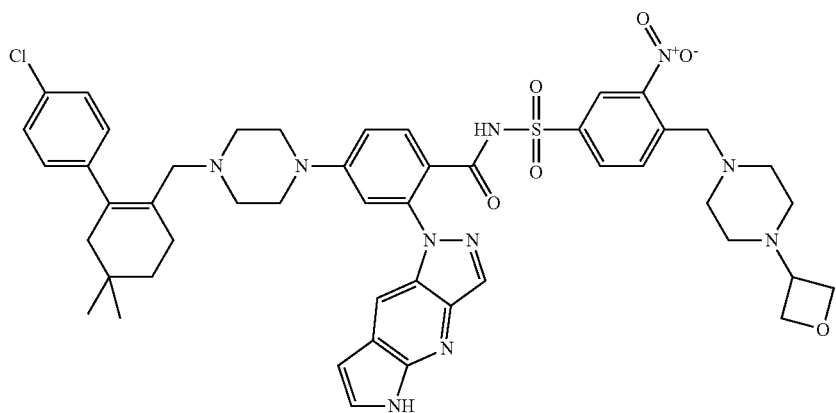
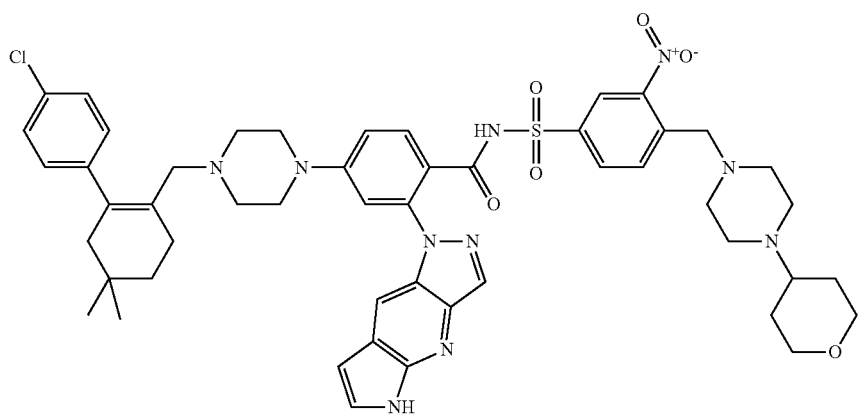

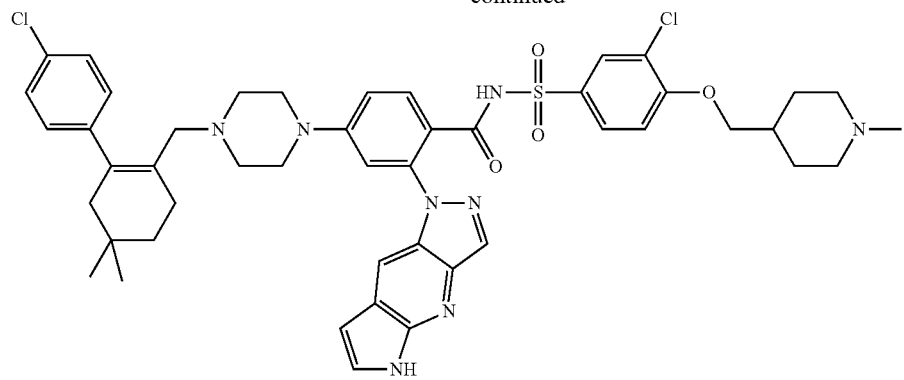
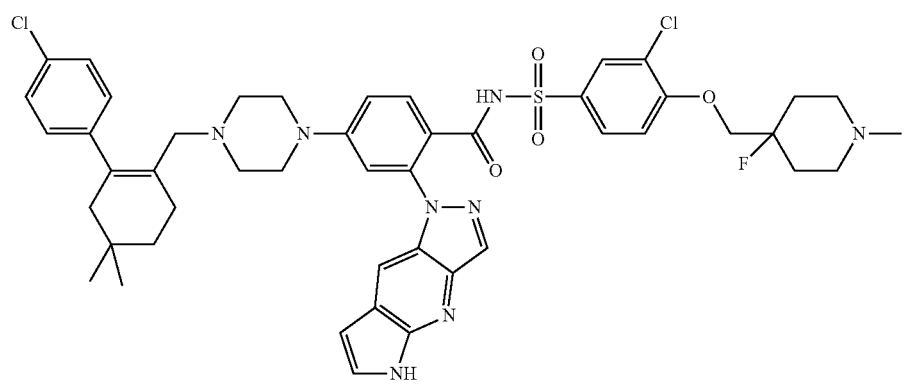
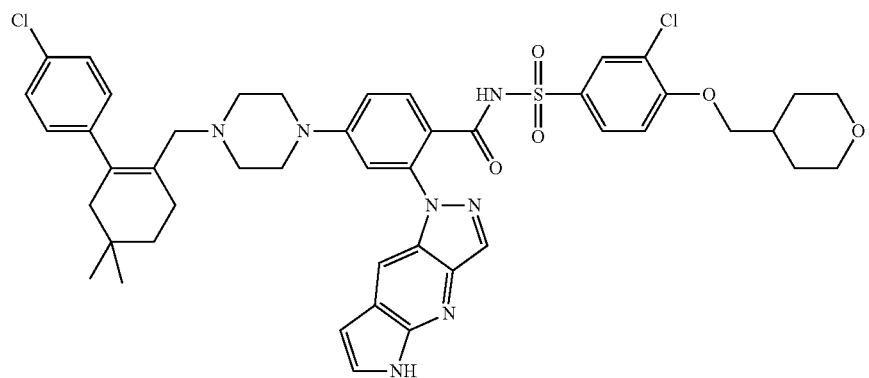
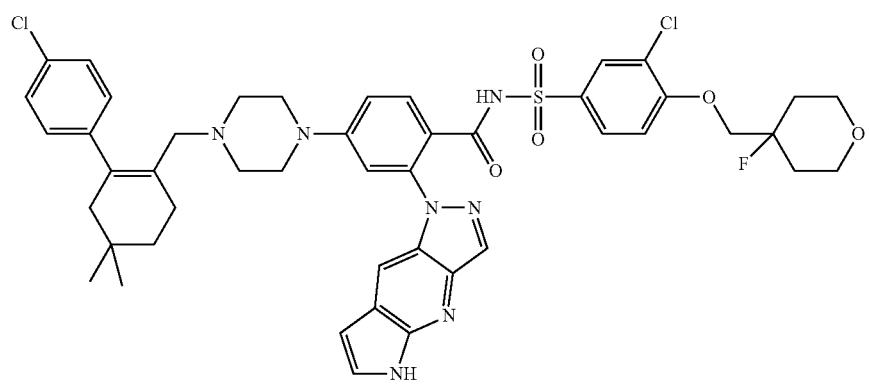

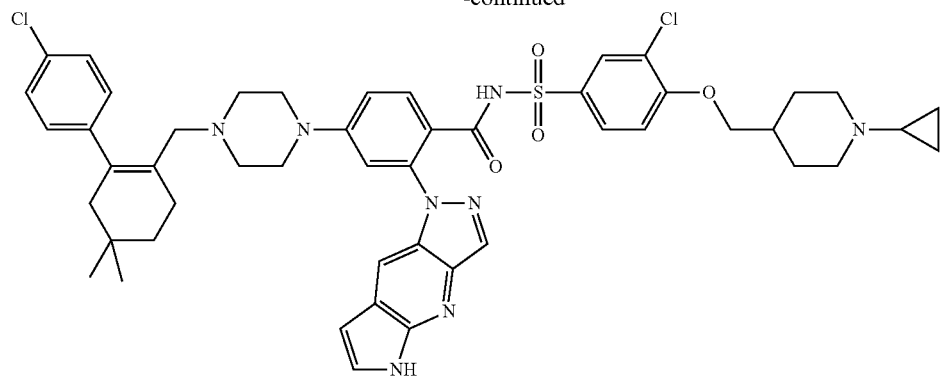
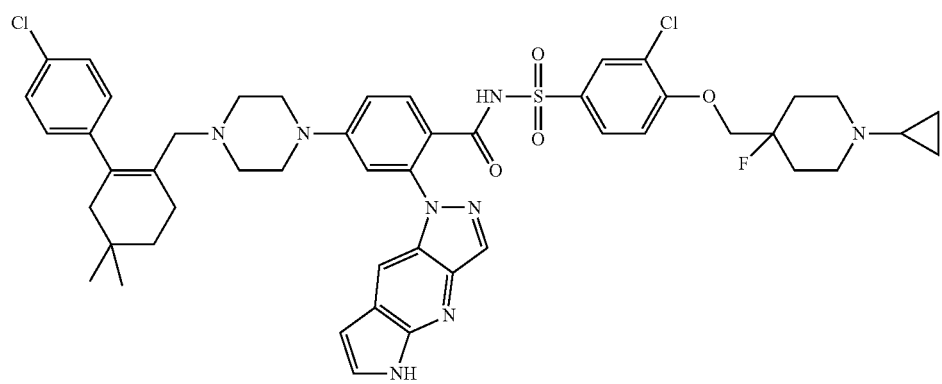
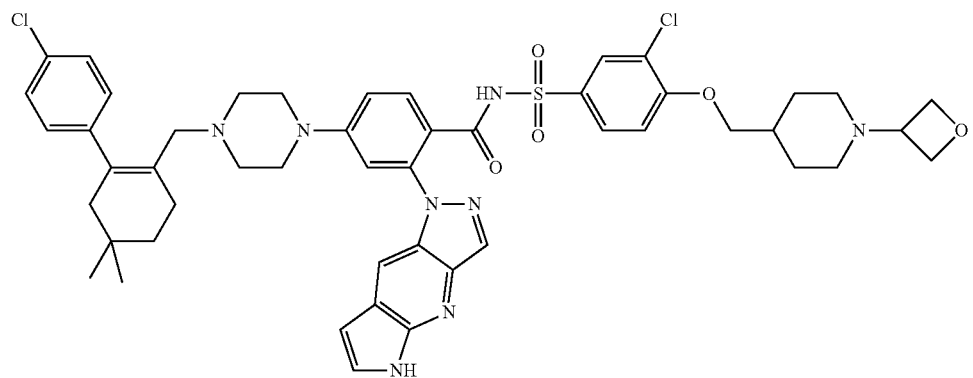
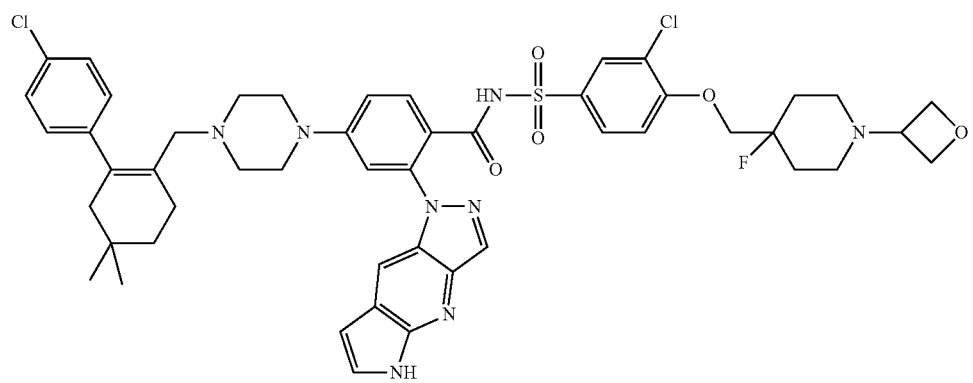

-continued
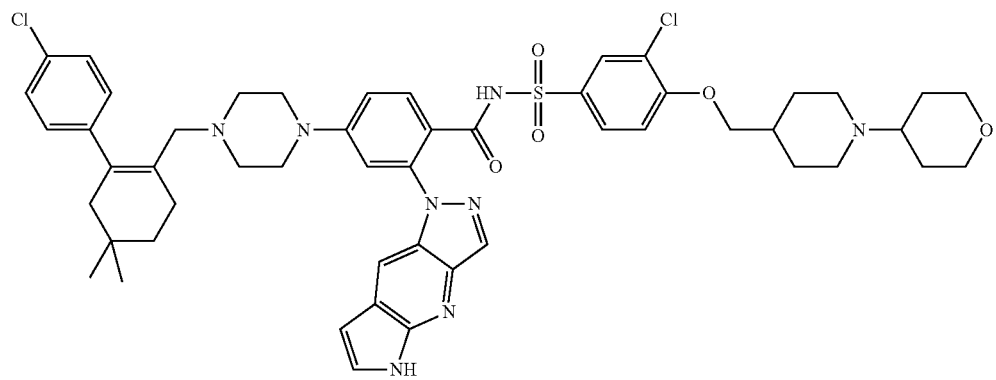
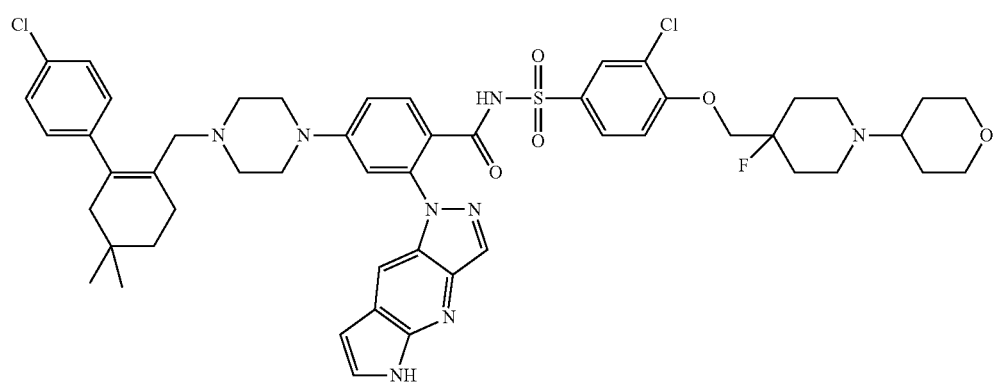
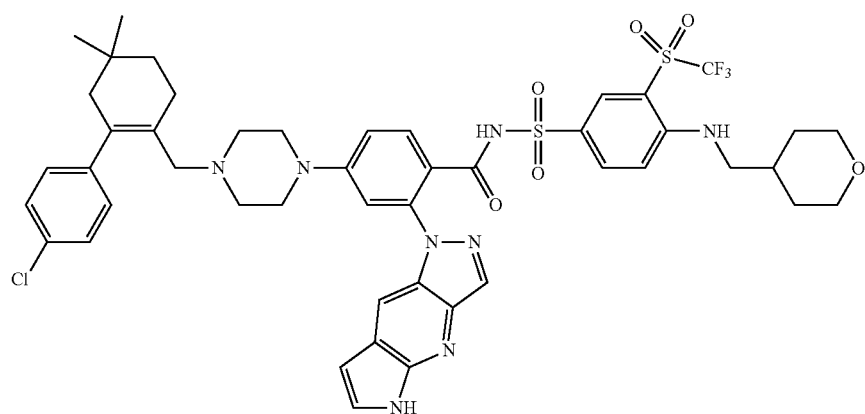
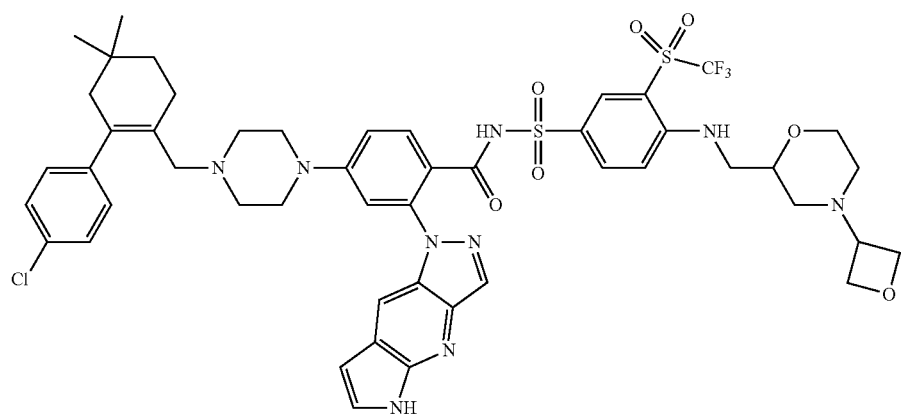

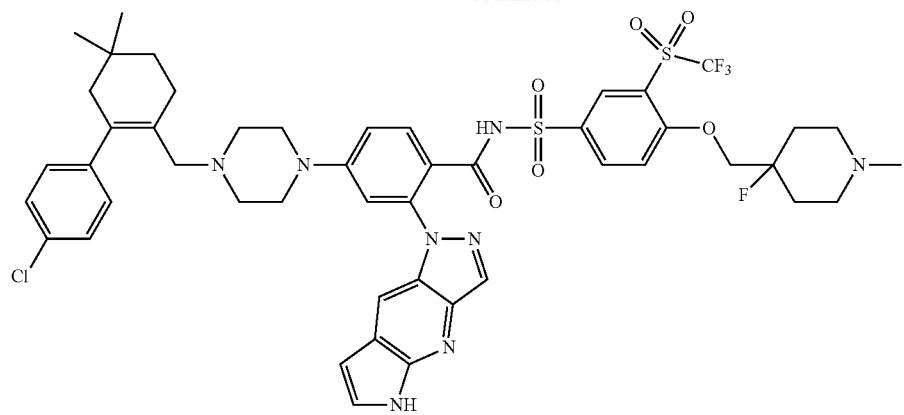
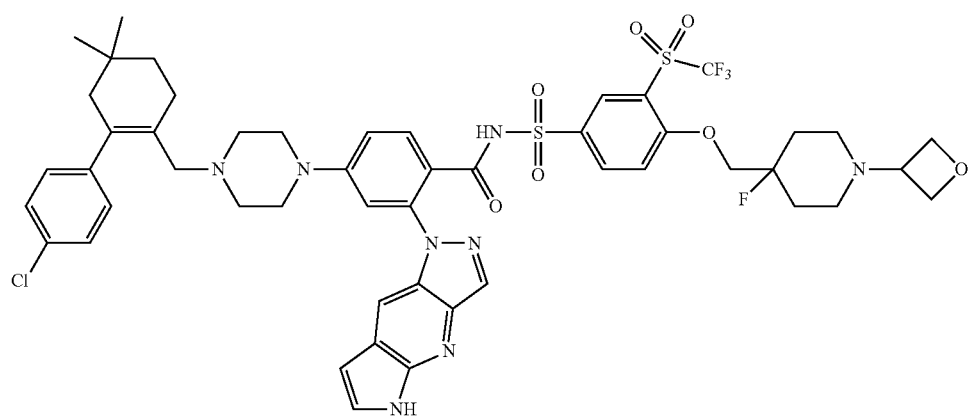
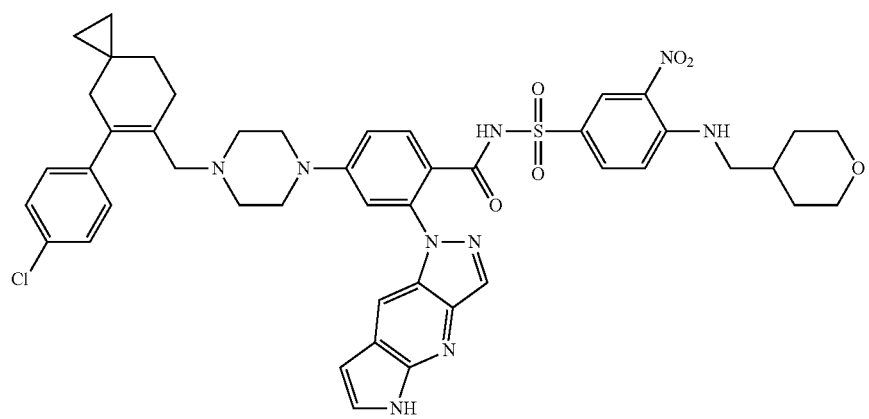
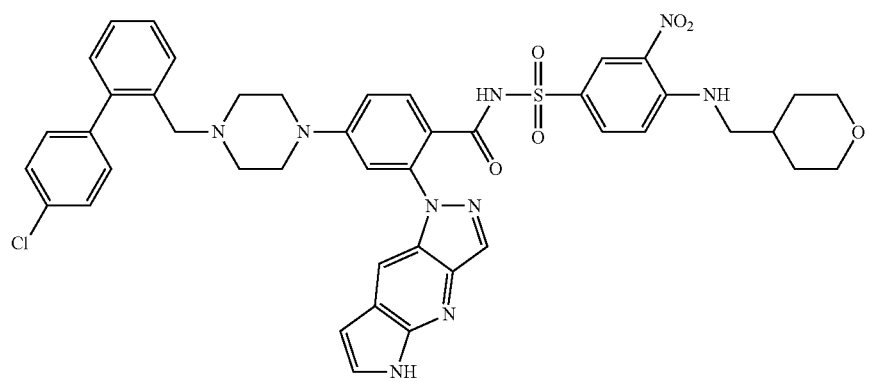

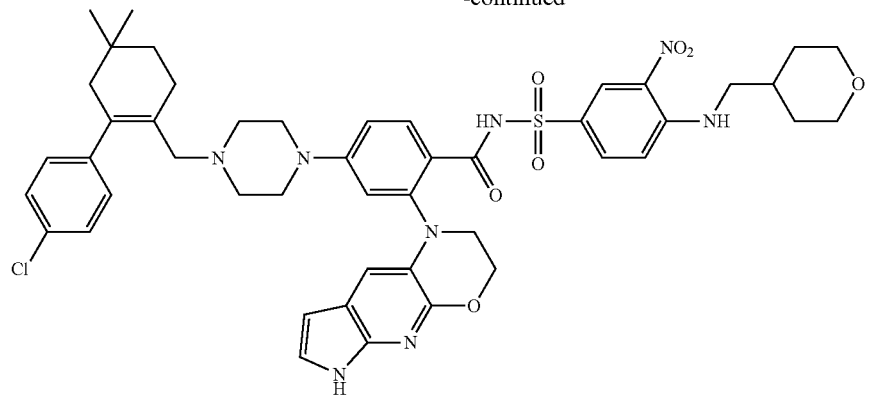

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters*, 1994, Vol. 4, p. 1985.

Deuterium-enriched compounds: deuterium (D or $^2$H) is a stable, non-radioactive isotope of hydrogen and has an atomic weight of 2.0144. Hydrogen naturally occurs as a mixture of the isotopes $^x$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide $(H_2O_2)$, Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, B, P, Si, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, B, Si, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)$NR_aR_b$ where $R_a$ and $R_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

Certain of the compounds described herein may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers, including essentially pure stereo or geometric isomers, as well as combination thereof.

It is to be understood that when a compound herein is represented by a structural formula or designated by a chemical name herein, all other tautomeric forms which may exist for the compound are encompassed by the structural formula.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure (also referred to as "enantiomerically pure"). Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g., the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), antimicrotubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK (A1/B1/G1), AMPK (A1/B1/G2), AMPK (A1/B1/G3), AMPK (A1/B2/G1), AMPK (A2/B1/G1), AMPK (A2/B2/G1), AMPK (A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CSF1R, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg (p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1 (E255K), ABL1 (F317I), ABL1 (G250E), ABL1 (H396P), ABL1 (M351T), ABL1 (Q252H), ABL1 (T315I), ABL1 (Y253F), ALK (C1156Y), ALK (L1196M), ALK (F1174L), ALK (R1275Q), BRAF (V599E), BTK (E41K), CHK2 (I157T), c-Kit (A829P), c-KIT (D816H), c-KIT (D816V), c-Kit (D820E), c-Kit (N822K), C-Kit (T670I), c-Kit (V559D), c-Kit (V559D/V654A), c-Kit (V559D/T670I), C-Kit (V560G), c-KIT (V654A), C-MET (D1228H), C-MET (D1228N), C-MET (F1200I), c-MET (M1250T), C-MET (Y1230A), C-MET (Y1230C), C-MET (Y1230D), C-MET (Y1230H), c-Src (T341M), EGFR (G719C), EGFR (G719S), EGFR (L858R), EGFR (L861Q), EGFR (T790M), EGFR, (L858R,T790M), EGFR (d746-750/T790M), EGFR (d746-750), EGFR (d747-749/A750P), EGFR (d747-752/P753S), EGFR (d752-759), FGFR1 (V561M), FGFR2 (N549H), FGFR3 (G697C), FGFR3 (K650E), FGFR3 (K650M), FGFR4 (N535K), FGFR4 (V550E), FGFR4 (V550L), FLT3 (D835Y), FLT3 (ITD), JAK2 (V617F), LRRK2 (G2019S), LRRK2 (I2020T), LRRK2 (R1441C), p38a (T106M), PDGFRa (D842V), PDGFRa (T674I), PDGFRa (V561D), RET (E762Q), RET (G691S), RET (M918T), RET (R749T), RET (R813Q), RET (V804L), RET (V804M), RET (Y791F), TIF2 (R849W), TIF2 (Y897S), and TIF2 (Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc), and other immunotherapies (e.g anti-PD1, anti-PDL1, anti-CTLA4, A2A antagonist etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

The invention further provides methods for the prevention or treatment of a neoplastic disease or autoimmune disease. In one embodiment, the invention relates to a method of treating a neoplastic disease or autoimmune disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease or autoimmune disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

The autoimmune diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barré syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of the intermediate

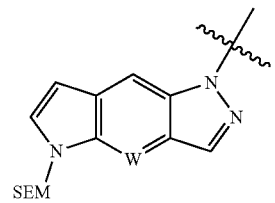

in which W is N is described in Scheme 1. The intermediate with N is CH can be made similarly.

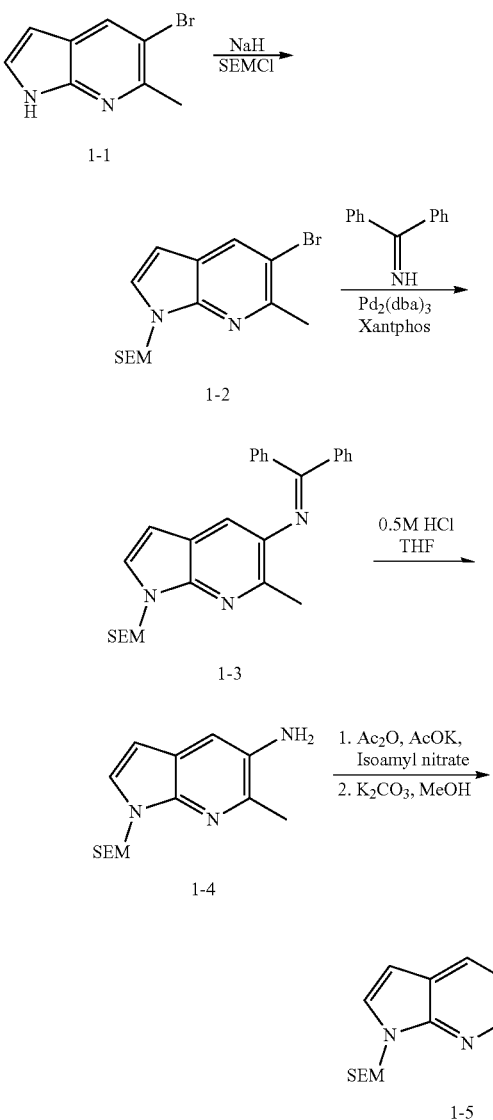

In Scheme 1, the starting material 1-1 is protected with SEM group to give intermediate 1-2, which is followed by Buckwald coupling to yield intermediate 1-3. Hydrolysis of imine 1-3 gives aniline intermediate 1-4. Condensation of 1-4 with acetic acid anhydride results in SEM-protected tricyclic intermediate 1-5.

A typical approach to synthesize of the intermediate

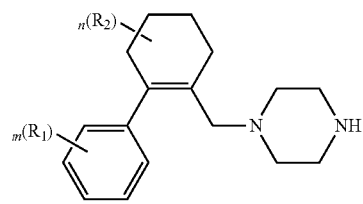

is described in Scheme 2:

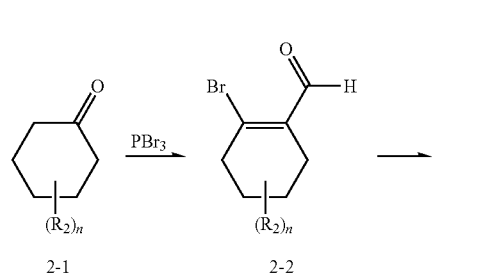

2-1     2-2

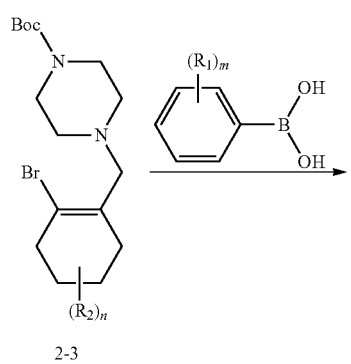

2-3

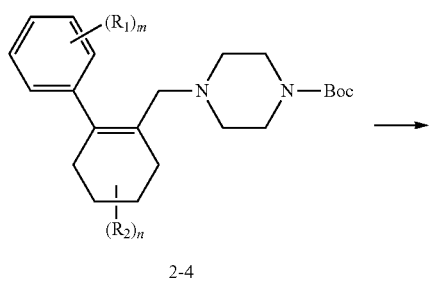

2-4

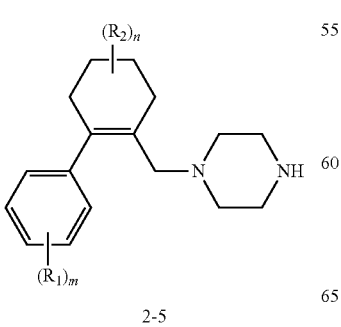

2-5

In Scheme 2, the appropriate ketone starting material 2-1 can react with tribromophosphine to form the aldehyde intermediate 2-2, which can couple with Boc-protected piperazine to form the intermediate 2-3. After that, 2-3 will couple with appropriate phenylboronic acid via a Suzuki reaction to form intermediate 2-4, followed by a de-boc process to yield key intermediate 2-5.

A typical approach to synthesize of the intermediate

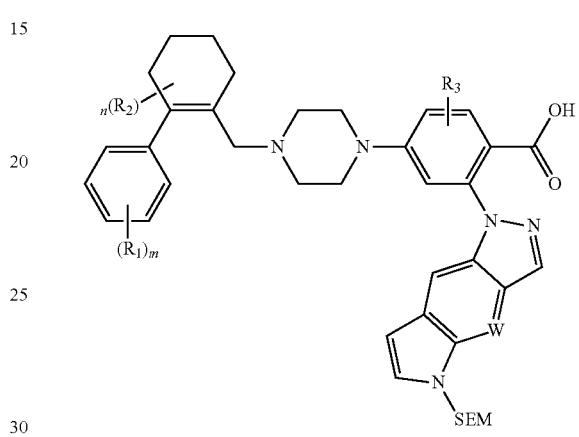

is described in Scheme 3:

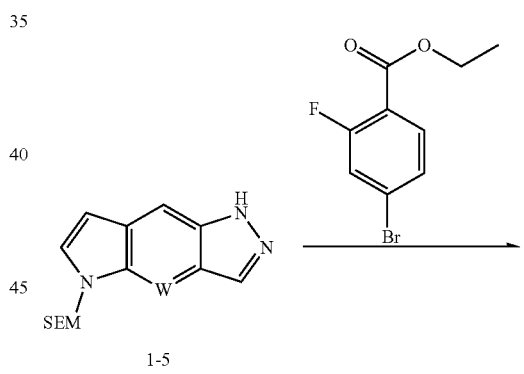

1-5

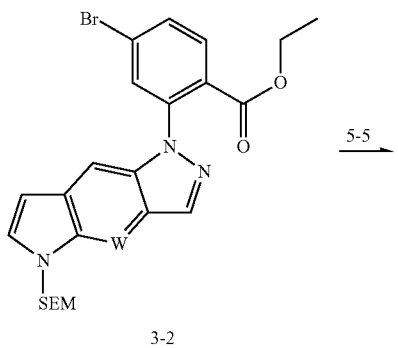

3-2

-continued

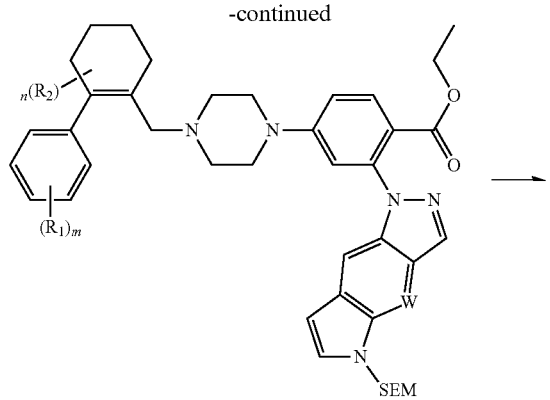

3-3

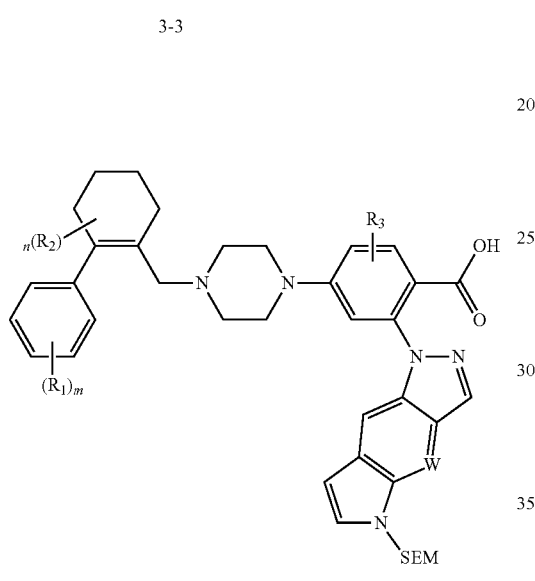

3-4

In Scheme 3, the staring intermediate 1-5 reacts with ethyl 4-Br-2-F-benzoic ester under basic conditions to give 3-2. Buckwald coupling or nucleophilic substitution reactions between 3-2 and 5-5 produces intermediate 3-3. Hydrolysis of 3-3 gives intermediate 3-4.

A typical approach to synthesize of the intermediate

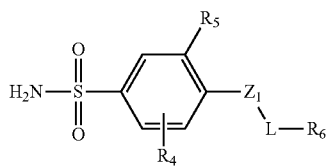

in which $R_5$ is $NO_2$ is described in Scheme 4:

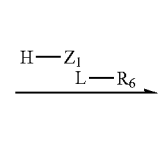

4-1

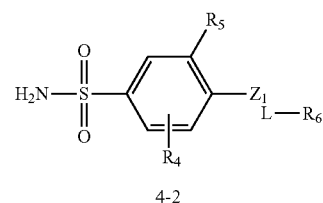

4-2

In Scheme 4, the staring intermediate 4-1 reacts with appropriate alcohol or amine will yield 4-2.

A typical approach to synthesize of the Formula (I) compounds with $Z_1$=NH or O is described in Scheme A:

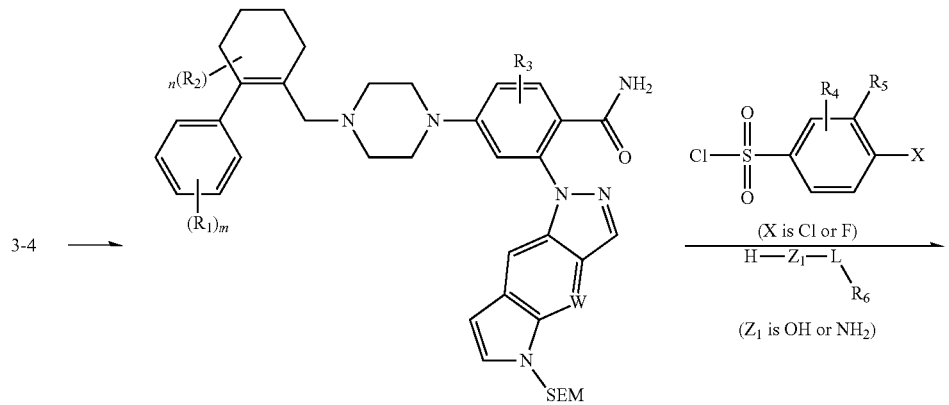

A-2

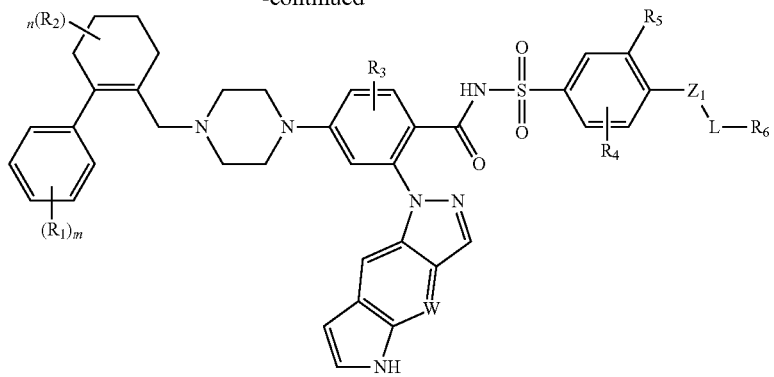

Formula (I)

The intermediate 3-4 can undergo an amide coupling with ammonia gives intermediate A-2. Sequential substitution reaction of chlorobenzene sulfonyl halides (X is Cl or F) with appropriate amine $NH_2LR_4$ or alcohol $HO-L-R_4$ and coupling reaction with intermediate A-2 followed by deprotection of SEM group leads to Formula (I).

Similarly, a typical approach to synthesize of the Formula (I) compounds is described in Scheme B:

In Scheme B, The intermediate 3-4 can undergo an amide coupling with ammonia gives intermediate A-2. After that, the substitution reaction of appropriate sulfonyl chloride followed by deprotection of SEM group leads to final product Formula (I).

Similarly, a typical approach to synthesize of the Formula (I) compounds is described in Scheme C:

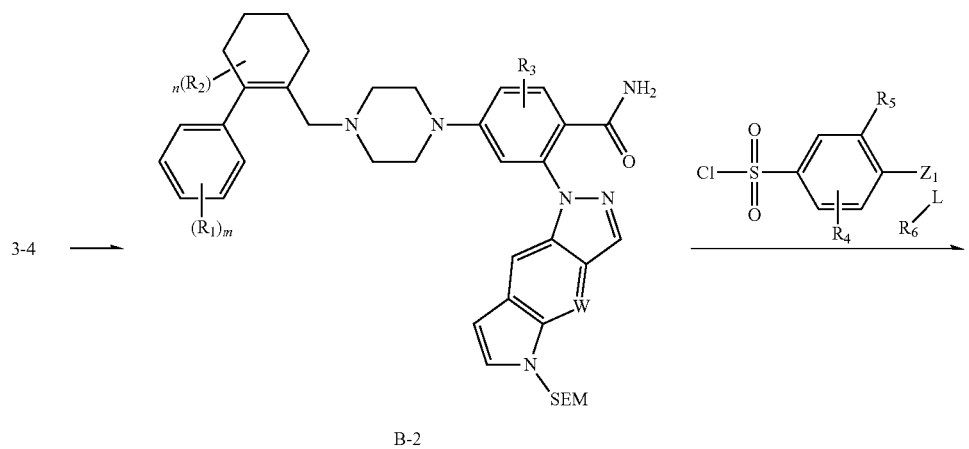

B-2

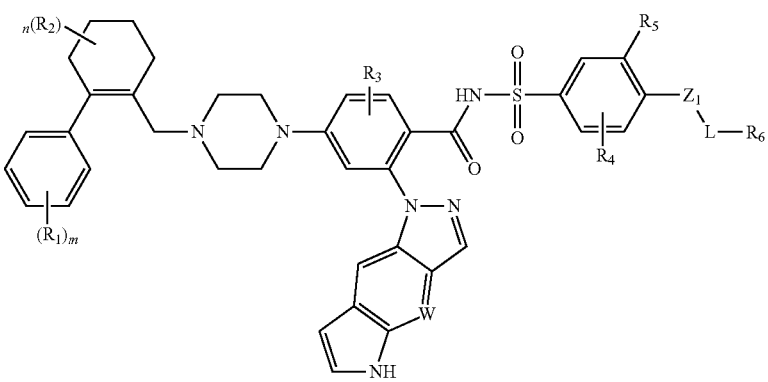

Formula (I)

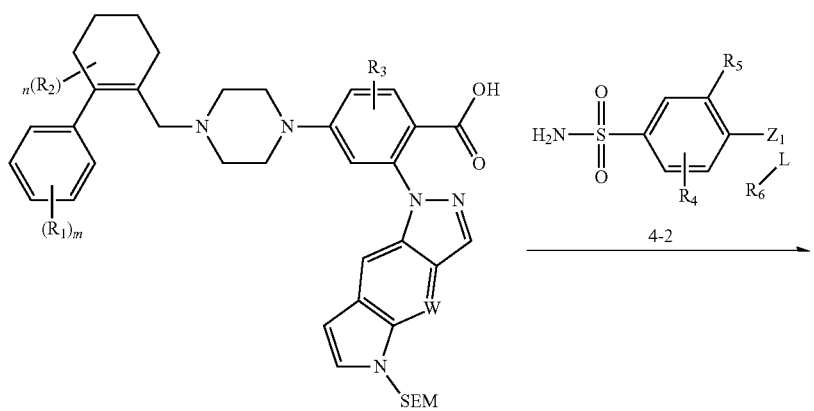

3-4

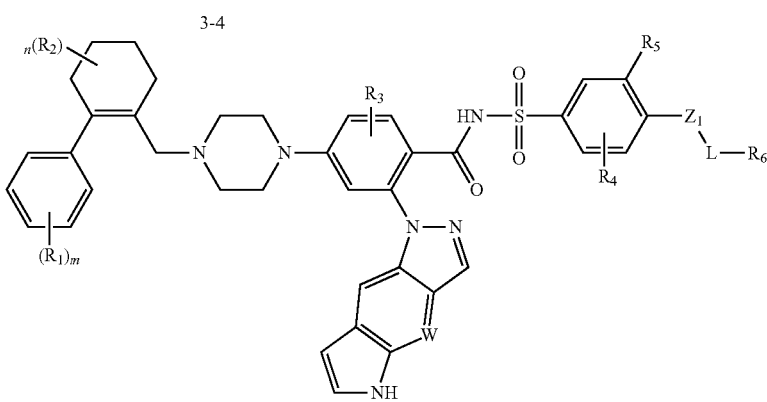

Formula (I)

In Scheme C, the amide coupling of 3-4 and 4-2 leads to final product Formula (I).

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example 1: Preparation of Key Intermediate IM-14-1

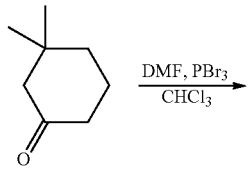

1

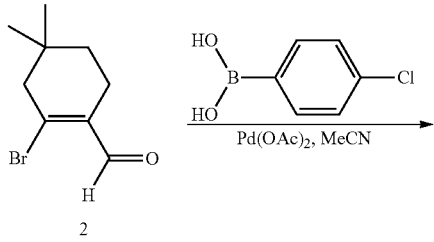

2

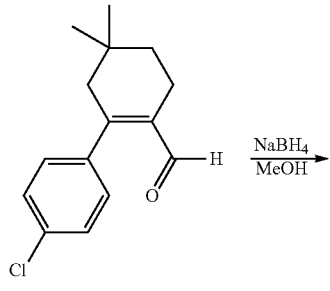

3

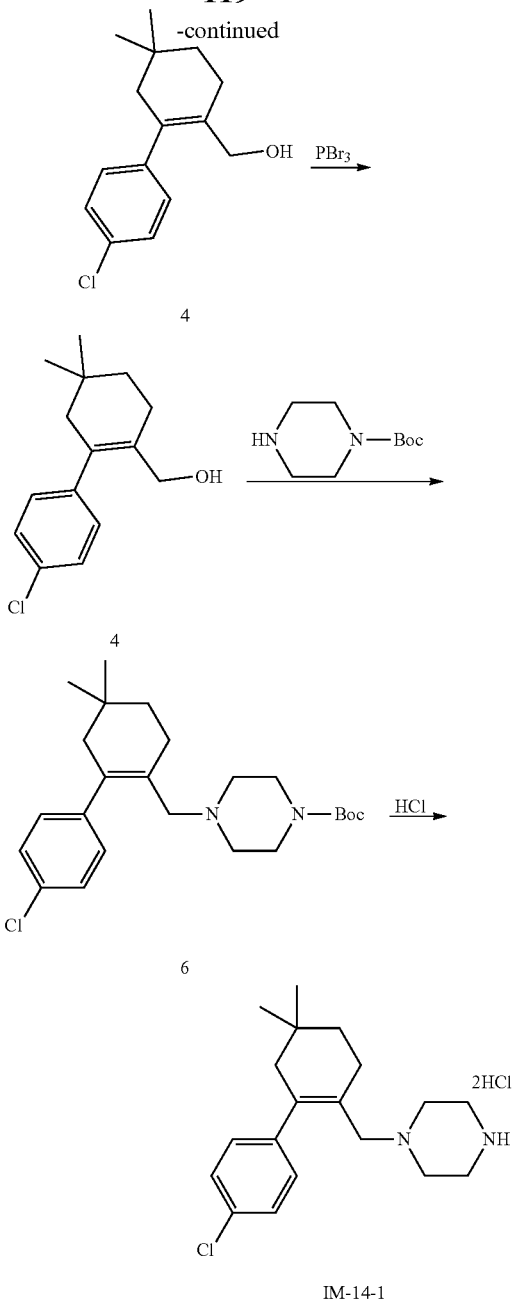

Synthesis of 2-bromo-4,4-dimethylcyclohex-1-enecarbaldehyde 2: A solution of anhydrous chloroform (57 ml) and anhydrous N,N-dimethylformamide (9 mL) was cooled to ~3° C. (internal temperature) under nitrogen before phosphorus tribromide (10 mL, 0.1 mol) was introduced dropwise at a rate so that the reaction was maintained at ~3° C. After the addition was complete the reaction was allowed to warm slowly to ~10° C. and then the temperature was raised to 70° C. where it was maintained for 30 min. The reaction was cooled to rt and 3,3-dimethylcyclohexanone 1 (5 g, 0.04 mol) was added slowly over 20 min. After the addition was complete the reaction was warmed to 70° C. and it was stirred for 1.5 h. The mixture was then cooled to 0° C. and a solution of 4M sodium acetate (53 ml) was added slowly. The pH of the resulting solution was adjusted to ~7 using a solution of 5M NaOH and the mixture was then extracted with heptanes (100 mL×3). The combined organic fractions were dried ($Na_2SO_4$), filtered and concentrated under reduced pressure to give 2-bromo-4,4-dimethylcyclohex-1-enecarbaldehyde 2 (4 g, 49%) as a yellow oil.

Synthesis of 2-(4-chlorophenyl)-4,4-dimethylcyclohex-1-enecarbaldehyde 3: To a degassed solution of 2-bromo-4,4-dimethylcyclohex-1-enecarbaldehyde 2 (5 g, 0.023 mol) and 4-chlorophenyl boronic acid (3.6 g, 0.023 mol) in 1,4-dioxane (50 mL) at rt was added a solution of 2M $Na_2CO_3$ (20.4 ml). Nitrogen was bubbled through the mixture for 2 min and then $PdCl_2$(dppf) (0.5 g) was added. The reaction flask was heated to 120° C. where it was maintained for 3 h. After this time the suspension was cooled to rt and filtered through Celite. The collected solids were washed with additional dichloromethane and the combined filtrate and washings were concentrated under reduced pressure. Purification by column chromatography on silica with PE:EA=20:1 gave 2-(4-chlorophenyl)-4,4-dimethylcyclohex-1-enecarbaldehyde 3 (3 g, 53%) as a white solid. MS: 249[M+H]$^+$ Synthesis of (2-(4-chlorophenyl)-4,4-dimethylcyclohex-1-enyl)methanol 4: A solution of 2-(4-chlorophenyl)-4,4-dimethylcyclohex-1-enecarbaldehyde 3 (20 g, 80.6 mmol) in MeOH (100 mL) was cooled to 0° C., $NaBH_4$ (3.1 g, 80.6 mmol) was added portionwise to the reaction at a rate so that the reaction was maintained at 0-5° C. After added, the mixture was stirred for 1 h at 0° C. Water was added slowly to the mixture and extracted with EA (200 mL×3), the organic layer was washed with brine and dried $Na_2SO_4$, filtered and concentrated under reduced pressure to give (2-(4-chlorophenyl)-4,4-dimethylcyclohex-1-enyl)methanol 4 (15 g, 75%) as a white solid. MS: 233[M+H—$H_2$O]$^+$ Synthesis of 1-(2-(bromomethyl)-5,5-dimethylcyclohex-1-enyl)-4-chlorobenzene 5: A solution of (2-(4-chlorophenyl)-4,4-dimethylcyclohex-1-enyl)methanol 4 (15 g, 0.060 mol) and in $Et_2O$ (300 ml) was cooled to 0° C. before phosphorus tribromide (7.5 mL) was added dropwise to the mixture, after added, the mixture was stirred for 1 h at 0° C. for 90 minutes. The reaction mixture was added $H_2O$ before being extracted with EA. The organic layer was washed with a saturated $NaHCO_3$ solution and brine and dried $Na_2SO_4$, filtered and concentrated under reduced pressure to give 1-(2-(bromomethyl)-5,5-dimethylcyclohex-1-enyl)-4-chlorobenzene 5 (18 g, 96%) as a colorless oil.

Synthesis of tert-butyl 4-((2-(4-chlorophenyl)-4,4-dimethylcyclohex-1-enyl)methyl)piperazine-1-carboxylate—To a solution of 1-bromo-2-(bromomethyl)-5,5-dimethylcyclohex-1-ene 5 (21 g, 0.067 mol) and tert-butyl piperazine-1-carboxylate (12.4 g, 0.067 mol) in dichloromethane (200 ml) at rt was added TEA (12.2 g, 0.12 mol). The reaction was stirred for 2 h. The reaction mixture was concentrated under reduced pressure to give the crude product. Purification by column chromatography on silica with PE:EA=20:1 provided tert-butyl 4-((2-(4-chlorophenyl)-4,4-dimethylcyclohex-1-enyl)methyl)piperazine-1-carboxylate 6 (21 g, 75%).

Synthesis of 1-((2-(4-chlorophenyl)-4,4-dimethylcyclohex-1-enyl)methyl)piperazine hydrogen chloride: To a solution of tert-butyl 4-((2-(4-chlorophenyl)-4,4-dimethylcyclohex-1-enyl)methyl)piperazine-1-carboxylate 6 (30 g, 0.072 mol) in MeOH (20 ml) was added conc. HCl (50 mL). The reaction was stirred for 24 hours and then concentrated under reduced pressure. A saturated solution of $Na_2CO_3$ was added to adjust the pH to ~8-9 and the mixture was extracted with dichloromethane (×2). The combined extracts were washed with brine, dried ($Na_2SO_4$), filtered and concentrated under reduced pressure. The oil product was treated with MeOH/HCl(g) (3M, 500 mL) and stirred for 1 hour, then concentrated under reduced pressure to get the product 1-((2-(4-chlorophenyl)-4,4-dimethylcyclohex-1-enyl)methyl)piperazine hydrogen chloride IM-14-1 (23 g, 83%). MS: 319[M+H]+ ¹H NMR (400 MHz, DMSO) δ 11.51 (s, 1H), 9.60 (s, 1H), 9.18 (s, 1H), 7.45 (d, J=8.2 Hz, 2H), 7.15 (d, J=8.0 Hz, 2H), 3.43 (s, 8H), 2.84 (s, 2H), 2.39 (s, 2H), 2.03 (s, 2H), 1.45 (t, J=6.0 Hz, 2H), 0.96 (s, 6H).

Example 2: Preparation of Key Intermediate IM-14-3

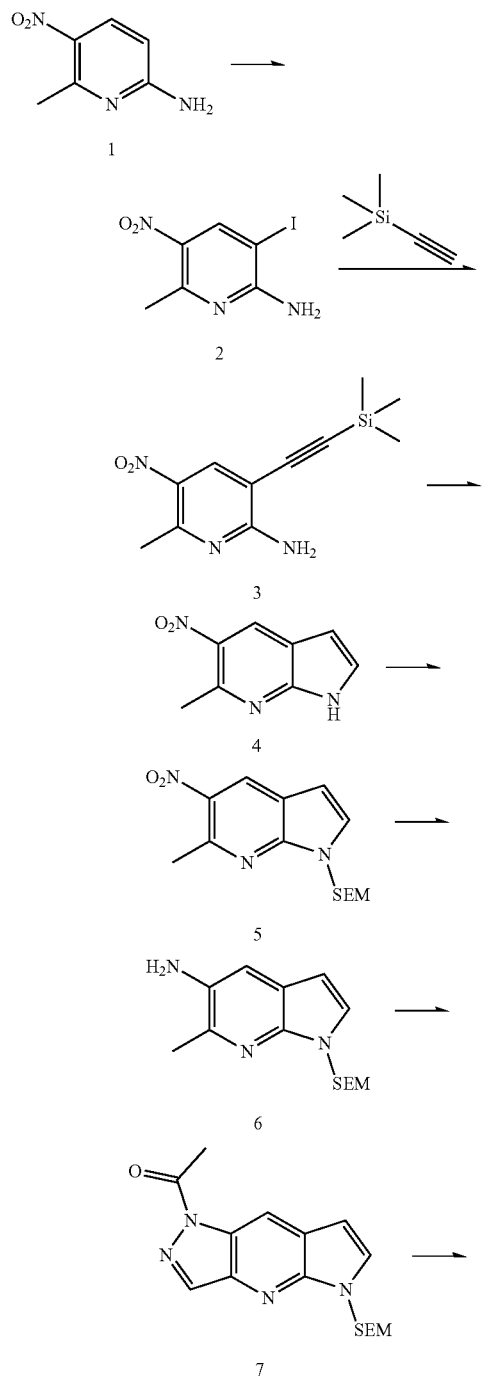

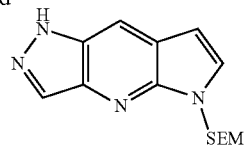
IM-14-3

Step 1: To a solution of compound 1 (200 g, 1.3 mol) in a solution of sulfuric acid (314 mL) and water (2.5 L) was added potassium iodide (217 g, 1.3 mol) and KIO₃ (140 g, 655 mmol) at 20° C. The mixture was stirred at 80° C. for 4 h. TLC (petroleum ether:ethyl acetate=1:1, R$_f$=0.43) showed reactant was consumed completely, and one major new spot with larger polarity was detected. The five reactions were combined for workup. The mixture was cooled to RT and adjusted to pH 9 with the careful addition of NaOH (5N). Sodium sulfite saturated solution was added with vigorous stirring until the iodine color had been disappeared. A significant amount of brown solid remained out of solution, which was collected by filtration, washed with water (2000 mL) to give compound 2 (1.5 kg, 5.4 mol, 82.1% yield) as a brown solid. ¹H NMR: (400 MHz, DMSO-d₆) δ 8.50 (s, 1H), 2.58 (s, 3H).

Step 2: To a solution of compound 2 (387 g, 1.4 mol) in THF (2.4 L) was added TEA (422 g, 4.2 mol) and CuI (26.47 g, 139 mmol). The mixture was degassed and purged with nitrogen atmosphere for 3 times, Pd(PPh₃)₂Cl₂ (29.3 g, 42 mmol) was added and the mixture was degassed and purged with nitrogen atmosphere for 3 times again. Then ethynyl(trimethyl)silane (164 g, 1.7 mol) was added drop-wise. During which the temperature was maintained below 30° C. The mixture was stirred at 25° C. for 3 h under nitrogen atmosphere. TLC (petroleum ether:ethyl acetate=1:1, R$_f$=0.43) show reactant was consumed completely, and one major new spot with larger polarity was detected. The four reactions were combined for workup. The mixture was filtered and concentrated under reduced pressure to give a residue. The resulting residue was dissolved in water (10 L) and extracted with ethyl acetate (4×1 L). The organic layer was washed with water and then separated out. The organic layer dried over anhydrous sodium sulfate, filtered and concentrated under reduced pressure at 50° C. The solid was added to petroleum ether (300 mL) and stirred for 30 min. Then the suspension was filtered and the solid was dried in air to give compound 3 (1.3 kg, crude) as a brown solid. The solid was added to the solution of DCM (5 L) and stirred at 25° C. for 3 h. Then filtered and concentrated to give compound 3 (700 g) as yellow solid. ¹H NMR: (400 MHz, DMSO-d₆) δ 8.15 (s, 1H), 2.63 (s, 3H), 0.24 (s, 9H).

Step 3: To a solution of t-BuOK (126 g, 1.1 mol, 2.0 eq) in NMP (500 mL) was added a solution of compound 3 (140 g, 561 mmol, 1.0 eq) in NMP (400 mL) in dropwise at 140° C. The mixture was stirred at 140° C. for 3 h. LCMS showed the reaction was completed. The mixture was cooled to 20° C. and combined poured into saturated NaCl solution (5 L) and extracted with ethyl acetate (5 L*3). The combined organic phase was washed with brine (3 L), dried with anhydrous Na₂SO₄, filtered and concentrated in vacuum to give compound 4 (140 g, 790.3 mmol, 35.2% yield) as yellow solid. ¹H NMR: (400 MHz, DMSO-d₆) δ 12.20 (s, 1H), 8.68 (s, 1H), 7.61 (t, J=2.1 Hz, 1H), 6.59 (s, 1H), 2.75 (s, 3H).

Step 4: To a solution of compound 4 (45 g, 254 mmol, 1.0 eq) in DMF (250 mL) was added NaH (12.2 g, 305 mmol, 60% purity, 1.2 eq) at 0° C. in portion. The mixture was stirred at 0° C. for 1 h. Then the mixture was warmed to 25° C. and SEM-Cl (50.8 g, 304.8 mmol, 54 mL, 1.2 eq) was added in dropwise within 1 h. The mixture was stirred at 25° C. for 3 h. LCMS showed the reaction was completed. All the mixture was poured into ice-water and combined extracted with ethyl acetate (1 L*2). The combined organic phase was washed with brine (500 mL*N), dried with anhydrous Na$_2$SO$_4$, filtered and concentrated in vacuum. The mixture was purified by silica gel (Petroleum ether: Ethyl acetate=10:1 to 5:1, Rf=0.32) to give compound 5 (95 g, 309 mmol, 40.6% yield) as yellow solid. $^1$H NMR: (400 MHz, CDCl$_3$) δ 8.70 (s, 1H), 7.49 (d, J=3.2 Hz, 1H), 6.68 (d, J=4.0 Hz, 1H), 5.74 (s, 2H), 3.61 (t, J=8.0 Hz, 2H), 2.99 (s, 3H), 0.99 (t, J=8.4 Hz, 2H), 0.00 (s, 9H)

Step 5: To a solution of compound 5 (32 g, 104 mmol, 1.0 eq) and Pd/C (3.2 g) in THF (300 mL) was added AcOH (31.3 g, 520.5 mmol, 30 mL, 5.0 eq), the suspension was degassed under vacuum and purged with H$_2$ three times. The mixture was stirred under H$_2$ (50 psi) at 30° C. for 12 hours. LCMS showed the reaction was completed. The mixture was filtered and concentrated in vacuum. The residue was purified by silica gel (Petroleum ether:Ethyl acetate=10:1 to 2:1, Rf=0.2) to give compound 6 (53 g, 191 mmol, 61.2% yield) as yellow solid. $^1$H NMR: (400 MHz, CDCl$_3$) δ 7.25 (d, J=4.0 Hz, 1H), 6.37 (d, J=2.8 Hz, 1H), 5.67 (d, J=4.4 Hz, 2H), 3.61 (t, J=8.4 Hz, 2H), 3.48 (s, 2H), 2.58 (s, 3H), 0.99 (t, J=8.4 Hz, 2H), 0.00 (s, 9H)

Step 6: To a solution of compound 6 (14.3 g, 51.5 mmol, 1.0 eq) in toluene (250 mL) was added Ac$_2$O (20 g, 195.9 mmol, 18 mL, 3.8 eq) and AcOK (20.2 g, 206.2 mmol, 4.0 eq), the mixture was stirred at 60° C. for 3 h. Then isopentyl nitrate (17.2 g, 129 mmol, 2.5 eq) was added to the mixture in dropwise, the mixture was heated to 110° C. and stirred for 9 h. TLC (Petroleum ether:Ethyl acetate=2:1, Rf=0.1) showed the reaction was completed. The two mixtures was cooled to 25° C. and poured into water (500 mL). The aqueous phase was extracted with ethyl acetate (200 mL*2). The combined organic phase was washed with brine (200 mL), dried with anhydrous Na$_2$SO$_4$, filtered and concentrated in vacuum. The residue was purified by silica gel (Petroleum ether:Ethyl acetate=10:1 to 2:1) to give compound 7 (20 g, 60.5 mmol, 58.7% yield) as yellow solid. $^1$H NMR: (400 MHz, CDCl$_3$) δ 9.01 (s, 1H), 8.44 (s, 1H), 7.64 (d, J=3.6 Hz, 1H), 6.77 (d, J=3.9 Hz, 1H), 5.82 (d, J=6.4 Hz, 2H), 3.65 (t, J=8.4 Hz, 3H), 2.90 (s, 2H), 1.01 (t, J=8.4 Hz, 2H), 0.00 (s, 9H).

Step 7: To a solution of compound 7 (20 g, 60.5 mmol, 1.0 eq) in MeOH (250 mL) was added K$_2$CO$_3$ (16.7 g, 121.0 mmol, 2.0 eq), the mixture was stirred at 20° C. for 5 h. LCMS showed the reaction was completed. The mixture was concentrated in vacuo and water (100 mL) was added. The aqueous phase was extracted with ethyl acetate (100 mL*3). The combined organic phase was washed with brine (100 mL*), dried with anhydrous Na$_2$SO$_4$, filtered and concentrated in vacuum. The residue was purified by silica gel (Petroleum ether:Ethyl acetate=10:1 to 2:1, Rf=0.1) to give compound IM-14-7 (17 g, 58.9 mmol, 97.4% yield) as yellow solid. $^1$H NMR (400 MHz, CDCl$_3$) δ 10.62 (s, 1H), 8.43 (s, 1H), 8.06 (s, 1H), 7.60 (d, J=3.6 Hz, 1H), 6.66 (d, J=3.6 Hz, 1H), 5.82 (s, 21H), 3.65-3.69 (m, 2H), 1.09 (s, 2H), 0.00 (s, 9H).

Example 3: Alternative Preparation of IM-14-3

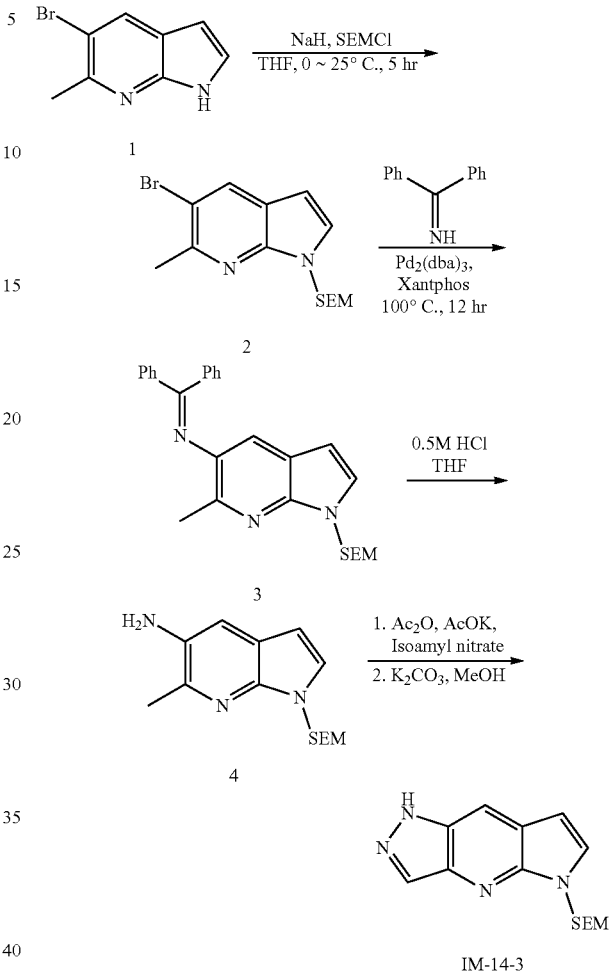

General procedure for preparation of compound 2: To a solution of 5-bromo-6-methyl-1H-pyrrolo[2,3-b]pyridine (10 g, 47.4 mmol, 1.00 eq) in DMF (150.00 mL), the mixture was cooled to 0° C. and NaH (2.84 g, 71 mmol, 60% purity, 1.50 eq) was added to the mixture. The reaction mixture was stirred at 0° C. for 1 hr, 2-(chloromethoxy)ethyl-trimethyl-silane (10.3 g, 61.6 mmol, 11 mL, 1.30 eq) was added dropwise to the mixture. The mixture was stirred at 25° C. for 3 hr. TLC indicated 0% of Reactant 1 was remained, and one major new spot with larger polarity (Petroleum ether: Ethyl acetate=5:1, Rf=0.51) was detected. The mixture was poured into NH$_4$Cl solution (40 ml), concentrated, then extracted with EA (30 ml×3), combine the organic layers, washed with brine (20 ml), and concentrated to give crude product. The residue was purified by column chromatography (SiO2, Petroleum ether/Ethyl acetate=100/1 to 5:1). Compound 2 (10.00 g, 29.30 mmol, 61.84% yield) was obtained. $^1$H NMR: ET6225-38-P1A 400 MHz CDCl$_3$ δ 8.01 (s, 1H), 7.26 (d, J=3.2 Hz, 1H), 6.40 (d, J=3.2 Hz, 1H), 5.62 (s, 2H), 3.55 (t, J=16 Hz, 2H), 2.75 (s, 3H), 0.91 (t, J=16 Hz, 2H), 0.07 (s, 9H).

General procedure for preparation of compound 3: A mixture of compound 2 (5.50 g, 16.1 mmol, 1.00 eq), diphenylmethanimine (3.50 g, 19.3 mmol, 1.20 eq), Xantphos (1.86 g, 3.22 mmol, 0.20 eq), Cs$_2$CO$_3$ (10.5 g, 32.2 mmol, 2.00 eq) in dioxane (150 mL) was degassed and purged with N$_2$ for 3 times, and then Pd$_2$(dba)$_3$ (885 mg, 966 umol, 0.06 eq) was added to the mixture. Then the mixture was stirred at 100° C. for 15 hour under N$_2$ atmosphere. TLC (Petroleum ether/Ethyl acetate=5:1) showed many spot. The desired compound was detected by LCMS (RT=1.363). The reaction mixture was concentrated under reduced pressure to give a residue. The crude product 3 was used into the next step without further purification General procedure for preparation of compound 4: A mixture of crude compound 3 (8.00 g, 11.8 mmol, 1.00 eq), 0.5 N HCl (100 mL), in THF (100 mL) was degassed and purged with N$_2$ for 3 times, and then the mixture was stirred at 25° C. for 14 hour under N$_2$ atmosphere. TLC (Petroleum ether/Ethyl acetate=3:1) showed the desired product was detected. The mixture was quenched by aq. NaHCO$_3$ (200 ml) to adjust pH=8, then extracted with Ethyl acetate (100 ml×3), combine the organic layers, washed with brine (100 ml), dried over sodium sulfate, concentrated to give crude product. The residue was purified by column chromatography (SiO2, Petroleum ether/Ethyl acetate=100/1 to 5:1) Compound 4 (3 g, 8.65 mmol, 73.5% yield, 80% purity) was obtained as a solid. $^1$H NMR: ET6225-46-P1A 400 MHz CDCl$_3$ δ 7.25 (s, 2H), 6.42 (s, 1H), 5.67 (s, 2H), 3.60 (t, J=8 Hz, 2H), 2.62 (s, 3H), 0.98 (t, J=8 Hz, 2H), 0.04 (s, 9H).

General procedure for preparation of compound 5: A mixture of compound 4 (2.00 g, 7.21 mmol, 1.00 eq) and Ac$_2$O (1.6 g, 15.6 mmol, 2.2 eq) in CHCl$_3$ (50.00 mL) was added AcOK (7.08 g, 72.10 mmol, 10 eq), and then the mixture was stirred at 25° C. for 3 hr, under N$_2$ atmosphere. then isoamyl nitrate (3.38 g, 28.8 mmol, 4 eq) was added, heated to 60° C. for 14 hr, TLC (Petroleum ether/Ethyl acetate=3:1, Rf (product=0.43) showed the starting material was consumed completely. The mixture was quenched by aq. NaHCO$_3$ (200 ml), then extracted with DCM (100 ml×3), combine the organic layers, washed with brine (100 ml), dried over sodium sulfate, concentrated to give crude product. The residue was purified by column chromatography (SiO2, Petroleum ether/Ethyl acetate=100/1 to 5:1). Compound 5_Ac (600 mg, 21.36% yield, 85% purity) and N-[6-methyl-1-(2-trimethylsilylethoxymethyl)pyrrolo[2,3-b]pyridin-5-yl]acetamide (1.50 g, 4.70 mmol, 65.12% yield) were obtained.

A mixture of Compound 5_Ac (600 mg, 1.82 mmol, 1.00 eq) in MeOH (5 mL) was added K$_2$CO$_3$ (753 mg, 5.45 mmol, 3.00 eq), and then the mixture was stirred at 25° C. for 2 hr, under N$_2$ atmosphere. TLC showed none of Compound 5 was remained. The mixture was poured into water (200 ml), and then extracted with DCM (100 ml×3), combine the organic layers, washed with brine (100 ml), and dried over sodium sulfate, concentrated to give crude product. The residue was purified by column chromatography (SiO2, Petroleum ether/Ethyl acetate=100/1 to 5:1). Compound 5 (500 mg, 95.25% yield) was obtained as a yellow solid. $^1$H NMR: ET6225-47-P1A 400 MHz CDCl$_3$ δ 9.05 (s, 1H), 8.45 (s, 1H), 7.64 (s, 1H), 6.77 (s, 1H), 5.82 (s, 2H), 3.65 (t, J=8 Hz, 2H), 2.90 (s, 3H), 1.01 (t, J=8 Hz, 2H), 0.01 (s, 9H). $^1$H NMR: ET6225-51-P1A 400 MHz CDCl$_3$ δ 8.05 (s, 1H), 7.60 (s, 1H), 6.66 (s, 1H), 5.82 (s, 2H), 3.67 (t, J=16 Hz, 2H), 1.01 (t, J=16 Hz, 2H), 0.04 (s, 9H).

Example 4: Preparation of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(pyrazolo[4,3-b]pyrrolo[3,2-e]pyridin-1(5H)-yl)benzamide A mixture of compound IM-14-3 (500 mg, 1.73 mmol, 1.00 eq), ethyl 4-bromo-2-fluoro-benzoate (641 mg, 2.60 mmol, 1.50 eq), Cs$_2$CO$_3$ (1.69 g, 5.19 mmol, 3.00 eq) in DMF (10 mL) was degassed and purged with N$_2$ for 3 times, and then the mixture was stirred at 125° C. for 1 hour under N$_2$ atmosphere under microwave condition. TLC indicated the desired compound (Rf: 0.24). The reaction mixture was filtered and the filtrate was concentrated under reduced pressure to give a residue. The residue was purified by silica gel column chromatography (Petroleum ether/Ethyl acetate=100:1 to 3:1). ethyl 4-bromo-2-(5-((2-(trimethylsilyl)ethoxy)methyl)pyrazolo[4,3-b]pyrrolo[3,2-e]pyridin-1 (5H)-yl)benzoate (400 mg, 659 umol, 38.1% yield, 85% purity) was obtained as a yellow oil. $^1$H NMR: ET6225-63-P1A 400 MHz CDCl$_3$ δ 8.50 (s, 1H) 7.90-7.96 (m, 3H) 7.72 (d, J=8.38 1H) 7.60 (d, J=3.53 Hz, 1H) 6.60 (d, J=4 Hz, 1H) 5.81 (s, 2H) 3.97-4.07 (m, 2H) 3.62-3.70 (m, 2H) 0.97-1.05 (m, 2H) 0.83 (t, J=7.28 Hz, 3H) 0.01 (s, 9H).

A mixture of ethyl 4-bromo-2-(5-((2-(trimethylsilyl)ethoxy)methyl)pyrazolo[4,3-b]pyrrolo[3,2-e]pyridin-1(5H)-yl)benzoate (800 mg, 1.55 mmol, 1.00 eq), compound 7 (594 mg, 1.86 mmol, 1.20 eq), Xantphos (359 mg, 621 umol, 0.40 eq), Cs$_2$CO$_3$ (1.52 g, 4.66 mmol, 3.00 eq) in dioxane (20 mL) was degassed and purged with N$_2$ for 3 times, and then Pd$_2$(dba)$_3$ (284 mg, 310 umol, 0.20 eq) was added to the mixture, the mixture was stirred at 100° C. for 15 hour under N$_2$ atmosphere. TLC showed the reaction was completed. The desired compound (Rf: 0.24) was detected. The reaction mixture was filtered and the filtrate was concentrated under reduced pressure to give a residue. The residue was purified by silica gel chromatography (100-200 mesh silica gel, Petroleum ether/Ethyl acetate=100/1-3/1). Ethyl 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoate (600 mg, 637 umol, 41.1% yield, 80% purity) was obtained as a yellow solid. $^1$H NMR: ET6225-84-p1a 400 MHz CDCl$_3$ δ 8.46 (s, 1H) 8.04 (d, J=8.8 Hz, 1H) 7.73-7.86 (m, 1H) 7.55 (d, J=3.5 Hz, 1H) 6.95-7.05 (m, 4H) 6.57 (d, J=3.5 Hz, 1H) 5.80 (s, 2H) 3.88 (q, J=7 Hz, 2H) 3.61-3.70 (m, 2H) 3.37 (d, J=4.8 Hz, 4H) 2.89 (s, 2H) 2.42 (d, J=4.8 Hz, 4H) 2.29 (s, 2H) 2.07 (s, 2H) 1.63 (s, 7H) 1.52 (t, J=6.39 Hz, 2H) 0.85-1.08 (m, 16H) 0.68 (t, J=7.2 Hz, 3H) 0.00 (s, 9H).

A mixture of ethyl 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoate (500 mg, 664 umol, 1.00 eq), NaOH (79.6 mg, 1.99 mmol, 3.00 eq) in MeOH (10 mL), THF (10 mL), H$_2$O (5 mL) was stirred at 0-25° C. for 2 hour under N$_2$ atmosphere. The desired compound was detected. The reaction mixture was concentrated under reduced pressure to give a residue. this residue was dissolved in water, then was adjusted to pH=4-5 with 0.5 M HCl and extracted with Ethyl acetate (20 ml×3) combine the organic layers, washed with brine, dried over sodium sulfate, concentrated to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoic acid (400 mg, 74.8% yield, 90% purity) was obtained as a white solid. $^1$H NMR: ET6225-85-p1a 400 MHz CDCl$_3$ δ 8.45 (s, 1H) 8.07 (d, J=9.2 Hz, 1H) 7.85 (s, 1H) 7.53 (d, J=3.9 Hz, 1H) 7.30-7.34 (m, 3H) 7.00 (d, J=8.4 Hz, 2H) 6.84-6.93 (m, 2H) 6.52-6.57 (m, 1H) 5.76 (s, 2H) 3.61-3.69 (m, 2H) 3.35 (s, 3H) 2.47 (s, 2H) 2.28 (s, 2H) 2.06 (s, 2H) 1.49 (t, J=5.9 Hz, 2H) 1.27-1.36 (m, 1H) 0.96-1.05 (m, 9H), 0.01 (s, 9H).

A mixture of 4-(4-((4'-chloro-5,5-dimethyl-3,4,5,6-tetrahydro-[1,1'-biphenyl]-2-yl)methyl)piperazin-1-yl)-2-(5-((2-

(trimethylsilyl)ethoxy)methyl)pyrazolo[4,3-b]pyrrolo[3,2-e]pyridin-1(5H)-yl)benzoic acid (400 mg, 551 umol, 1.00 eq), and HATU (629 mg, 1.65 mmol, 3.00 eq) NH₄Cl (147 mg, 2.76 mmol, 5.00 eq) Et₃N (558 mg, 5.51 mmol, 10.00 eq) in DMF (3 mL) was stirred at 25° C. for 15 hr under N₂ atmosphere. The desired compound was detected by TLC. The reaction mixture was filtered and the filtrate was concentrated under reduced pressure to give a residue. The residue was purified by column chromatography (SiO2, DCM: MeOH=200/1 to 20:1). 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (300 mg, 75% yield) was obtained as a yellow solid. ¹H NMR: ET6225-86-p1a 400 MHz CDCl₃ δ8.44 (s, 1H) 7.88-7.94 (m, 1H) 7.83 (d, J=8.8 Hz, 1H) 7.55-7.60 (m, 1H) 7.39 (d, J=7.9 Hz, 2H) 7.05 (d, J=7.9 Hz, 2H) 6.87 (s, 1H) 6.65 (d, J=3.5 Hz, 1H) 5.74-5.80 (s, 2H) 3.66 (m, 4H) 3.53 (br. s., 2H) 3.21-3.34 (m, 11H) 2.09-2.32 (m, 3H) 1.41 (m, 17H) 0.01 (s, 9H).

A mixture of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (300 mg, 414 umol, 1.00 eq) in THF (8 mL), then NaH (49.7 mg, 1.24 mmol, 60% purity, 3.00 eq) was added at 0° C., stirred for 0.5 hr, then 4-chloro-3-nitro-benzenesulfonyl chloride (117 mg, 456 umol, 1.10 eq) in THF (2 mL) was added, the mixture was stirred at 25° C. for 2 hr under N₂ atmosphere. The desired compound was detected. The reaction mixture was concentrated under reduced pressure to give a residue. The residue was purified by prep-TLC (SiO2, DCM/MeOH=10/1). N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 umol, 51.16% yield) was obtained as yellow solid. ¹H NMR: ET6215-89-p1a 400 MHz CDCl₃ δ8.44 (s, 1H) 7.95 (s, 1H) 7.76 (s, 1H) 7.40-7.53 (m, 1H) 6.95 (d, J=7.8 Hz, 5H) 6.75 (s, 1H) 6.51 (s, 1H) 5.71 (s, 3H) 5.30 (s, 2H) 3.50-3.65 (m, 5H) 3.26 (s, 3H) 3.06 (d, J=6.65 Hz, 2H) 2.85 (s, 1H) 2.36 (s, 2H) 2.21 (s, 1H) 2.00 (s, 4H) 1.44 (s, 1H) 1.14-1.31 (m, 8H) 0.96 (m, 13H) 0.07 (s, 9H).

A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200 mg, 212 umol, 1.00 eq) in TFA (3.00 mL) and DCM (3.00 mL) was stirred at 25° C. for 14 hr under N₂ atmosphere. The desired compound (Rt=1.146) was detected on LC-MS. The reaction mixture was concentrated under reduced pressure to give a crude as as a yellow solid. A mixture of the crude (150 mg, 204 umol, 1.00 eq) and cyclohexylmethanamine (69.5 mg, 614 umol, 3.00 eq) in CH₃CN (4 mL) in a microwave tube, then DIPEA (79.3 mg, 614 umol, 3.00 eq) was added, the mixture was stirred at 125° C. for 14 hr under N₂ atmosphere under microwave. The desired compound was detected by LCMS (Rt=0.573), The reaction mixture was concentrated under reduced pressure to give a residue. The residue was purified by prep-HPLC (neutral) and the recovered product was purified by Re-prep-HPLC (TFA). Two batches of target compound were obtained as yellow solid. The first batch is 11 mg; the second batch is 23 mg. ¹H NMR: ET6225-91-p1c 400 MHz DMSO 611.50 (br. s., 1H) 8.64 (s, 1H) 8.40 (s, 1H) 7.97 (s, 1H) 7.89 (s, 1H) 7.60-7.69 (m, 2H) 7.56 (m, 1H) 7.40 (m, 2H) 6.98-7.16 (m, 5H) 6.35 (s, 1H) 3.81-4.03 (m, 3H) 3.12-3.41 (m, 6H) 2.24 (m, 2H) 2.05 (s, 2H) 1.65 (m, 3H) 1.44-1.53 (m, 2H) 1.19-1.38 (m, 3H) 0.96 (s, 6H), LCMS: (M+H)⁺: 892.2.

Example 6: Preparation of 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)piperidin-4-yl)amino)phenyl)sulfonyl)-2-(pyrazolo[4,3-b]pyrrolo[3,2-e]pyridin-1(5H)-yl)benzamide To a mixture of N-((4-chloro-3-nitrophenyl)sulfonyl)-4-(4-((4'-chloro-5-methyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.00 g, 1.06 mmol, 1.00 eq) in dichloromethane (10 mL) was added Trifluoroacetic Acid (15.40 g, 135 mmol, 10.00 mL) in one portion at 20° C. The mixture was stirred at 20° C. for 14 hrs, LCMS showed the product was detected. The reaction mixture was concentrated under reduced pressure to remove dichloromethane, and then diluted with water (100 mL), and extracted with ethyl acetate (20 mL*3). The combined organic layers were washed with brine (100 mL), dried over Na₂SO₄, filtered and concentrated under reduced pressure to give the crude product Compound N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (800.00 mg, crude) was used into the next step without further purification.

A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (100 mg, 118 umol, 1.00 eq) and 1-tetrahydropyran-4-ylpiperidin-4-amine (65.5 mg, 355 umol, 3.00 eq) in CH₃CN (1.0 mL) in a microwave tube, then DIPEA (153 mg, 1.19 mmol, 206 uL, 10 eq) was added, the mixture was stirred at 125° C. for 14 hr under N₂ atmosphere under microwave. LCMS and HPLC showed the product was detected. The reaction mixture was concentrated under reduced pressure to remove CH₃CN, and then diluted with water (10 mL) and extracted with dichloromethane (5 mL*3). The combined organic layers were washed with brine (10 mL), dried over Na₂SO₄, filtered and concentrated under reduced pressure to give a residue. The residue was purified by prep-HPLC (prep-HPLC (column: YMC-Actus Triart C18 150*30 5 u; liquid phase: [A-10 mM NH₄HCO₃ in H₂O; B-ACN]B %: 45%-65%, 12 min])) to give 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)piperidin-4-yl)amino)phenyl)sulfonyl)-2-(pyrazolo[4,3-b]pyrrolo[3,2-e]pyridin-1(5H)-yl)benzamide (2.60 mg, 2% yield) as a white solid. LCMS: (M/2+1): 481.1 ¹H NMR: CDCl₃ 400 MHz δ 8.45 (s, 1H) 8.22-8.38 (m, 2H) 7.81 (d, J=8.0 Hz, 1H) 7.54 (s, 2H) 7.43 (d, J=8.0 Hz, 1H) 6.87 (d, J=8.0 Hz, 4H) 6.67 (s, 1H) 6.31 (s, 1H) 3.98 (d, J=8.0 Hz, 2H) 3.29-3.35 (m, 3H) 3.20 (s, 5H) 2.74 (s, 3H) 2.25 (s, 5H) 2.14 (s, 3H) 1.92 (s, 5H) 1.18 (s, 2H) 0.89 (s, 9H)

Example 7: Preparation of 4-(4-((4'-chloro-5,5-dimethyl-3,4,5,6-tetrahydro-[1,1'-biphenyl]-2-yl)methyl)piperazin-1-yl)-N-((4-((3-morpholinopropyl)amino)-3-nitrophenyl)sulfonyl)-2-(pyrazolo[4,3-b]pyrrolo[3,2-e]pyridin-1(5H)-yl)benzamide A mixture of N-((4-chloro-3-nitrophenyl)sulfonyl)-4-(4-((4'-chloro-5,5-dimethyl-3,4,5,6-tetrahydro-[1,1'-biphenyl]-

2-yl)methyl)piperazin-1-yl)-2-(5-(hydroxymethyl)pyrazolo[4,3-b]pyrrolo[3,2-e]pyridin-1(5H)-yl)benzamide (100 mg, 118 umol, 1.00 eq) and 3-morpholinopropan-1-amine (51 mg, 355 umol, 3.00 eq) in CH$_3$CN (1.00 mL) in a microwave tube, then DIPEA (60 mg, 464 umol, 3.92 eq) was added, the mixture was stirred at 125° C. for 14 hr under N$_2$ atmosphere under microwave. LCMS and HPLC showed the product was detected. The reaction mixture was concentrated under reduced pressure to remove CH$_3$CN, and then diluted with water (10 mL) and extracted with dichloromethane (5 mL*3). The combined organic layers were washed with brine (10 mL), dried over Na$_2$SO$_4$, filtered and concentrated under reduced pressure to give a residue. The residue was purified by prep-HPLC (prep-HPLC (column: YMC-Actus Triart C18 150*30 5 u; liquid phase: [A-10 mM NH$_4$HCO$_3$ in H$_2$O; B-ACN]B %: 45%-75%, 12 min])) to give 4-(4-((4'-chloro-5,5-dimethyl-3,4,5,6-tetrahydro-[1,1'-biphenyl]-2-yl)methyl)piperazin-1-yl)-N-((4-((3-morpholinopropyl)amino)-3-nitrophenyl)sulfonyl)-2-(pyrazolo[4,3-b]pyrrolo[3,2-e]pyridin-1(5H)-yl)benzamide (2.0 mg, 2% yield) as a yellow solid. LCMS: (M/2+1): 461.1 $^1$H NMR: ET10360-22-P1A1 CDCl$_3$ 400 MHz δ 9.06 (s, 1H) 8.46 (s, 1H) 8.23-8.39 (m, 2H) 7.81 (d, J=8.0 Hz, 1H) 7.50-7.59 (m, 2H) 7.34 (s, 1H) 6.80-6.92 (m, 3H) 6.68 (s, 1H) 6.46 (d, J=8.0 Hz, 1H) 6.28 (s, 1H) 3.64-3.78 (m, 4H) 3.12-3.29 (m, 6H) 2.66-2.84 (m, 4H) 2.44 (s, 7H) 2.26 (s, 4H) 2.08-2.17 (m, 3H) 1.92 (s, 2H) 1.30-1.43 (m, 4H) 1.06-1.21 (m, 4H) 0.89 (s, 7H)

Example 8: Preparation of 4-(4-((4'-chloro-5,5-dimethyl-3,4,5,6-tetrahydro-[1,1'-biphenyl]-2-yl)methyl)piperazin-1-yl)-N-((4-morpholino-3-nitrophenyl)sulfonyl)-2-(pyrazolo[4,3-b]pyrrolo[3,2-e]pyridin-1(5H)-yl)benzamide N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 umol, 1.00 eq) was dissolved in DCM (3.00 mL), to which TFA (4.62 g, 40.52 mmol, 3.00 mL, 191.25 eq) was added in one portion. The mixture was then stirred at 25° C. under N$_2$ atmosphere for 14 h. After removal of the solvent, N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (180.00 mg, crude) was obtained as a dark yellow solid which was confirmed by LC-MS and used directly for the next step without further purification.

To the mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (170.00 mg, 201.47 μmol, 1.00 eq) and morpholine (52.66 mg, 604.41 μmol, 53.19 μL, 3.00 eq) in CH$_3$CN (4.00 mL), DIEA (78.12 mg, 604.41 μmol, 105.57 μL, 3.00 eq) was added. The resulting mixture was taken up into a microwave tube, and heated under microwave at 80° C. under N$_2$ atmosphere for 2 h. After removal of the solvent, the crude 4-(4-((4'-chloro-5,5-dimethyl-3,4,5,6-tetrahydro-[1,1'-biphenyl]-2-yl)methyl)piperazin-1-yl)-N-((4-morpholino-3-nitrophenyl)sulfonyl)-2-(pyrazolo[4,3-b]pyrrolo[3,2-e]pyridin-1(5H)-yl)benzamide (300.00 mg, crude) was obtained as a black brown oil which was purified together with EW5403-10 by Prep-HPLC (HCl as additive) to afford 4-(4-((4'-chloro-5,5-dimethyl-3,4,5,6-tetrahydro-[1,1'-biphenyl]-2-yl)methyl)piperazin-1-yl)-N-((4-morpholino-3-nitrophenyl)sulfonyl)-2-(pyrazolo[4,3-b]pyrrolo[3,2-e]pyridin-1(5H)-yl)benzamide HCl salt (41.40 mg) as a yellow solid. The product was confirmed by $^1$H NMR and LC-MS.

Example 9: Preparation of 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo[3,2-e]pyridin-1(5H)-yl)benzamide Synthesis of Tert-butyl 3-morpholinoazetidine-1-carboxylate A mixture of tert-butyl 3-oxoazetidine-1-carboxylate (3.50 g, 20.45 mmol, 1.00 eq) and morpholine (2.32 g, 26.59 mmol, 2.34 mL, 1.30 eq) in DCE (250.00 mL) was stirred at 30° C. for 1 h, and then NaBH(OAc)$_3$ (5.63 g, 26.59 mmol, 1.30 eq) was added. The mixture was stirred at 30° C. for additional 15 h. Sat. Na$_2$CO$_3$ solution (200 mL) was added to the mixture, and the mixture was stirred at 30° C. for 10 min. The organic layer was separated, washed with H$_2$O (200 mL) and brine (200 mL), and then concentrated under reduced pressure. The residue was purified by silica gel chromatography eluted with PE to PE:EA=1:1 to give tert-butyl 3-morpholinoazetidine-1-carboxylate (4.50 g, 18.57 mmol, 90.81% yield) as a light yellow oil which was confirmed by $^1$H NMR.

Synthesis of 4-(azetidin-3-yl)morpholine TFA salt: A mixture of tert-butyl 3-morpholinoazetidine-1-carboxylate (500.00 mg, 2.06 mmol, 1.00 eq) and TFA (7.70 g, 67.53 mmol, 5.00 mL, 32.78 eq) in DCM (20.00 mL) was stirred at 30° C. for 15 h. After removal of the solvent, 4-(azetidin-3-yl)morpholine TFA salt (280.00 mg, crude) was obtained as a yellow oil which was confirmed by LC-MS used directly without further purification.

Synthesis of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide: N-((4-chloro-3-nitrophenyl)sulfonyl)-4-(4-((4'-chloro-5,5-dimethyl-3,4,56-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 μmol, 1.00 eq) was dissolved in DCM (3.00 mL), to which TFA (4.62 g, 40.52 mmol, 3.00 mL, 191.25 eq) was added in one portion. The resulting mixture was then stirred at 25° C. under N$_2$ atmosphere for 14 h. After removal of the solvent, N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (200.00 mg, crude) was obtained as a dark yellow solid which was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo[3,2-e]pyridin-1(5H)-yl)benzamide 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo[3,2-e]pyridin-1(5H)-yl)benzamide HCl salt: A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4, 3-b]pyrrolo[3,2-e]pyridin-1(5H)-yl)benzamide (78.37 mg, 551.10 µmol, 3.00 eq) in CH₃CN (4.00 mL) was added DIEA (71.22 mg, 551.10 µmol, 96.24 µL, 3.00 eq). The resulting mixture was taken up into a microwave tube and heated using microwave at 80° C. for 2 h under N₂ atmosphere. After removal of the solvent, 4-[4-[[2-(4-chlorophenyl)-4,4-dimethyl-cyclohexen-1-yl]methyl]piperazin-1-yl]-N-[4-(3-morpholinoazetidin-1-yl)-3-nitro-phenyl]sulfonyl-2-(5H-pyrazolo[BLAH]pyrrolo[BLAH]-pyridin-1-yl)benzamide (300.00 mg, crude) was obtained as a black brown oil which was purified together with EW5403-7 by Prep-HPLC (HCl) and then by SFC (column: Phenomenex Gemini 150*25 mm*10 um; mobile phase: [water (0.05% ammonia hydroxide v/v)-ACN]; B %: 35%-65%, 10 min) to afford 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo)-2-(pyrazolo[3,2-e]pyridin-1(5H)-yl)benzamide HCl salt (2.40 mg, 2.51 µmol, 7.69% yield, HCl) as a yellow solid. The product was confirmed by LC-MS and ¹H NMR.

Example 10: Preparation of 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide Synthesis of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (100.00 mg, 105.93 µmol, 1.00 eq) was dissolved in DCM (3.00 mL), to which TFA (2.31 g, 20.26 mmol, 1.50 mL, 191.25 eq) was added in one portion. The resulting mixture was then stirred at 25° C. under N₂ atmosphere for 14 h. After removal of the solvent, N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (101.00 mg, crude) was obtained as a dark yellow solid which was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide HCl salt: The mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (101.00 mg, 119.70 µmol, 1.00 eq) and 7-oxa-2-azaspiro[3.5]nonane (78.00 mg, 359.10 µmol, 3.00 eq, OXALIC ACID salt) were dissolved in CH₃CN (4.00 mL), to which DIEA (92.82 mg, 718.20 µmol, 125.43 µL, 6.00 eq) was added. The resulting mixture was taken up into a microwave tube. The tube was heated under N₂ atmosphere at 80° C. for 3 h. After removal of the solvent, the residue was purified by Prep-HPLC (HCl, column: Phenomenex Synergi C₁₈ 150*25*10 µm; mobile phase: [water (0.05% HCl)-ACN]; B %: 35%-55%, 7.8 min) to afford 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide (6.10 mg, 6.48 µmol, 5.42% yield, HCl) as a yellow solid. The product was confirmed by LC-MS and ¹H NMR.

Example 11: Preparation of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide Synthesis of S-(tetrahydropyran-4-ylmethyl) ethanethioate A mixture of 4-(bromomethyl)tetrahydropyran (300.00 mg, 1.68 mmol, 1.00 eq) and potassium thioacetate (575.62 mg, 5.04 mmol, 3.00 eq) were dissolved in DMF (10.00 mL). The resulting mixture was then stirred at 25° C. for 3 h under N₂ atmosphere. The reacting solution was quenched with sat. aq. NaHCO₃ solution (50 mL) and extracted with DCM (50 mL×3). The combined organic layers were concentrated under reduced pressure to afford S-(tetrahydropyran-4-ylmethyl) ethanethioate (245.00 mg, 1.41 mmol, 83.69% yield) as black brown oil. The product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(5-((2-(trimethylsilyl)ethoxy)methyl)pyrazolo[4,3-b]pyrrolo[3,2-e]pyridin-1(5H)-yl)benzamide The mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (100.00 mg, 105.93 µmol, 1.00 eq) and S-(tetrahydropyran-4-ylmethyl) ethanethioate (55.38 mg, 317.79 µmol, 3.00 eq) were dissolved in CH₃CN (4.00 mL), to which t-BuOK (59.43 mg, 529.65 µmol, 5.00 eq) was added in one portion. The resulting mixture was taken up into a microwave tube and heated under N₂ atmosphere at 80° C. for 2 h. The reacting solution was poured onto silica gel chromatography and eluted with pure PE to EA:MeOH=5:1. The eluent was concentrated under reduced pressure, and the residue was suspended in MeOH (4 mL) and stirred for 30 min. The precipitate was collected to afford 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(5-((2-(trimethylsilyl)ethoxy)methyl)pyrazolo[4,3-b]pyrrolo[3,2-e]pyridin-1(5H)-yl)benzamide (70.00 mg, crude) as an off-white solid. The crude product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide HCl salt: 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(5-((2-(trimethylsilyl)ethoxy)methyl)pyrazolo[4,3-b]pyrrolo[3,2-e]pyridin-1(5H)-yl)benzamide (30.00 mg, 28.85 µmol, 1.00 eq) was dissolved in DCM (5.00 mL), to which TFA (13.86 g, 121.53 mmol, 9.00 mL, 4211.98 eq) was added. The resulting mixture was then stirred at 25° C. for 14 h. After removal of the solvent, the residue was then dissolved in CH$_3$CN (5.00 mL), to which DIEA (111.87 mg, 865.58 µmol, 151.17 µL, 30.00 eq) was added in one portion. The resulting mixture was then stirred at 80° C. for 3 h, and then the solvent and excess reagent were removed under reduced pressure to afford 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide (60.00 mg, crude) as a black brown oil which was purified together with EW5403-56 by Prep-HPLC (HCl) to afford 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide HCl salt (21.40 mg, 22.62 µmol, 29.39% yield, HCl) as a yellow solid. The product was confirmed by LC-MS and $^1$H NMR.

Example 12: Preparation of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide Synthesis of 4-[4-[[2-(4-chlorophenyl)-4,4-dimethyl-cyclohexen-1-yl]methyl]piperazin-1-yl]-2-fluoro-benzonitrile A mixture of 1-[[2-(4-chlorophenyl)-4,4-dimethyl-cyclohexen-1-yl]methyl]piperazine (2.54 g, 7.15 mmol, 1.00 eq, HCl), 4-bromo-2-fluoro-benzonitrile (8.44 g, 42.21 mmol, 1.50 eq), Xantphos (6.51 g, 11.26 mmol, 0.40 eq), Pd(dba)$_2$ (3.24 g, 5.63 mmol, 0.20 eq) and Cs$_2$CO$_3$ (27.51 g, 84.42 mmol, 3.00 eq) in dioxane (300.00 mL) was stirred at 100° C. for 16 h under N$_2$ atmosphere. After removal of the solvent, the residue was purified by silica gel chromatography eluted with PE to PE:EA=5:1 to give 4-[4-[[2-(4-chlorophenyl)-4,4-dimethyl-cyclohexen-1-yl]methyl]piperazin-1-yl]-2-fluoro-benzonitrile (8.20 g, 18.72 mmol, 66.53% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile A mixture of 4-[4-[[2-(4-chlorophenyl)-4,4-dimethyl-cyclohexen-1-yl]methyl]piperazin-1-yl]-2-fluoro-benzonitrile (8.20 g, 18.72 mmol, 1.00 eq), 5-((2-(trimethylsilyl)ethoxy)methyl)-1,5-dihydropyrazolo[4,3-b]pyrrolo[3,2-e]pyridine (5.40 g, 18.72 mmol, 1.00 eq) and Cs$_2$CO$_3$ (12.20 g, 37.44 mmol, 2.00 eq) in DMF (100.00 mL) was stirred at 120° C. for 3 h. After cooling to 15° C., the mixture was filtered. The filtrate was concentrated under reduced pressure. The residue was purified by silica gel chromatography eluted with PE to PE:EA=3:1 to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (9.60 g, 13.59 mmol, 72.60% yield) as a black oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (2.60 g, 3.68 mmol, 1.00 eq) in a mixture of DMSO (30.00 mL) and EtOH (30.00 mL), KOH (412.97 mg, 7.36 mmol, 2.00 eq) in H$_2$O (10.00 mL) was added. After addition, H$_2$O$_2$ (3.34 g, 29.44 mmol, 2.83 mL, 30% purity, 8.00 eq) was added dropwise. The mixture was stirred at 25° C. for 14 h. H$_2$O (100 mL) was added to the mixture, and the mixture was extracted with EA (100 mL×3). The combined organic layers were washed with H$_2$O (500 mL), and concentrated under reduced pressure. The residue was purified by reverse phase column with TFA as additive to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.20 g, 1.66 mmol, 45.01% yield) as a yellow solid which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (500.00 mg, 690.22 µmol, 1.00 eq) in THF (10.00 mL), LiHMDS (1 M, 1.52 mL, 2.20 eq) in THF was added at 0° C. The mixture was stirred at 0° C. for 30 min, and then 4-fluoro-3-nitro-benzenesulfonyl chloride (181.92 mg, 759.24 µmol, 1.10 eq) was added. The mixture was stirred at 25° C. for 14 h. The reacting solution was quenched with sat. aq. NH$_4$Cl (50 mL) and extracted with EA (50 mL×3). The combined organic layers were concentrated under reduced pressure. The residue was purified by silica gel chromatography (pure PE to DCM:MeOH=10:1) to afford 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (90.00 mg, 97.03 µmol, 14.06% yield) as a yellow oil. The product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide A mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (20.00 mg, 21.56 μmol, 1.00 eq), (4-fluorotetrahydropyran-4-yl)-methanamine (3.99 mg, 29.97 μmol, 1.39 eq) and DIEA (27.86 mg, 215.60 μmol, 37.65 μL, 10.00 eq) in DMF (5.00 mL) was stirred at 50° C. for 14 h. The reacting solution was diluted with water (20 mL) and extracted with DCM (50 mL×3). The combined organic layers were concentrated under reduced pressure. The residue was purified by silica gel chromatography (pure PE to PE:EA=1:2) to afford 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (40.00 mg, crude) as a yellow oil. The crude product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide HCl salt: 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (40.00 mg, 38.44 μmol, 1.00 eq) was dissolved in DCM (5.00 mL), to which TFA (43.83 mg, 384.40 μmol, 28.46 μL, 10.00 eq) was added in one portion. The resulting mixture was then stirred at 25° C. for 14 h. After removal of the solvent, crude 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (30.00 mg, crude, TFA) was obtained as a yellow oil which was re-dissolved in MeCN (10.00 mL). To the solution, DIEA (36.77 mg, 284.50 μmol, 49.69 μL, 10.00 eq) was added in one portion. The resulting mixture was then stirred at 80° C. for 2 h. The solvent and excess reagent were removed under reduced pressure. The residue was purified by Prep-HPLC (HCl) to afford 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide HCl salt (6.90 mg, 7.29 μmol, 25.61% yield, HCl) as a light yellow solid which was confirmed by LC-MS and $^1$H NMR.

Example 13: Preparation of 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide Synthesis of 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide The mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 μmol, 1.00 eq) and (1-methyl-4-piperidyl)methanamine (81.49 mg, 635.58 μmol, 3.00 eq) were dissolved in CH$_3$CN (10.00 mL), to which DIEA (82.14 mg, 635.58 μmol, 111.00 μL, 3.00 eq) was added in one portion. The resulting mixture was taken up into a microwave tube and heated at 80° C. under N$_2$ atmosphere for 2 h. The reacting solution was poured onto silica gel chromatography and eluted with pure DCM to DCM:MeOH=5:1 to afford crude 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (50.00 mg, 48.27 μmol, 22.79% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-(((1-methylpiperidin-4-yl)methyl)amino)-3-nitrophenyl)sulfonyl)benzamide 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (50.00 mg, 48.27 μmol, 1.00 eq) was dissolved in DCM (10.00 mL), to which TFA (16.51 mg, 144.81 μmol, 10.72 μL, 3.00 eq) was added. The resulting mixture was then stirred at 25° C. for 1 h. The solvent and excess reagent was removed under reduced pressure to afford 4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-(((1-methylpiperidin-4-yl)methyl)amino)-3-nitrophenyl)sulfonyl)benzamide (40.00 mg, crude) as a yellow oil which was used directly in the next step.

Synthesis of 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide HCl salt: The mixture of 4-(4-((4'-chloro-5,5-dimethyl-3,4,5,6- tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-(((1-methylpiperidin-4-yl)methyl)amino)-3-nitrophenyl)sulfonyl)benzamide (40.00 mg, 42.76 µmol, 1.00 eq) and DIEA (16.58 mg, 128.28 µmol, 22.41 µL, 3.00 eq) in CH₃CN (10.00 mL) was stirred at 80° C. for 5 h. After removal of the solvent, the residue was purified by Prep-HPLC (HCl as additive) and SFC to afford 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide HCl salt (23.60 mg, 26.06 µmol, 92.19% yield) as a light yellow solid which was confirmed by LC-MS and ¹H NMR.

Example 14: Preparation of 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(pyrazolo[4,3-b]pyrrolo[3,2-e]pyridin-1(5H)-yl)benzamide Synthesis of 9H-fluoren-9-ylmethyl 4-[(tert-butoxycarbonylamino)methyl]-4-fluoro-piperidine-1-carboxylate: The mixture of tert-butyl N-[(4-fluoro-4-piperidyl)methyl]carbamate (150.00 mg, 645.74 µmol, 1.00 eq) and 9H-fluoren-9-ylmethyl carbonochloridate (250.58 mg, 968.61 µmol, 1.50 eq) were dissolved in THF (20.00 mL) and H₂O (4.00 mL), to which NaHCO₃ (162.75 mg, 1.94 mmol, 75.35 µL, 3.00 eq) was added in one portion. The resulting mixture was then stirred at 15° C. for 14 h. The reacting solution was diluted with water (50 mL) and extracted with EA (50 mL×3). The combined organic layers were concentrated under reduced pressure. The residue was purified by silica gel chromatography (pure PE to PE:EA=5:1) to afford 9H-fluoren-9-ylmethyl 4-[(tert-butoxycarbonylamino)methyl]-4-fluoro-piperidine-1-carboxylate (163.00 mg, 358.61 µmol, 55.54% yield) as an off-white solid. The product was confirmed by LC-MS and used directly for the next step without further purification.

Synthesis of 4-(aminomethyl)-4-fluoro-piperidine-1-carboxylate TFA salt: 9H-fluoren-9-ylmethyl 4-[(tert-butoxycarbonylamino)methyl]-4-fluoro-piperidine-1-carboxylate (163.00 mg, 358.61 µmol, 1.00 eq) was dissolved in DCM (10.00 mL), to which TFA (204.44 mg, 1.79 mmol, 132.76 µL, 5.00 eq) was added in one portion. The resulting mixture was then stirred at 15° C. for 14 h. The solvent and excess reagent were removed under reduced pressure to afford 9H-fluoren-9-ylmethyl 4-(aminomethyl)-4-fluoro-piperidine-1-carboxylate (200.00 mg, crude, TFA) as a yellow oil. The crude product was used directly for the next step without further purification.

Synthesis of 4-[4-[[2-(4-chlorophenyl)-4,4-dimethyl-cyclohexen-1-yl]methyl]piperazin-1-yl]-2-fluoro-benzonitrile: A mixture of 1-[[2-(4-chlorophenyl)-4,4-dimethyl-cyclohexen-1-yl]methyl]piperazine (2.54 g, 7.15 mmol, 1.00 eq, HCl), 4-bromo-2-fluoro-benzonitrile (8.44 g, 42.21 mmol, 1.50 eq), Xantphos (6.51 g, 11.26 mmol, 0.40 eq), Pd(dba)₂ (3.24 g, 5.63 mmol, 0.20 eq) and Cs₂CO₃ (27.51 g, 84.42 mmol, 3.00 eq) in dioxane (300.00 mL) was stirred at 100° C. for 16 h under N₂ atmosphere. After removal of the solvent, the residue was purified by silica gel chromatography eluted with PE to PE:EA=5:1 to give 4-[4-[[2-(4-chlorophenyl)-4,4-dimethyl-cyclohexen-1-yl]methyl]piperazin-1-yl]-2-fluoro-benzonitrile (8.20 g, 18.72 mmol, 66.53% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile: A mixture of 4-[4-[[2-(4-chlorophenyl)-4,4-dimethyl-cyclohexen-1-yl]methyl]piperazin-1-yl]-2-fluoro-benzonitrile (8.20 g, 18.72 mmol, 1.00 eq), 5-((2-(trimethylsilyl)ethoxy)methyl)-1,5-dihydropyrazolo[4,3-b]pyrrolo[3,2-e]pyridine (5.40 g, 18.72 mmol, 1.00 eq) and Cs₂CO₃ (12.20 g, 37.44 mmol, 2.00 eq) in DMF (100.00 mL) was stirred at 120° C. for 3 h. After cooling to 15° C., the mixture was filtered. The filtrate was concentrated under reduced pressure. The residue was purified by silica gel chromatography eluted with PE to PE:EA=3:1 to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (9.60 g, 13.59 mmol, 72.60% yield) as a black oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (2.60 g, 3.68 mmol, 1.00 eq) in a mixture of DMSO (30.00 mL) and EtOH (30.00 mL), KOH (412.97 mg, 7.36 mmol, 2.00 eq) in H₂O (10.00 mL) was added. After addition, H₂O₂ (3.34 g, 29.44 mmol, 2.83 mL, 30% purity, 8.00 eq) was added dropwise. The mixture was stirred at 25° C. for 14 h. H₂O (100 mL) was added to the mixture, and the mixture was extracted with EA (100 mL×3). The combined organic layers were washed with H₂O (500 mL), and concentrated under reduced pressure. The residue was purified by reverse phase column with TFA as additive to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.20 g, 1.66 mmol, 45.01% yield) as a yellow solid which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (500.00 mg, 690.22 µmol, 1.00 eq) in THF (10.00 mL), LiHMDS (1 M, 1.52 mL, 2.20 eq) in THF was added at 0° C. The mixture was stirred at 0° C. for 30 min, and then 4-fluoro-3-nitro-benzenesulfonyl chloride (181.92 mg, 759.24 µmol, 1.10 eq) was added. The mixture was stirred at 25° C. for 14 h. The reacting solution was quenched with sat. aq. NH₄Cl (50 mL) and extracted with EA (50 mL×3). The combined organic layers were concentrated under reduced pressure. The residue was purified by silica gel chromatography (pure PE to DCM:MeOH=10:1) to afford 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (90.00 mg, 97.03 µmol, 14.06% yield) as a yellow oil. The product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (250.00 mg, 269.53 µmol, 1.00 eq) and 9H-fluoren-9-ylmethyl 4-(aminomethyl)-4-fluoro-piperidine-1-carboxylate (143.29 mg, 404.29 µmol, 1.50 eq) were dissolved in DMF (50.00 mL), to which DIEA (348.34 mg, 2.70 mmol, 470.73 µL, 10.00 eq) was added in one portion. The resulting mixture was then stirred at 50° C. for 14 h. The reacting solution was diluted with water (50 mL) and extracted with DCM (50 mL×3). The combined organic layers were concentrated under reduced pressure to afford crude (9H-fluoren-9-yl)methyl 4-(((4-(N-(4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoyl)sulfamoyl)-2-nitrophenyl)amino)methyl)-4-fluoropiperidine-1-carboxylate (400.00 mg, crude) as a yellow oil which was re-dissolved in DMF (20.00 mL). To the above solution, piperidine (134.95 mg, 1.58 mmol, 156.92 µL, 5.00 eq) was added in one portion. The resulting mixture was then stirred at 15° C. for 14 h. The reacting solution was poured onto silica gel chromatography and eluted with pure PE to DCM:MeOH=5:1 to afford 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (268.00 mg, 257.76 µmol, 81.32% yield) as a yellow oil which was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide: 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (268.00 mg, 257.76 µmol, 1.00 eq) was dissolved in DCM (20.00 mL), to which TFA (146.95 mg, 1.29 mmol, 95.42 µL, 5.00 eq) was added in one portion. The resulting mixture was then stirred at 15° C. for 14 h. The solvent and excess reagent were removed under reduced pressure to afford 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (240.00 mg, crude) as a yellow oil which was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(pyrazolo[4,3-b]pyrrolo[3,2-e]pyridin-1(5H)-yl)benzamide 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (120.00 mg, 127.73 µmol, 1.00 eq) and oxetan-3-one (27.61 mg, 383.19 µmol, 3.00 eq) were dissolved in MeOH (10.00 mL), to which NaBH$_3$CN (40.13 mg, 638.65 µmol, 5.00 eq) was added in one portion. The resulting mixture was then stirred at 15° C. for 14 h. The reacting solution was diluted with water (50 mL) and extracted with DCM (50 mL×3). The combined organic layers were concentrated under reduced pressure to afford crude 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (120.00 mg, crude) as a yellow oil which was re-dissolved in CH$_3$CN (20.00 mL). To the above solution DIEA (77.89 mg, 602.70 µmol, 105.26 µL, 5.00 eq) was added in one portion. The resulting mixture was then stirred under N$_2$ atmosphere at 80° C. for 14 h. The reacting solution was diluted with water (50 mL) and extracted with DCM (50 mL×3). The combined organic layers were concentrated under reduced pressure. The residue was purified by Prep-TLC (EA/MeOH=10:1 and then EA:MeOH=5:1) to afford 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(pyrazolo[4,3-b]pyrrolo[3,2-e]pyridin-1(5H)-yl)benzamide (2.80 mg, 2.90 µmol, 2.41% yield) as a yellow solid. The product was confirmed by LC-MS and $^1$H NMR.

Example 15: Preparation of (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide Synthesis of 9H-fluoren-9-ylmethyl (2R)-2-[(tert-butoxycarbonylamino)methyl]morpholine-4-carboxylate: A mixture of tert-butyl N-[[(2S)-morpholin-2-yl]methyl]carbamate (64.00 mg, 295.91 µmol, 1.00 eq), Fmoc-Cl (114.83 mg, 443.87 µmol, 1.50 eq) and Na$_2$CO$_3$ (94.09 mg, 887.74 µmol, 3.00 eq) in a mixture of THF (10.00 mL) and H$_2$O (2.00 mL) was stirred at 20° C. for 12 h. The mixture was extracted with EA (20 mL×3), and the combined organic layers were concentrated under reduced pressure. The residue was purified by Prep-TLC (PE:EA=3:1) to give 9H-fluoren-9-ylmethyl (2R)-2-[(tert-butoxycarbonylamino)methyl]morpholine-4-carboxylate (111.00 mg, 253.13 µmol, 85.54% yield) as a colorless oil which was confirmed by LC-MS.

Synthesis of 9H-fluoren-9-ylmethyl (2R)-2-(aminomethyl)morpholine-4-carboxylate TFA salt: A mixture of 9H-fluoren-9-ylmethyl (2R)-2-[(tert-butoxycarbonylamino)methyl]morpholine-4-carboxylate (111.00 mg, 253.12 µmol, 1.00 eq) and TFA (577.21 mg, 5.06 mmol, 374.81 µL, 20.00 eq) in DCM (10.00 mL) was stirred at 15° C. for 3 h. After removal of the solvent, crude 9H-fluoren-9-ylmethyl (2R)-2-(aminomethyl)morpholine-4-carboxylate TFA salt (80.00 mg) was obtained as a light yellow oil which was used directly in the next step.

Synthesis of 4-[4-[[2-(4-chlorophenyl)-4,4-dimethyl-cyclohexen-1-yl]methyl]piperazin-1-yl]-2-fluoro-benzonitrile: A mixture of 1-[[2-(4-chlorophenyl)-4,4-dimethyl-cyclohexen-1-yl]methyl]piperazine (2.54 g, 7.15 mmol, 1.00 eq, HCl), 4-bromo-2-fluoro-benzonitrile (8.44 g, 42.21 mmol, 1.50 eq), Xantphos (6.51 g, 11.26 mmol, 0.40 eq), Pd(dba)$_2$ (3.24 g, 5.63 mmol, 0.20 eq) and Cs$_2$CO$_3$ (27.51 g, 84.42 mmol, 3.00 eq) in dioxane (300.00 mL) was stirred at 100° C. for 16 h under N$_2$ atmosphere. After removal of the solvent, the residue was purified by silica gel chromatography eluted with PE to PE:EA=5:1 to give 4-[4-[[2-(4-chlorophenyl)-4,4-dimethyl-cyclohexen-1-yl]methyl]piperazin-1-yl]-2-fluoro-benzonitrile (8.20 g, 18.72 mmol, 66.53% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile: A mixture of 4-[4-[[2-(4-chlorophenyl)-4,4-dimethyl-cyclohexen-1-yl]methyl]piperazin-1-yl]-2-fluoro-benzonitrile (8.20 g, 18.72 mmol, 1.00 eq), 5-((2-(trimethylsilyl)ethoxy)methyl)-1,5-dihydro-pyrazolo[4,3-b]pyrrolo[3,2-e]pyridine (5.40 g, 18.72 mmol, 1.00 eq) and Cs$_2$CO$_3$ (12.20 g, 37.44 mmol, 2.00 eq) in DMF (100.00 mL) was stirred at 120° C. for 3 h. After cooling to 15° C., the mixture was filtered. The filtrate was concentrated under reduced pressure. The residue was purified by silica gel chromatography eluted with PE to PE:EA=3:1 to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (9.60 g, 13.59 mmol, 72.60% yield) as a black oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (2.60 g, 3.68 mmol, 1.00 eq) in a mixture of DMSO (30.00 mL) and EtOH (30.00 mL), KOH (412.97 mg, 7.36 mmol, 2.00 eq) in H$_2$O (10.00 mL) was added. After addition, H$_2$O$_2$ (3.34 g, 29.44 mmol, 2.83 mL, 30% purity, 8.00 eq) was added dropwise. The mixture was stirred at 25° C. for 14 h. H$_2$O (100 mL) was added to the mixture, and the mixture was extracted with EA (100 mL×3). The combined organic layers were washed with H$_2$O (500 mL), and concentrated under reduced pressure. The residue was purified by reverse phase column with TFA as additive to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.20 g, 1.66 mmol, 45.01% yield) as a yellow solid which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (500.00 mg, 690.22 µmol, 1.00 eq) in THF (10.00 mL), LiHMDS (1 M, 1.52 mL, 2.20 eq) in THF was added at 0° C. The mixture was stirred at 0° C. for 30 min, and then 4-fluoro-3-nitro-benzenesulfonyl chloride (181.92 mg, 759.24 µmol, 1.10 eq) was added. The mixture was stirred at 25° C. for 14 h. The reacting solution was quenched with sat. aq. NH$_4$Cl (50 mL) and extracted with EA (50 mL×3). The combined organic layers were concentrated under reduced pressure. The residue was purified by silica gel chromatography (pure PE to DCM:MeOH=10:1) to afford 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (90.00 mg, 97.03 µmol, 14.06% yield) as a yellow oil. The product was confirmed by LC-MS and used directly for the next step without further purification.

Synthesis of (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: A mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (80.00 mg, 86.25 µmol, 1.00 eq), 9H-fluoren-9-ylmethyl (2R)-2-(aminomethyl)morpholine-4-carboxylate (67.13 mg, 198.38 µmol, 2.30 eq) and DIEA (55.73 mg, 431.25 µmol, 75.31 µL, 5.00 eq) in DMF (10.00 mL) was stirred at 50° C. under N$_2$ atmosphere for 14 h. The reacting solution was diluted with water (20 mL) and extracted with DCM (50 mL×3). The combined organic layers were concentrated under reduced pressure to afford (R)-(9H-fluoren-9-yl)methyl 2-(((4-(N-(4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoyl)sulfamoyl)-2-nitrophenyl)amino)methyl)morpholine-4-carboxylate (100.00 mg, crude) as a yellow oil. Next, (R)-(9H-fluoren-9-yl)methyl 2-(((4-(N-(4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoyl)sulfamoyl)-2-nitrophenyl)amino)methyl)morpholine-4-carboxylate (130.00 mg, 104.34 µmol, 1.00 eq) was dissolved in DMF (20.00 mL), to which piperidine (88.85 mg, 1.04 mmol, 103.31 µL, 10.00 eq) was added in one portion. The resulting mixture was then stirred at 15° C. for 14 h. The reacting solution was poured onto silica gel chromatography (pure PE to DCM:MeOH=5:1) to afford (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (100.00 mg, crude) as a yellow oil. The crude product was confirmed by LC-MS and used directly for the next step without further purification.

Synthesis of (S)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-((morpholin-2-ylmethyl)amino)-3-nitrophenyl)sulfonyl)benzamide: (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (100.00 mg, 97.68 µmol, 1.00 eq) was dissolved in DCM (20.00 mL), to which TFA (111.38 mg, 976.84 µmol, 72.32 µL, 10.00 eq) was added in one portion. The resulting mixture was then stirred at 15° C. for 14 h. The solvent and excess reagent were removed under reduced pressure to afford (S)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-((morpholin-2-ylmethyl)amino)-3-nitrophenyl)sulfonyl)benzamide (100.00 mg, crude, TFA) as a yellow oil. The crude product was used directly for the next step without further purification.

Synthesis of (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide: (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide: The mixture of (S)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-((morpholin-2-ylmethyl)amino)-3-nitrophenyl)sulfonyl)benzamide (100.00 mg, 108.29 µmol, 1.00 eq) and oxetan-3-one (23.41 mg, 324.87 µmol, 3.00 eq) were dissolved in MeOH (20.00 mL), to which NaBH$_3$CN (20.41 mg, 324.87 µmol, 3.00 eq) was added in one portion. The resulting mixture was then stirred at 15° C. under N$_2$ atmosphere for 14 h. The reacting solution was diluted with water (20 mL) and extracted with DCM (50 mL×3). The combined organic layers were concentrated under reduced pressure to afford crude (R)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((3-nitro-4-(((4-(oxetan-3-yl)morpholin-2-yl)methyl)amino)phenyl)sulfonyl)benzamide (100.00 mg, crude) as a yellow oil which was then suspended in CH$_3$CN (20.00 mL). To the above solution, DIEA (131.94 mg, 1.02 mmol, 178.30 µL, 10.00 eq) was added in one portion. The resulting mixture was then stirred at 80° C. for 14 h. The solvent and excess reagent were removed under reduced pressure. The residue was purified by Prep-HPLC (neutral) to afford (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide (1.10 mg, 1.16 µmol, 1.13% yield) as a yellow solid. The product was confirmed by LC-MS and $^1$H NMR. 11 mg of crude product was also obtained.

Example 16: Preparation of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1(5H)-yl)benzamide Synthesis of Tert-butyl ((4-fluoro-1-methylpiperidin-4-yl)methyl)carbamate: A mixture of tert-butyl ((4-fluoropiperidin-4-yl)methyl)carbamate (330.00 mg, 1.42 mmol, 1.00 eq) and aq. HCHO (37%, 172.88 mg, 2.13 mmol, 158.61 µL, 1.50 eq) in CH$_3$CN (10.00 mL) was stirred at 30° C. for 30 min, and then NaBH$_3$CN (178.47 mg, 2.84 mmol, 2.00 eq) and AcOH (104.88 mg, 1.75 mmol, 99.89 µL, 1.23 eq) were added in portions. The mixture was stirred at 15° C. for 13.5 h. The reacting solution was diluted with water (100 mL) and extracted with EA (100 mL×4). The combined organic layers were concentrated under reduced pressure and purified by silica gel chromatography (PE:EA=1:1 to EA:MeOH=5:1) to afford tert-butyl ((4-fluoro-1-methylpiperidin-4-yl)methyl)carbamate (290.00 mg, 1.18 mmol, 82.91% yield) as a colorless oil, which was confirmed by LC-MS.

Synthesis of (4-fluoro-1-methylpiperidin-4-yl)methanamine: Tert-butyl ((4-fluoro-1-methylpiperidin-4-yl)methyl)carbamate (290.00 mg, 1.18 mmol, 1.00 eq) was dissolved in DCM (10.00 mL), to which TFA (3.08 g, 27.01 mmol, 2.00 mL, 22.89 eq) was added in portions. The resulting mixture was then stirred at 15° C. for 15 h. The solvent and excess reagent were removed under reduced pressure to afford (4-fluoro-1-methylpiperidin-4-yl)methanamine (320.00 mg, crude) as a yellow oil.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (140.00 mg, 150.94 µmol, 1.00 eq) and (4-fluoro-1-methylpiperidin-4-yl)methanamine (66.21 mg, 452.82 µmol, 3.00 eq) were dissolved in DMF (20.00 mL), to which DIEA (195.07 mg, 1.51 mmol, 263.61 µL, 10.00 eq) was added in one portion. The resulting mixture was then stirred under N$_2$ atmosphere at 50° C. for 14 h. The solvent and excess reagent were removed under reduced pressure. The residue was purified by silica gel chromatography (pure DCM to DCM:MeOH=3:1) to afford 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (141.00 mg, 133.81 µmol, 88.65% yield) as a yellow oil, which was confirmed by LC-MS. LC-MS: EW5403-312-P1A00 (M+H+=1054, M/2+H+=527).

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide: 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (141.00 mg, 133.81 µmol, 1.00 eq) was dissolved in DCM (10.00 mL), to which TFA (152.57 mg, 1.34 mmol, 99.07 µL, 10.00 eq) was added in one portion. The resulting mixture was then stirred at 15° C. for 14 h. The solvent and excess reagent were removed under reduced pressure to afford 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (150.00 mg, crude) as a yellow oil, which was confirmed by LC-MS. LC-MS: EW5403-317-P1Z (M+H+=953).

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1 (5H)-yl)benzamide: 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (150.00 mg, 157.31 µmol, 1.00 eq) and DIEA (203.31 mg, 1.57 mmol, 274.74 µL, 10.00 eq) were dissolved in $CH_3CN$ (20.00 mL). The resulting mixture was then stirred at 80° C. under $N_2$ atmosphere for 14 h. The solvent and excess reagent were removed under reduced pressure. The residue was purified by column: Phenomenex Synergi $C_{18}$ 150*25*10 µm; mobile phase: [water (0.05% HCl)-ACN]; B %: 42%-62%, 7.8 min to afford 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1 (5H)-yl)benzamide (1.8 mg, 1.95 µmol, 1.24% yield) as a yellow solid, which was confirmed by LC-MS and $^1$H NMR. LC-MS: EW5403-318-P1B (M+H$^+$=924, M/2+H$^+$=462). $^1$H NMR: EW5403-318-P1A0 400 MHz DMSO-d$_6$, δ 11.43 (brs, 1H), 10.65 (brs, 1H), 8.54 (s, 1H), 8.30 (s, 1H), 8.05 (s, 1H), 7.77 (s, 1H), 7.36-7.59 (m, 4H), 7.07-7.09 (m, 3H), 6.95-6.97 (m, 2H), 6.30 (s, 1H), 3.71-3.77 (m, 2H), 3.24-3.27 (m, 3H), 3.03-3.17 (m, 3H), 2.87-2.89 (m, 2H), 2.10-2.12 (m, 4H), 2.21-2.50 (m, 4H), 1.99 (s, 3H), 1.41-1.45 (m, 2H), 1.16-1.23 (m, 6H), 0.95 (s, 6H).

Example 17: Preparation of 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-nitrophenyl)sulfonyl)-2-(pyrazolo[4,3-b]pyrrolo[3,2-e]pyridin-1(5H)-yl)benzamide Step 1: Tert-butyl 4-fluoro-4-((2-nitro-4-sulfamoylphenoxy)methyl)piperidine-1-carboxylate: The mixture of 4-fluoro-3-nitro-benzenesulfonamide (300.00 mg, 1.36 mmol, 1.00 eq) and tert-butyl 4-fluoro-4-(hydroxymethyl)piperidine-1-carboxylate (317.26 mg, 1.36 mmol, 1.00 eq) were dissolved in THF (50.00 mL), to which NaH (163.20 mg, 4.08 mmol, 60% purity, 3.00 eq) was added at 0° C. in one portion. The resulting mixture was then stirred at 15° C. for 14 h. The reacting solution was quenched with EtOH (10 mL), diluted with water (50 mL) and extracted with DCM (100 mL×3). The combined organic layers were concentrated under reduced pressure and purified together with EW5403-280-P1 by silica gel chromatography (pure PE to PE:EA=1:1) to afford tert-butyl 4-fluoro-4-((2-nitro-4-sulfamoylphenoxy)methyl)piperidine-1-carboxylate (560 mg, 1.29 mmol, 85.69% yield) as an off-white solid, which was confirmed by LC-MS. LC-MS: EW5403-286-P1A0 (M+Na$^+$=456).

Step 2: 4-((4-fluoropiperidin-4-yl)methoxy)-3-nitrobenzenesulfonamide Tert-butyl 4-fluoro-4-((2-nitro-4-sulfamoylphenoxy)methyl)piperidine-1-carboxylate (100.00 mg, 230.71 µmol, 1.00 eq) was dissolved in DCM (20.00 mL), to which TFA (131.53 mg, 1.15 mmol, 85.41 µL, 5.00 eq) was added in one portion. The resulting mixture was then stirred at 15° C. for 14 h. The solvent and excess reagent were removed under reduced pressure to afford 4-((4-fluoropiperidin-4-yl)methoxy)-3-nitrobenzenesulfonamide (80 mg, crude) as an off-white solid. LC-MS: EW5403-287-P1Z0 (M+H$^+$=334).

Step 3: 4-((4-fluoro-1-(oxetan-3-yl)piperidin-4-yl)methoxy)-3-nitrobenzenesulfonamide: The mixture of 4-[(4-fluoro-4-piperidyl)methoxy]-3-nitro-benzenesulfonamide (70.00 mg, 156.47 µmol, 1.00 eq, TFA) and oxetan-3-one (67.65 mg, 938.82 µmol, 6.00 eq) were dissolved in MeOH (10.00 mL), to which NaBH$_3$CN (98.33 mg, 1.56 mmol, 10.00 eq) was added in one portion. The resulting mixture was then stirred at 15° C. for 14 h. The solvent and excess reagent were removed under reduced pressure. The residue was purified together with EW5403-288-P1 by silica gel chromatography (pure DCM to DCM:MeOH=10:1) to afford 4-((4-fluoro-1-(oxetan-3-yl)piperidin-4-yl)methoxy)-3-nitrobenzenesulfonamide (100 mg, crude) as a light yellow oil, which was confirmed by LC-MS. LC-MS: EW5403-289-P1A2 (M+H$^+$=390).

Step 4: The synthesis of 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-nitrophenyl)sulfonyl)-2-(pyrazolo[4,3-b]pyrrolo[3,2-e]pyridin-1(5H)-yl)benzamide: 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-nitrophenyl)sulfonyl)-2-(pyrazolo[4,3-b]pyrrolo[3,2-e]pyridin-1(5H)-yl)benzamide: The mixture of 4-[[4-fluoro-1-(oxetan-3-yl)-4-piperidyl]methoxy]-3-nitro-benzenesulfonamide (50.00 mg, 128.40 µmol, 1.00 eq), 4-[4-[[2-(4-chlorophenyl)-4,4-dimethyl-cyclohexen-1-yl]methyl]piperazin-1-yl]-2-(5H-pyrazolo[BLAH]pyrrolo[BLAH]pyridin-1-yl)benzoic acid (76.42 mg, 128.40 µmol, 1.00 eq), DMAP (31.37 mg, 256.81 µmol, 2.00 eq) and EDCI (49.23 mg, 256.81 µmol, 2.00 eq) were dissolved in DCM (20.00 mL). The resulting mixture was then stirred at 15° C. for 14 h. The reacting solution was poured onto silica gel chromatography and eluted with DCM to DCM:MeOH=5:1, and then purified by column: Phenomenex Synergi C18 150*25*10 µm; mobile phase: [water (0.05% HCl)-ACN]; B %: 42%-62%, 7.8 min to afford 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-nitrophenyl)sulfonyl)-2-(pyrazolo[4,3-b]pyrrolo[3,2-e]pyridin-1(5H)-yl)benzamide (8.4 mg, 8.69 µmol, 6.8% yield) as a light yellow solid, which was confirmed by LC-MS and $^1$H NMR. LC-MS: EW5403-300-P1C0 (M/2+H$^+$=483). $^1$H NMR: EW5403-300-P1A0 400 MHz CD$_3$OD, δ 8.26 (s, 1H), 8.18 (s, 2H), 7.99-8.00 (m, 1H), 7.67-7.70 (m, 1H), 7.65 (s, 1H), 7.15-7.37 (m, 7H), 6.52 (s, 1H), 4.44-4.49 (m, 2H), 4.12-4.18 (m, 3H), 3.95 (s, 2H), 3.54-3.82 (m, 8H), 3.35 (m, 2H), 2.90 (s, 3H), 2.38-2.49 (m, 6H), 2.14 (s, 2H), 1.60 (s, 2H), 1.29 (s, 1H), 1.03 (s, 6H).

Example 18: Preparation of 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide Step 1: the synthesis of 3-nitro-4-((tetrahydro-2H-pyran-4-yl)methoxy)benzenesulfonamide: To a solution of (tetrahydro-2H-pyran-4-yl)methanol (263.68 mg, 2.27 mmol, 1.00 eq) in THF (20.00 mL), NaH (272.40 mg, 6.81 mmol, 60% purity, 3.00 eq) was added at 0° C. The mixture was stirred at 0° C. for 30 min, and then 4-fluoro-3-nitrobenzenesulfonamide (500.00 mg, 2.27 mmol, 1.00 eq) was added. The mixture was stirred at 25° C. for 15 h, and then the reaction mixture was quenched by MeOH (10 mL). After removal of the solvent, the residue was purified by silica gel chromatography eluted with PE:EA=5:1 to 1:1 to give 3-nitro-4-((tetrahydro-2H-pyran-4-yl)methoxy)benzenesulfonamide (446.00 mg, 1.41 mmol, 62.11% yield) as yellow solid which was confirmed by LC-MS. LC-MS: EW6259-87-P1A2 (M+H+=317.0).

Step 2, the synthesis of 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide: 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide: To a mixture of 3-nitro-4-((tetrahydro-2H-pyran-4-yl)methoxy)benzenesulfonamide (296.00 mg, 935.73 µmol, 1.50 eq) and 4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzoic acid (371.25 mg, 623.82 µmol, 1.00 eq) in THF (20.00 mL) was added EDCI (358.76 mg, 1.87 mmol, 3.00 eq) and DMAP (228.64 mg, 1.87 mmol, 3.00 eq). The mixture was stirred at 25° C. for 12 h. After removal of the solvent, the residue was purified together with EW6259-90 by Prep-HPLC (column: Phenomenex Synergi $C_{18}$ 150*25*10 µm; mobile phase: [water (0.05% HCl)-ACN]; B %: 38%-58%, 7.8 min) to give 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide (68.4 mg, 50.81 µmol, 8.15% yield) as yellow solid which was confirmed by LC-MS and $^1$H NMR. LC-MS: EW6259-91-P1G (M+H$^+$=893.2) 1HNMR: EW6259-91-P1P 400 MHz CD$_3$OD, δ 8.43 (s, 1H), 8.22 (s, 1H), 8.17 (d, J=2.0 Hz, 1H), 8.01-8.04 (m, 1H), 7.69-7.71 (m, 2H), 7.33-7.39 (m, 3H), 7.24 (s, 1H), 7.13-7.15 (m, 3H), 6.64-6.65 (m, 1H), 4.11-4.13 (m, 2H), 3.75-4.04 (m, 5H), 3.75 (s, 2H), 3.54-3.56 (m, 2H), 3.48-3.51 (m, 2H), 3.31-3.41 (m, 2H), 2.39 (s, 2H), 2.14-2.17 (m, 3H), 1.80-1.83 (m, 2H), 1.52-1.59 (m, 5H), 1.03 (s, 6H).

The compounds below are prepared by methods substantially identical, similar, or analogous to those disclosed in Scheme A-C and above examples:

| Example No. | Chemical Name | m/z(MH$^+$) |
| --- | --- | --- |
| 19 | 4-(4-((4'-chloro-5,5-dimethyl-3,4,5,6-tetrahydro-[1,1'-biphenyl]-2-yl)methyl)piperazin-1-yl)-N-((4-((4-fluoro-1-methylpiperidin-4-yl)methoxy)-3-nitrophenyl)sulfonyl)-2-(pyrazolo[4,3-b]pyrrolo[3,2-e]pyridin-1(5H)-yl)benzamide | 923 |
| 20 | 4-(4-((4'-chloro-5,5-dimethyl-3,4,5,6-tetrahydro-[1,1'-biphenyl]-2-yl)methyl)piperazin-1-yl)-N-((4-((4-fluoropiperidin-4-yl)methoxy)-3-nitrophenyl)sulfonyl)-2-(pyrazolo[4,3-b]pyrrolo[3,2-e]pyridin-1(5H)-yl)benzamide | 910 |
| 21 | 4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(pyrazolo[4,3-b]pyrrolo[3,2-e]pyridin-1(5H)-yl)benzamide | 893 |
| 22 | 4-(4-((4'-chloro-5,5-dimethyl-3,4,5,6-tetrahydro-[1,1'-biphenyl]-2-yl)methyl)piperazin-1-yl)-N-((4-(((4-methylmorpholin-2-yl)methyl)amino)-3-nitrophenyl)sulfonyl)-2-(pyrazolo[4,3-b]pyrrolo[3,2-e]pyridin-1(5H)-yl)benzamide | 907 |
| 23 | 4-(4-((4'-chloro-5,5-dimethyl-3,4,5,6-tetrahydro-[1,1'-biphenyl]-2-yl)methyl)piperazin-1-yl)-N-((4-(((4-hydroxy-4-methylcyclohexyl)methyl)amino)-3-nitrophenyl)sulfonyl)-2-(pyrazolo[4,3-b]pyrrolo[3,2-e]pyridin-1(5H)-yl)benzamide | 920 |
| 24 | 4-(4-((4'-chloro-5,5-dimethyl-3,4,5,6-tetrahydro-[1,1'-biphenyl]-2-yl)methyl)piperazin-1-yl)-N-((4-((4-fluorotetrahydro-2H-pyran-4-yl)methoxy)-3-nitrophenyl)sulfonyl)-2-(pyrazolo[4,3-b]pyrrolo[3,2-e]pyridin-1(5H)-yl)benzamide | 911 |
| 25 | 4-(4-((4'-chloro-5,5-dimethyl-3,4,5,6-tetrahydro-[1,1'-biphenyl]-2-yl)methyl)piperazin-1-yl)-N-((4-((4-hydroxy-4-methylcyclohexyl)methoxy)-3-nitrophenyl)sulfonyl)-2-(pyrazolo[4,3-b]pyrrolo[3,2-e]pyridin-1(5H)-yl)benzamide | 921 |
| 26 | N-((3-chloro-4-((4-fluoro-1-(oxetan-3-yl)piperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide | 955 |
| 27 | N-((3-chloro-4-((4-fluoro-1-methylpiperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide | 913 |
| 28 | 4-(4-((4'-chloro-5,5-dimethyl-3,4,5,6-tetrahydro-[1,1'-biphenyl]-2-yl)methyl)piperazin-1-yl)-N-((4-((4-morpholinocyclohexyl)amino)-3-nitrophenyl)sulfonyl)-2-(pyrazolo[4,3-b]pyrrolo[3,2-e]pyridin-1(5H)-yl)benzamide | 961 |

-continued

| Example No. | Chemical Name | m/z(MH+) |
|---|---|---|
| 29 | 4-(4-((4'-chloro-5,5-dimethyl-3,4,5,6-tetrahydro-[1,1'-biphenyl]-2-yl)methyl)piperazin-1-yl)-N-((4-(((4-hydroxycyclohexyl)methyl)amino)-3-nitrophenyl)sulfonyl)-2-(pyrazolo[4,3-b]pyrrolo[3,2-e]pyridin-1(5H)-yl)benzamide | 906 |
| 30 | 4-(4-((4'-chloro-5,5-dimethyl-3,4,5,6-tetrahydro-[1,1'-biphenyl]-2-yl)methyl)piperazin-1-yl)-N-((4-(((4-methoxycyclohexyl)methyl)amino)-3-nitrophenyl)sulfonyl)-2-(pyrazolo[4,3-b]pyrrolo[3,2-e]pyridin-1(5H)-yl)benzamide | 920 |
| 31 | 4-(4-((4'-chloro-5,5-dimethyl-3,4,5,6-tetrahydro-[1,1'-biphenyl]-2-yl)methyl)piperazin-1-yl)-N-((4-(((1-(methylsulfonyl)pyrrolidin-3-yl)amino)-3-nitrophenyl)sulfonyl)-2-(pyrazolo[4,3-b]pyrrolo[3,2-e]pyridin-1(5H)-yl)benzamide | 941 |
| 32 | 4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydro-2H-pyran-4-yl)pyrrolidin-3-yl)methyl)amino)phenyl)sulfonyl)-2-(pyrazolo[4,3-b]pyrrolo[3,2-e]pyridin-1(5H)-yl)benzamide | 961 |
| 33 | 4-(4-((4'-chloro-5,5-dimethyl-3,4,5,6-tetrahydro-[1,1'-biphenyl]-2-yl)methyl)piperazin-1-yl)-N-((4-((4-morpholinocyclohexyl)oxy)-3-nitrophenyl)sulfonyl)-2-(pyrazolo[4,3-b]pyrrolo[3,2-e]pyridin-1(5H)-yl)benzamide | 962 |
| 34 | 4-(4-((4'-chloro-5,5-dimethyl-3,4,5,6-tetrahydro-[1,1'-biphenyl]-2-yl)methyl)piperazin-1-yl)-N-((4-((4-hydroxycyclohexyl)methoxy)-3-nitrophenyl)sulfonyl)-2-(pyrazolo[4,3-b]pyrrolo[3,2-e]pyridin-1(5H)-yl)benzamide | 907 |
| 35 | 4-(4-((4'-chloro-5,5-dimethyl-3,4,5,6-tetrahydro-[1,1'-biphenyl]-2-yl)methyl)piperazin-1-yl)-N-((4-((4-methoxycyclohexyl)methoxy)-3-nitrophenyl)sulfonyl)-2-(pyrazolo[4,3-b]pyrrolo[3,2-e]pyridin-1(5H)-yl)benzamide | 921 |
| 36 | 4-(4-((4'-chloro-5,5-dimethyl-3,4,5,6-tetrahydro-[1,1'-biphenyl]-2-yl)methyl)piperazin-1-yl)-N-((4-((4-hydroxy-4-methylcyclohexyl)methoxy)-3-nitrophenyl)sulfonyl)-2-(pyrazolo[4,3-b]pyrrolo[3,2-e]pyridin-1(5H)-yl)benzamide | 921 |
| 37 | 4-(4-((4'-chloro-5,5-dimethyl-3,4,5,6-tetrahydro-[1,1'-biphenyl]-2-yl)methyl)piperazin-1-yl)-N-((4-(((1-(methylsulfonyl)pyrrolidin-3-yl)oxy)-3-nitrophenyl)sulfonyl)-2-(pyrazolo[4,3-b]pyrrolo[3,2-e]pyridin-1(5H)-yl)benzamide | 942 |
| 38 | 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)pyrrolidin-3-yl)methoxy)phenyl)sulfonyl)-2-(pyrazolo[4,3-b]pyrrolo[3,2-e]pyridin-1(5H)-yl)benzamide | 962 |
| 39 | 4-(4-((4'-chloro-5,5-dimethyl-3,4,5,6-tetrahydro-[1,1'-biphenyl]-2-yl)methyl)piperazin-1-yl)-N-((4-((4-methylmorpholin-2-yl)methoxy)-3-nitrophenyl)sulfonyl)-2-(pyrazolo[4,3-b]pyrrolo[3,2-e]pyridin-1(5H)-yl)benzamide | 908 |
| 40 | 4-(4-((4'-chloro-5,5-dimethyl-3,4,5,6-tetrahydro-[1,1'-biphenyl]-2-yl)methyl)piperazin-1-yl)-N-((4-(((4,4-difluorocyclohexyl)methyl)amino)-3-nitrophenyl)sulfonyl)-2-(pyrazolo[4,3-b]pyrrolo[3,2-e]pyridin-1(5H)-yl)benzamide | 926 |
| 41 | 4-(4-((4'-chloro-5,5-dimethyl-3,4,5,6-tetrahydro-[1,1'-biphenyl]-2-yl)methyl)piperazin-1-yl)-N-((3-nitro-4-((((1,4,4-trifluorocyclohexyl)methyl)amino)phenyl)sulfonyl)-2-(pyrazolo[4,3-b]pyrrolo[3,2-e]pyridin-1(5H)-yl)benzamide | 944 |
| 42 | 4-(4-((4'-chloro-5,5-dimethyl-3,4,5,6-tetrahydro-[1,1'-biphenyl]-2-yl)methyl)piperazin-1-yl)-N-((4-((4,4-difluorocyclohexyl)methoxy)-3-nitrophenyl)sulfonyl)-2-(pyrazolo[4,3-b]pyrrolo[3,2-e]pyridin-1(5H)-yl)benzamide | 927 |
| 43 | 4-(4-((4'-chloro-5,5-dimethyl-3,4,5,6-tetrahydro-[1,1'-biphenyl]-2-yl)methyl)piperazin-1-yl)-N-((3-nitro-4-((1,4,4-trifluorocyclohexyl)methoxy)phenyl)sulfonyl)-2-(pyrazolo[4,3-b]pyrrolo[3,2-e]pyridin-1(5H)-yl)benzamide | 945 |

Biological Example 1: Bcl-2 Competition Binding (Fluorescence Polarization) Assay The fluorescence-labeled 23 amino acid peptide BH3 was purchased from CalBiochem (NLWAAQRYGRELRRMS-DKFVD, SEQ ID NO: 1). An unbound Fluorescein labeled BH3 peptide emits random light with respect to the plane of polarization plane of excited light, resulting in a lower polarization degree (mP) value. When the peptide is bound to Bcl-2, the complex tumble slower and the emitted light can have a higher level of polarization, resulting in a higher mP value. This binding assay was performed in 96-well plate and with each assay contained 15 and 30 nM of labeled peptide and purified Bcl-2 protein (purchased from R&D Systems, Inc). The assay buffer contained 20 mM Hepes (pH 7.0), 50 mM KCl, 5 mM MgCl$_2$, 20 mM Na$_2$MoO$_4$, 0.1 mg/ml Bovine Gamma Globulin and 0.01% NP40. Compounds were diluted in DMSO and added to the final assay with concentration range from 20 uM to 2 nM. The polarization degree (mP) value was determined by BioTek Synergy II with background subtraction after 3 hours of incubation at room temperature. IC$_{50}$ was calculated using Prism software with sigmoidal dose-response curve fitting. ABT-737 was used as reference compound. Such assays, carried out with a range of doses of test compounds, allow the determination of an approximate IC$_{50}$ value. Although the inhibitory properties of the compounds of the present invention vary with structural change as expected, the activity generally exhibited by these agents is in the range of IC$_{50}$=0.1-1000 nM. The following table lists the IC$_{50}$ values of certain compounds of the invention.

| Example No. | BCL-2 |
| --- | --- |
| ABT-199 | <10 nM |
| ABT-263 | <10 nM |
| 4 | <10 nM |
| 6 | <10 nM |
| 7 | <10 nM |
| 8 | <10 nM |
| 12 | <10 nM |
| 13 | <10 nM |
| 16 | <10 nM |
| 11 | <10 nM |
| 14 | <10 nM |
| 17 | <10 nM |
| 15 | <10 nM |
| 19 | <10 nM |
| 18 | <10 nM |

Biological Example 2: In Vitro Anti-Proliferation Assay in BCL-2-Dependent Acute Lymphoblastic Leukemia Cell Line RS4;11

Cell antiproliferation is assayed by PerkinElmer ATPlite™ Luminescence Assay System. Briefly, the various test cancer cell lines are plated at a density of about 1×10$^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 μL of mammalian cell lysis solution is added to 100 μL of cell suspension per well of a microplate, and the plate is shaken for about five minutes in an orbital shaker at ~700 rpm. This procedure is used to lyse the cells and to stabilize the ATP. Next, 50 μL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative IC$_{50}$ of the compounds of the present invention. The following table lists the IC$_{50}$ values of certain compounds of the invention.

| Example No. | RS4; 11 IC$_{50}$ |
| --- | --- |
| 4 | <15 nM |
| 12 | <15 nM |

Biological Example 3: In Vitro Anti-Proliferation Assay in BCL-XL-Dependent Lines Small Cell Lung Cancer Cell Line H146

Cell antiproliferation is assayed by PerkinElmer ATPlite™ Luminescence Assay System. Briefly, the various test cancer cell lines are plated at a density of about 1×10$^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 μL of mammalian cell lysis solution is added to 100 μL of cell suspension per well of a microplate, and the plate is shaken for about five minutes in an orbital shaker at ~700 rpm. This procedure is used to lyse the cells and to stabilize the ATP. Next, 50 μL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative IC$_{50}$ of the compounds of the present invention. The following table lists the IC50 values of certain compounds of the invention in the BCL-XL dependent cell line H146, indicating that Example 4, like ABT-199, is a BCL-2 selective inhibitor.

| Example No. | H146 IC$_{50}$ (nM) |
| --- | --- |
| ABT-263 | 60.0 |
| ABT-199 | >2000 |
| 4 | >2000 |
| 12 | >2000 |

Biological Example 4: In Vivo Xenograft Studies

Typically, athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 mm$^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

What is claimed is:

1. A compound of Formula (I), or an N-oxide thereof, or a pharmaceutically acceptable salt, solvate, polymorph, tautomer, stereoisomer, an isotopic form, or a prodrug of said compound of Formula (I) or N-oxide thereof:

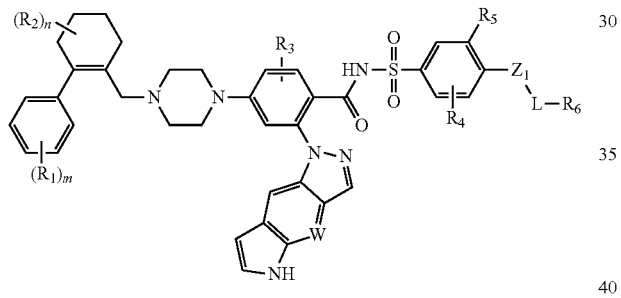

Formula (I)

wherein $Z_1$ is absent, $(CH_2)_p$, N(H), O, S, C(O), S(O)$_2$, OC(O), C(O)O, OS(O)$_2$, S(O)$_2$O, C(O)S, SC(O), C(O)C(O), C(O)N(H), N(H)C(O), S(O)$_2$N(H), N(H)S(O)$_2$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, OC(O)N(H)$(CH_2)_{p+1}$N(H)$(CH_2)_q$, a bivalent alkenyl group, or a bivalent alkynyl group;

W is CH or N, and the tricyclic

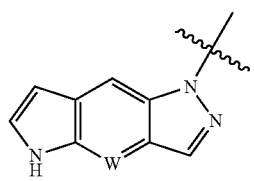

is optionally substituted with one or more $R_7$;

each of $R_1$, $R_2$, $R_3$, $R_4$, $R_5$, $R_6$, and $R_7$, independently, is H, alkyl, alkenyl, alkynyl, cycloalkyl, cycloalkenyl, heterocycloalkyl, heterocycloalkenyl, aryl, heteroaryl, halo, nitro, oxo, cyano, OR$_a$, SR$_a$, alkyl-R$_a$, NH(CH$_2$)$_p$R$_a$, C(O)R$_a$, S(O)R$_a$, SO$_2$R$_a$, C(O)OR$_a$, OC(O)R$_a$, NR$_b$R$_c$, P(O)R$_b$R$_c$, C(O)N(R$_b$)R$_c$, N(R$_b$)C(O)R$_c$, SO$_2$N(R$_b$)R$_c$, or N(R$_b$)SO$_2$R$_c$, in which said cycloalkyl, cycloalkenyl, heterocycloalkyl, heterocycloalkenyl, aryl, heteroaryl is optionally substituted with one or more R$_d$;

optionally, two of R$_2$ group, taken together with the atom to which they are attached, may optionally form a cycloalkyl or heterocycloalkyl optionally substituted with one or more R$_d$;

R$_a$, R$_b$, R$_c$ and R$_d$, independently, is H, alkyl, alkenyl, alkynyl, halo, cyano, amine, nitro, hydroxy, C(O) NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

L is absent, alkylene, alkenylene, alkynylene, cycloalkylene, cycloalkenylene, heterocycloalkylene, heterocycloalkenylene, wherein said alkylene, alkenylene, alkynylene, cycloalkylene, cycloalkenylene, heterocycloalkylene, or heterocycloalkenylene is optionally substituted with one or more R$_d$; and each of m, n, p, and q, independently, is 0, 1, 2, 3, or 4.

2. The compound according to claim 1 or an N-oxide thereof, or a pharmaceutically acceptable salt, solvate, polymorph, tautomer, stereoisomer, an isotopic form, or a prodrug thereof, wherein the compound is represented by Formula (II)

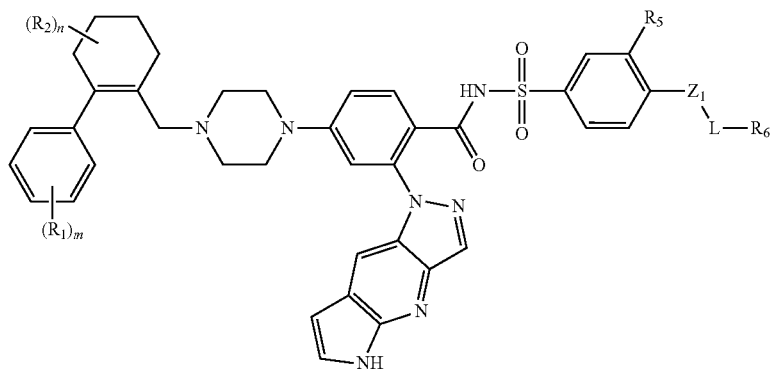

Formula (II)

wherein the tricyclic

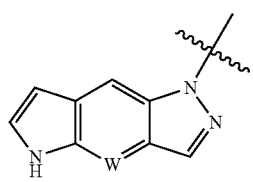

is unsubstituted.

3. The compound according to claim 2 or an N-oxide thereof, or a pharmaceutically acceptable salt, solvate, polymorph, tautomer, stereoisomer, an isotopic form, or a prodrug thereof, wherein the compound is represented by Formula (III)

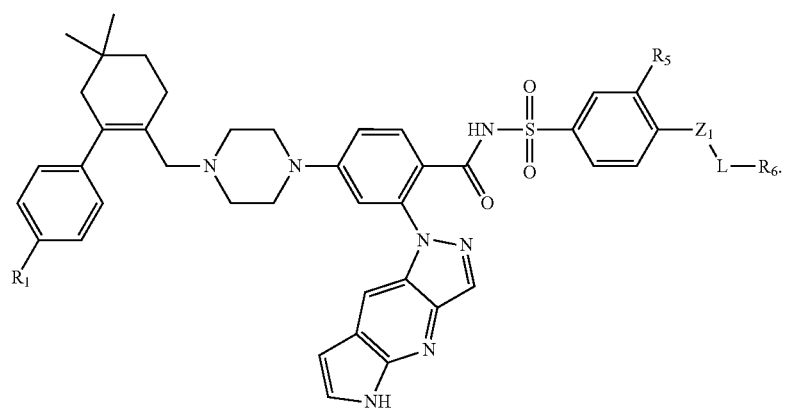

Formula (III)

4. The compound according to claim 3 or an N-oxide thereof, or a pharmaceutically acceptable salt, solvate, polymorph, tautomer, stereoisomer, an isotopic form, or a prodrug thereof, wherein $R_1$ is Cl.

5. The compound according to claim 4 or an N-oxide thereof, or a pharmaceutically acceptable salt, solvate, polymorph, tautomer, stereoisomer, an isotopic form, or a prodrug thereof, wherein $R_5$ independently, is nitro, halo, or $SO_2R_a$.

6. The compound according to claim 5 or an N-oxide thereof, or a pharmaceutically acceptable salt, solvate, polymorph, tautomer, stereoisomer, an isotopic form, or a prodrug thereof, wherein $Z_1$ is absent, NH, O, or S.

7. The compound according to claim 6 or an N-oxide thereof, or a pharmaceutically acceptable salt, solvate, polymorph, tautomer, stereoisomer, an isotopic form, or a prodrug thereof, wherein L is absent or $C_{1-3}$alkylene.

8. The compound according to claim 7 or an N-oxide thereof, or a pharmaceutically acceptable salt, solvate, polymorph, tautomer, stereoisomer, an isotopic form, or a prodrug thereof, wherein $R_6$ is H, 4-6 membered cycloalkyl or 4-6 membered heterocyclyl, wherein the 4-6 membered cycloalkyl or 4-6 membered heterocyclyl is optionally substituted with one or more substituents selected from the group consisting of halo, $C_{1-4}$ alkyl, CN, —OH, $C_{1-4}$ alkoxy, —S(O)$_2$CH$_3$, —COCH$_3$, 3-6 membered cycloalkyl, and 3-6 membered heterocyclyl.

9. The compound according to claim 1 or an N-oxide thereof, or a pharmaceutically acceptable salt, solvate, polymorph, tautomer, stereoisomer, an isotopic form, or a prodrug thereof, wherein the compound is

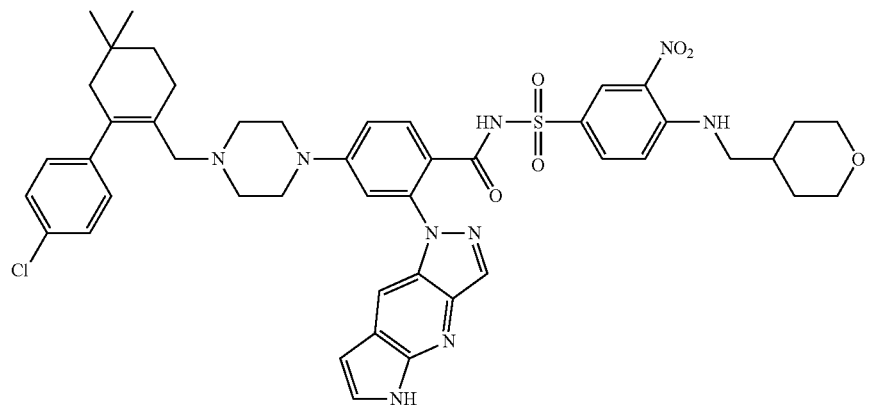
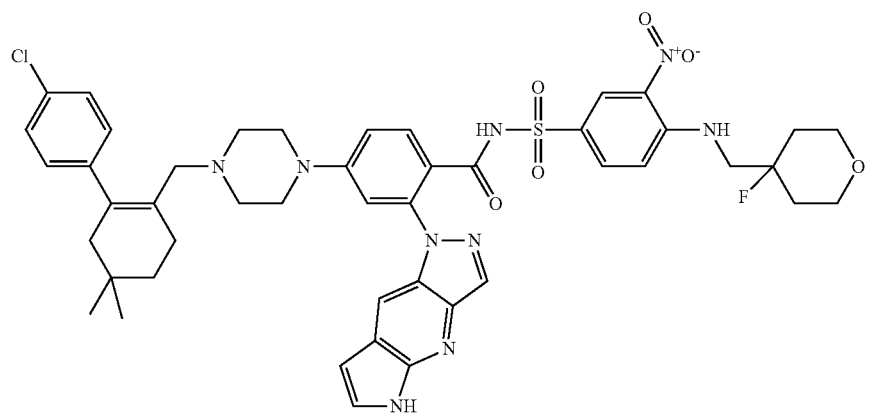
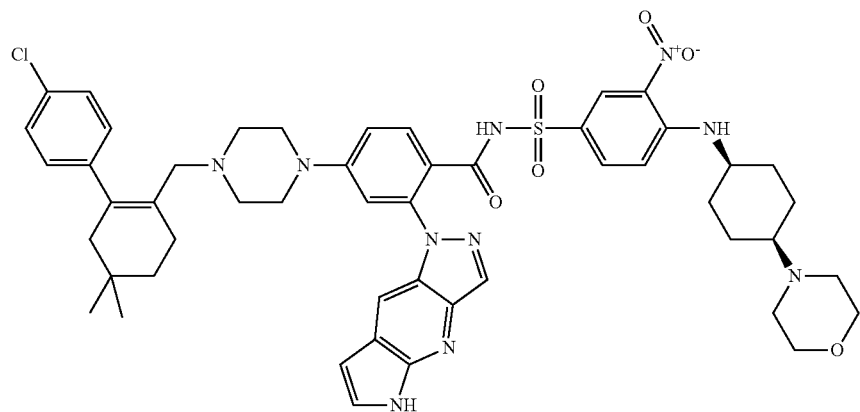
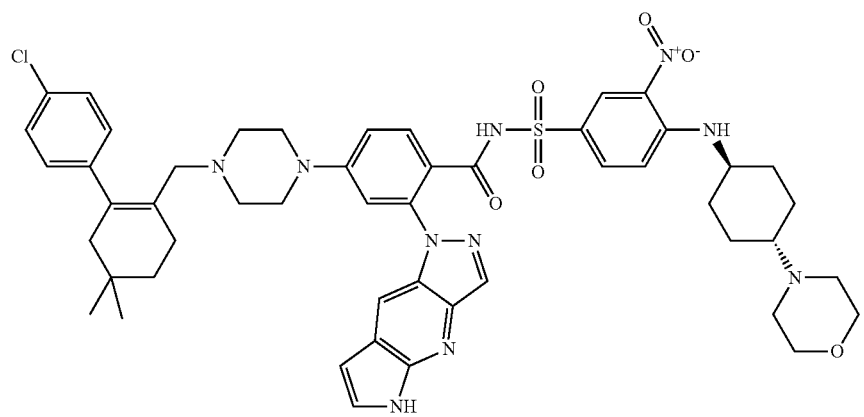

-continued
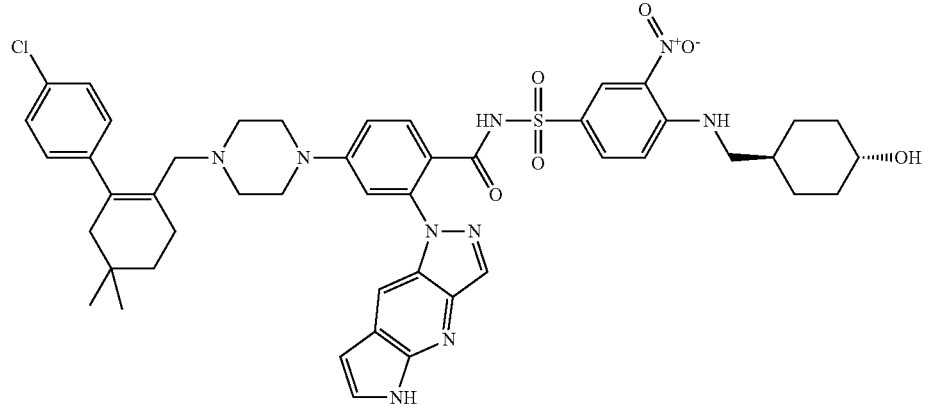
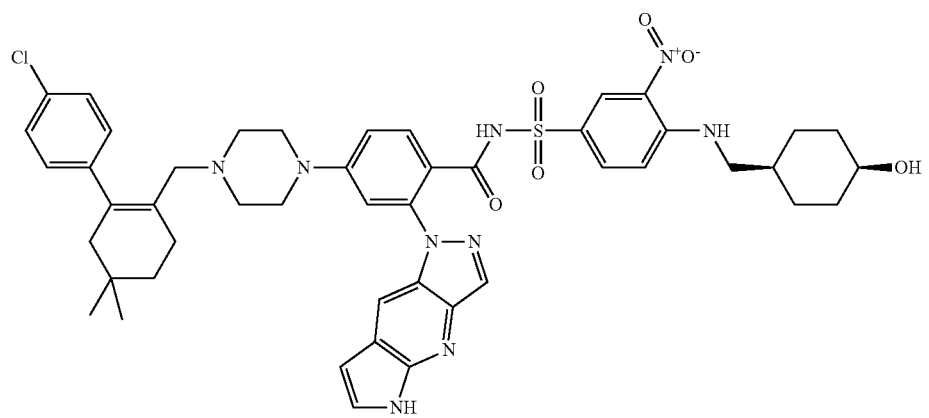
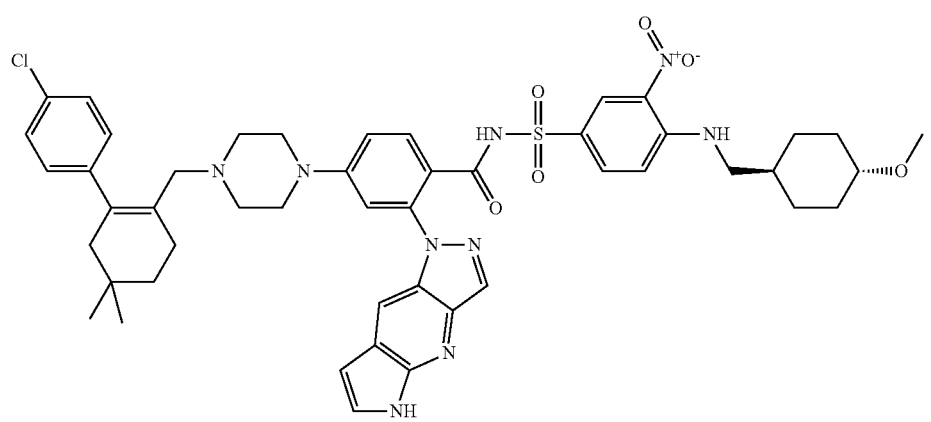
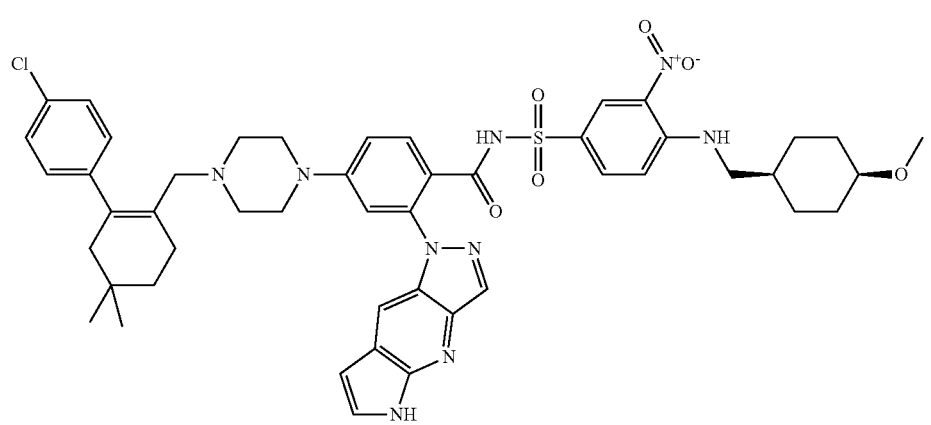

-continued
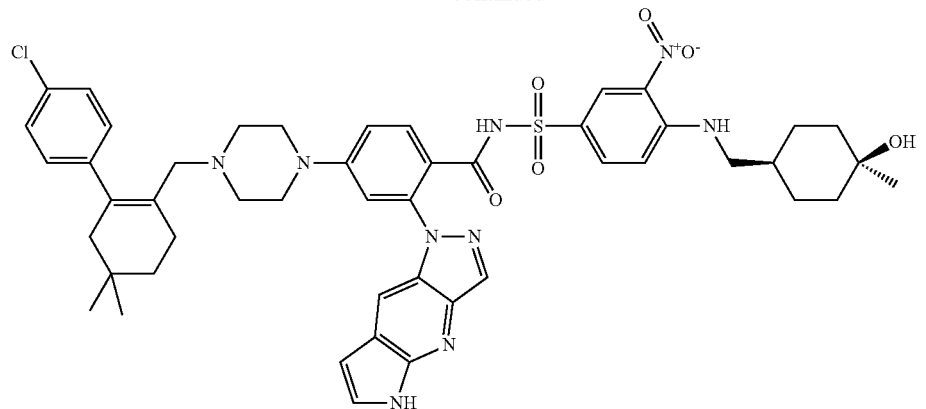
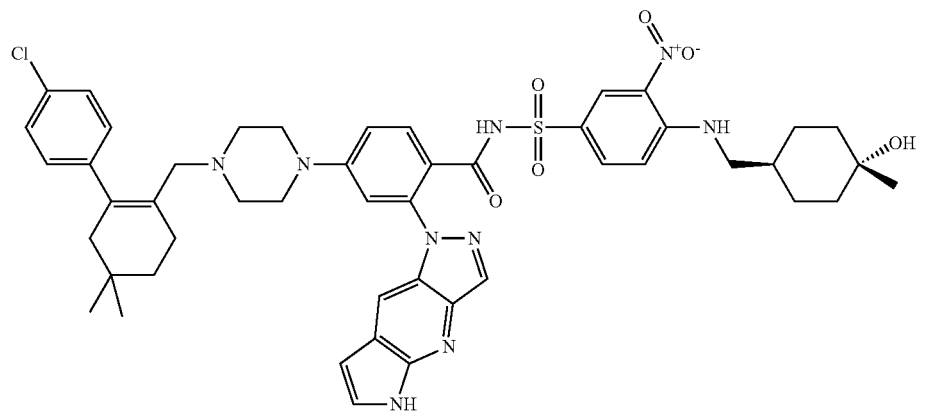
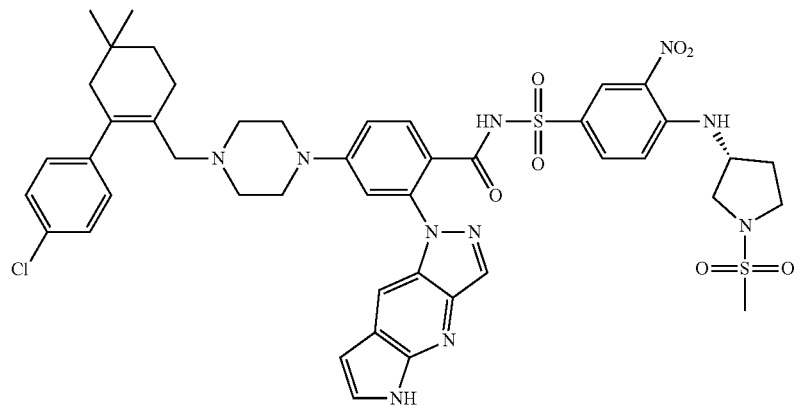
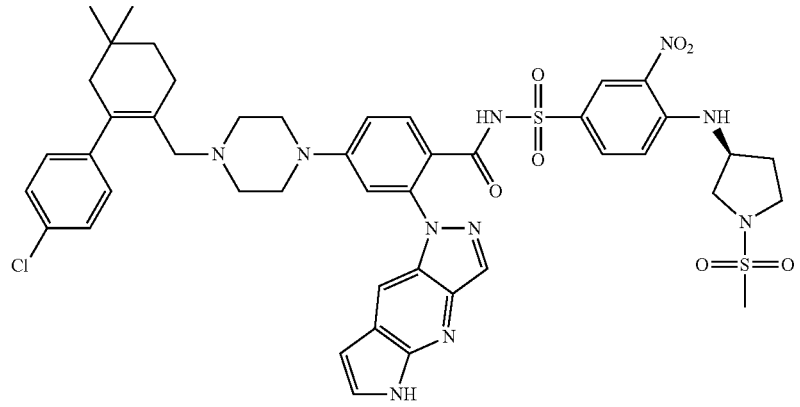

-continued
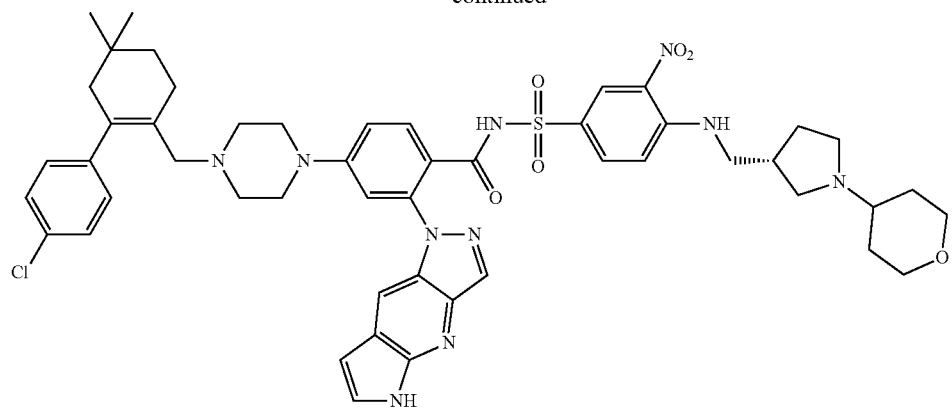
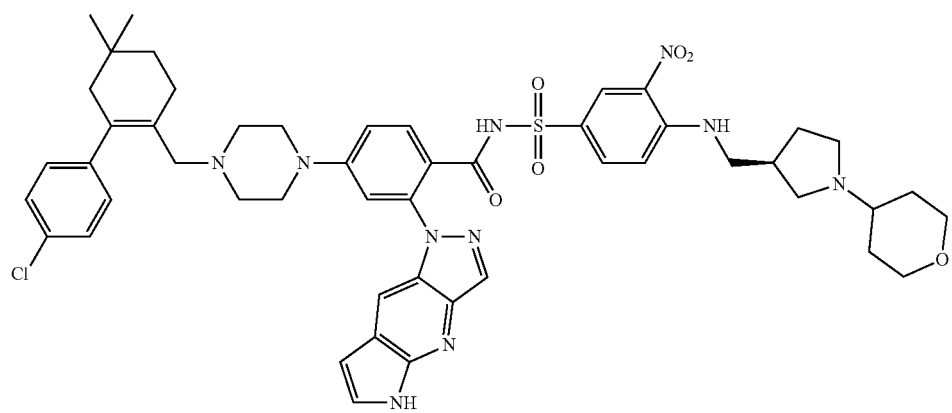
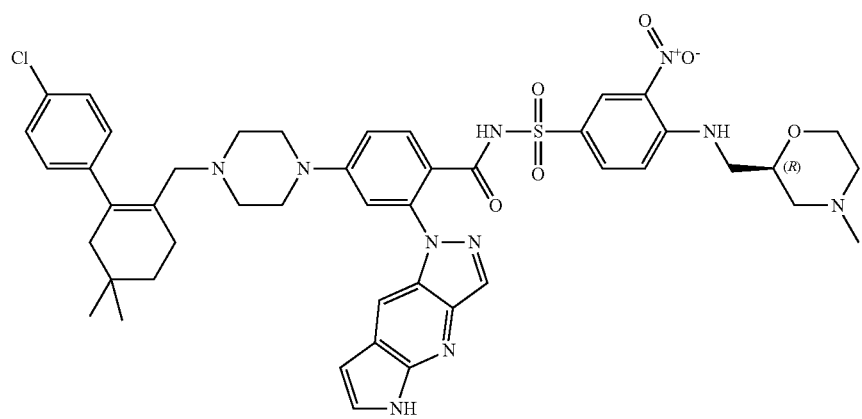
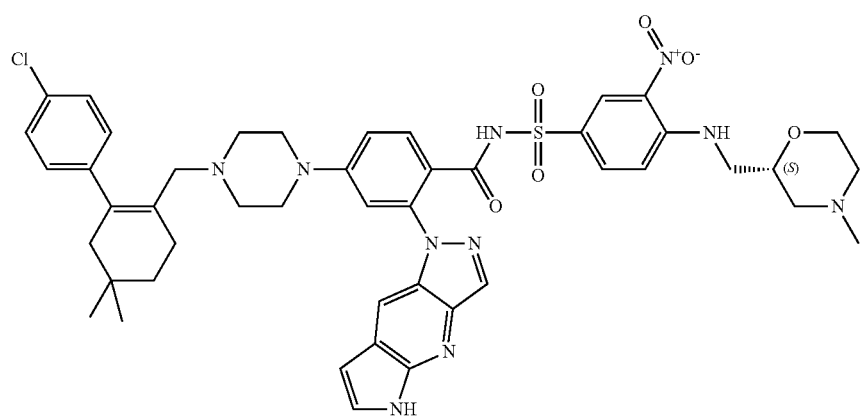

-continued
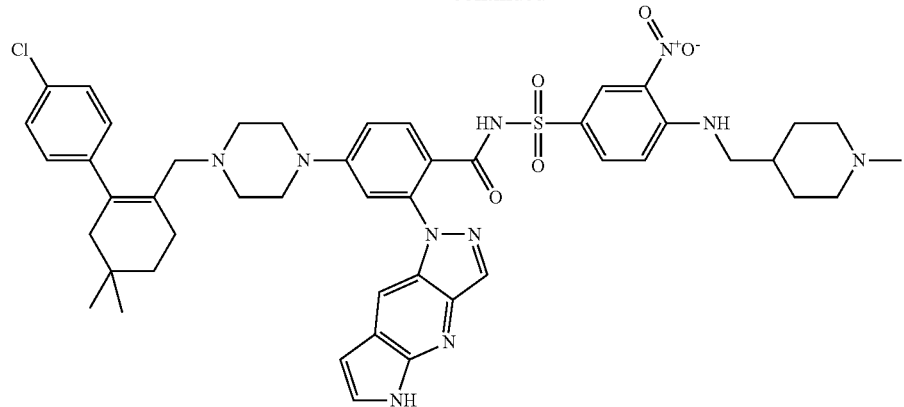
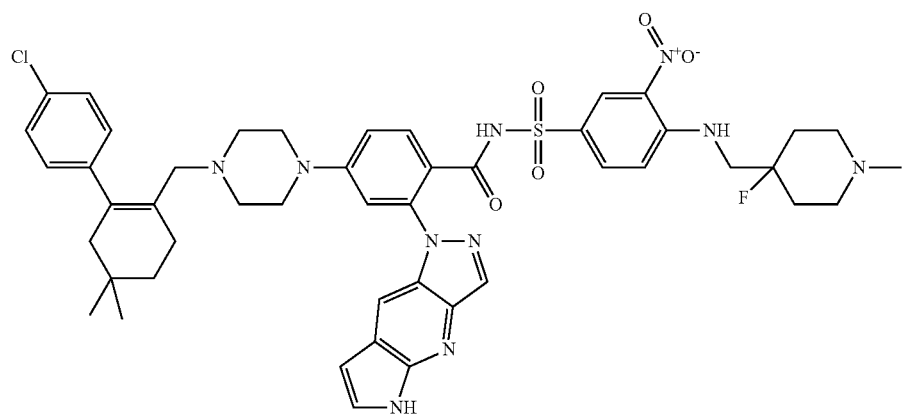
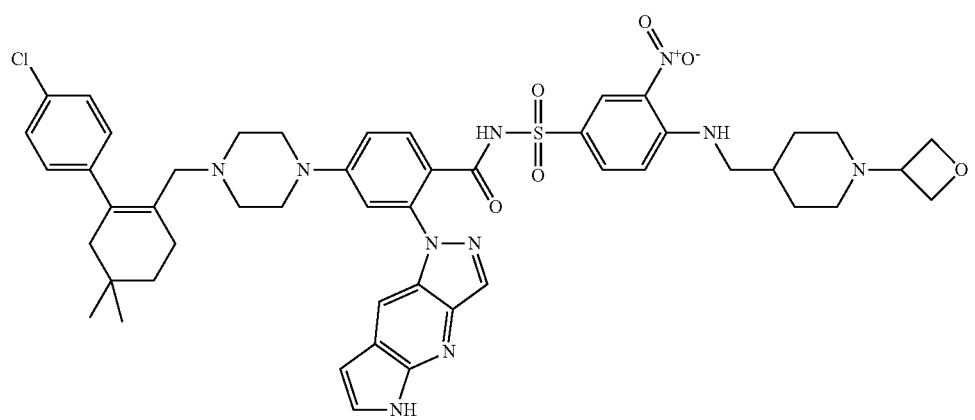
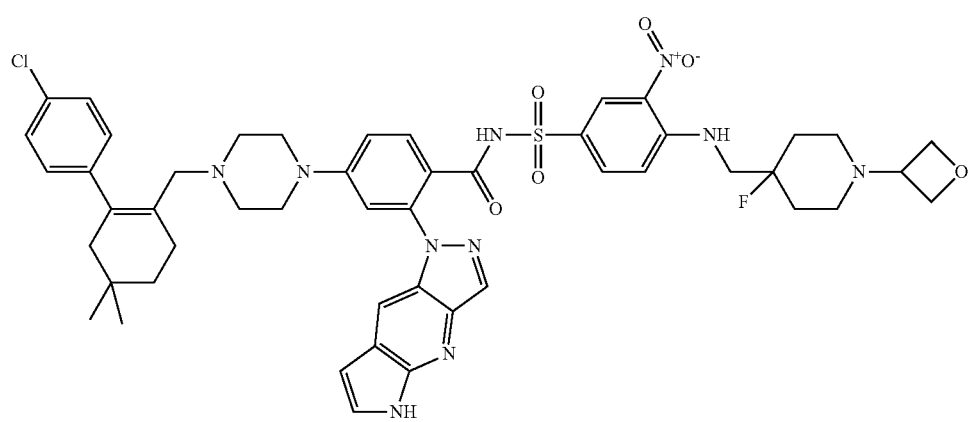

-continued
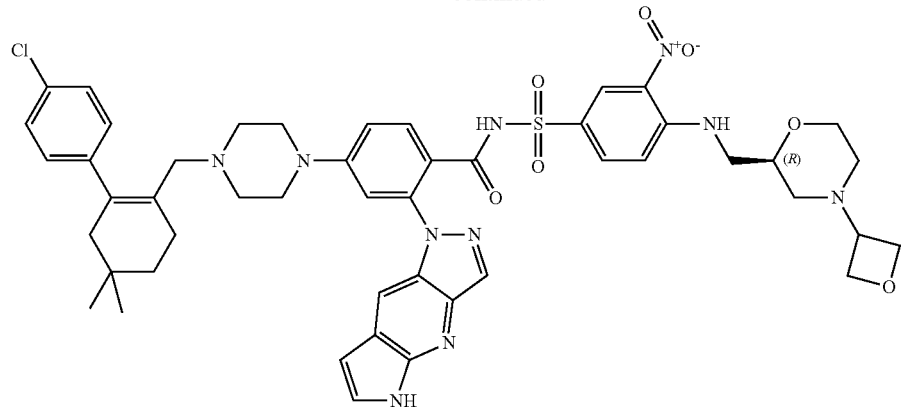
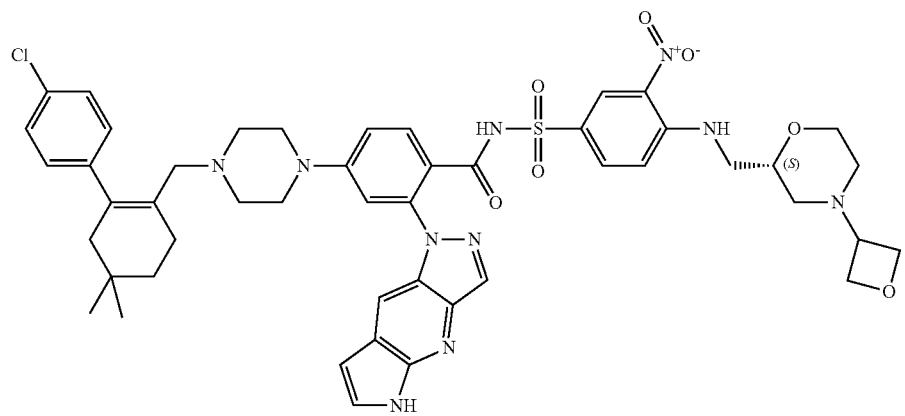
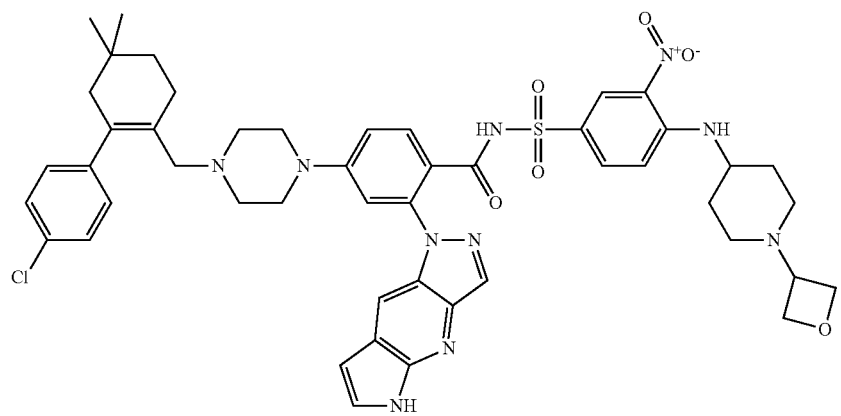
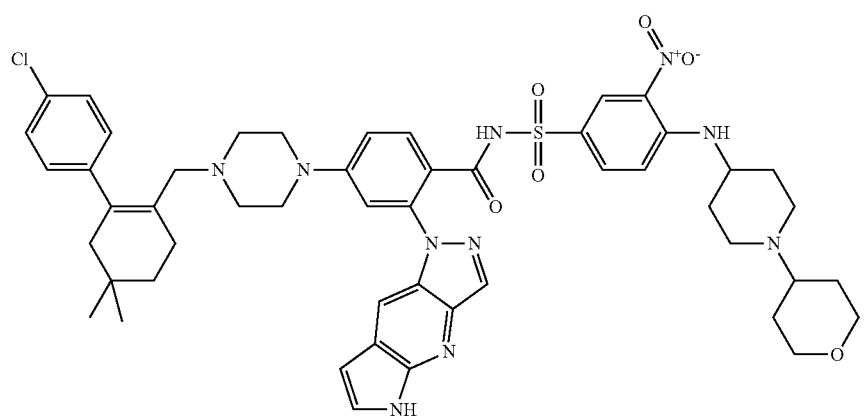

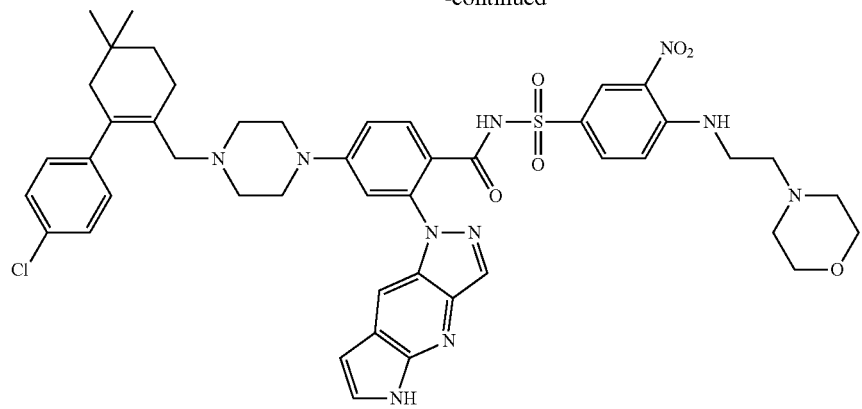
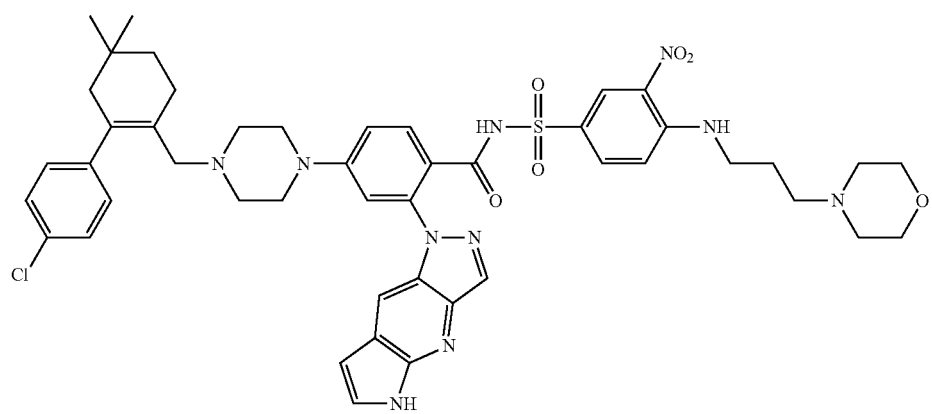
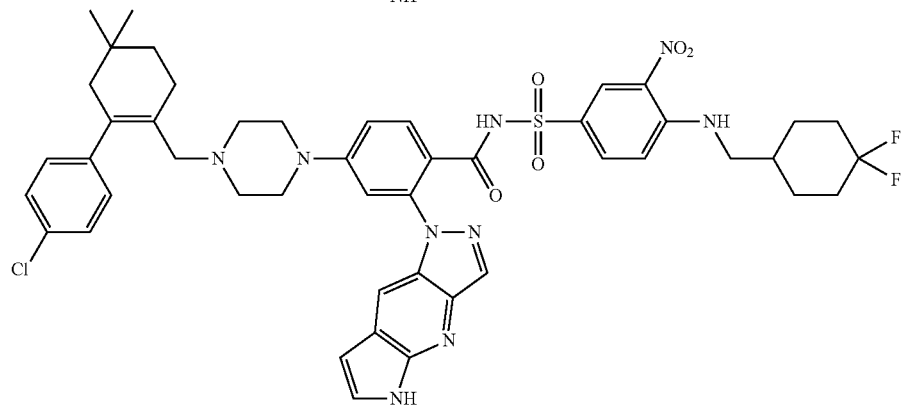
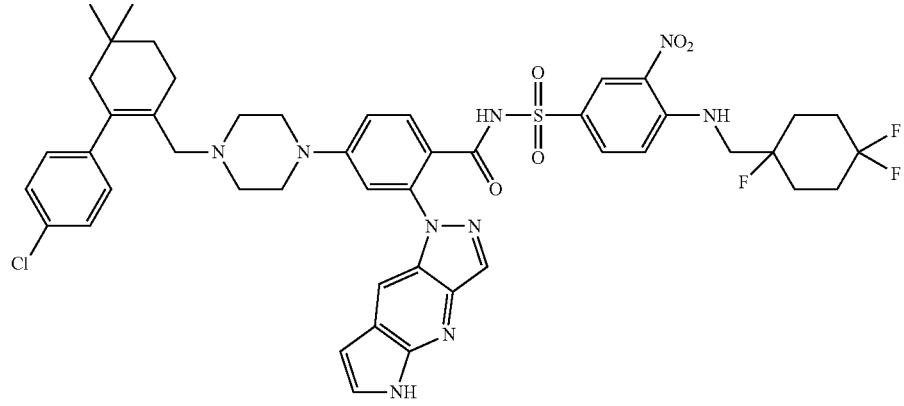
10. The compound according to claim 1 or an N-oxide thereof, or a pharmaceutically acceptable salt, solvate, polymorph, tautomer, stereoisomer, an isotopic form, or a prodrug thereof, wherein the compound is

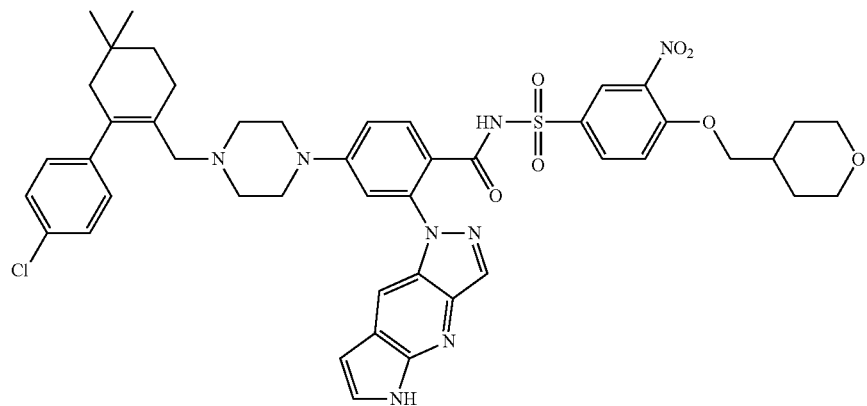
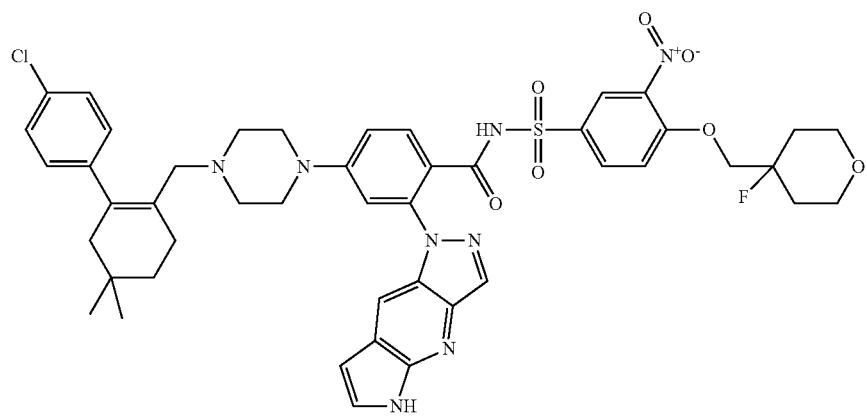
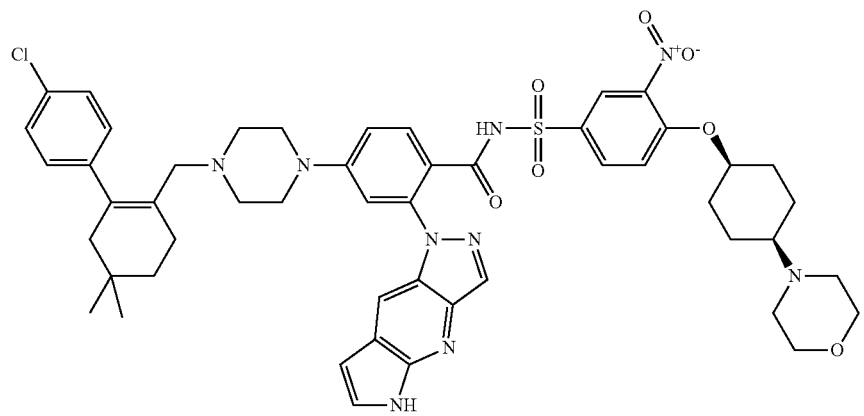
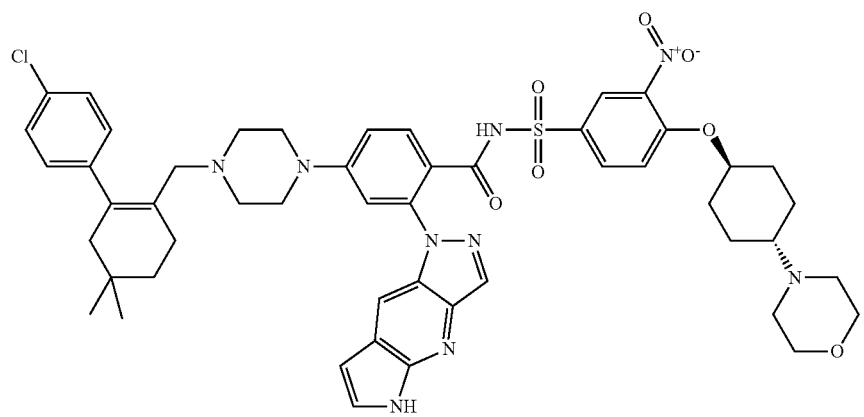

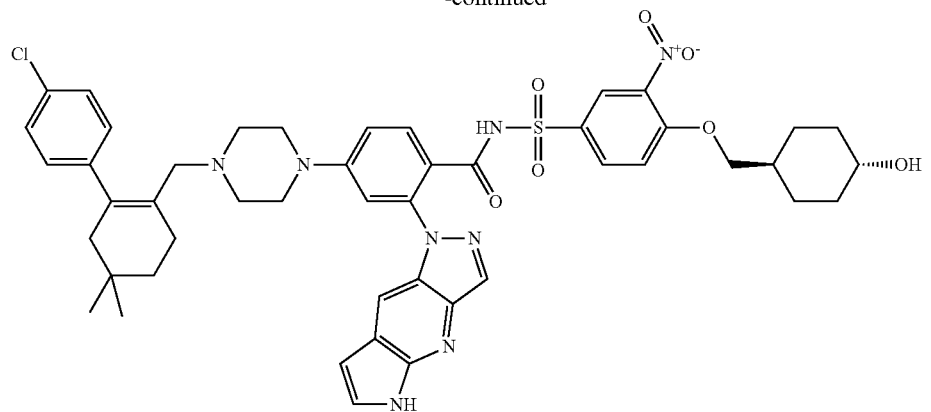
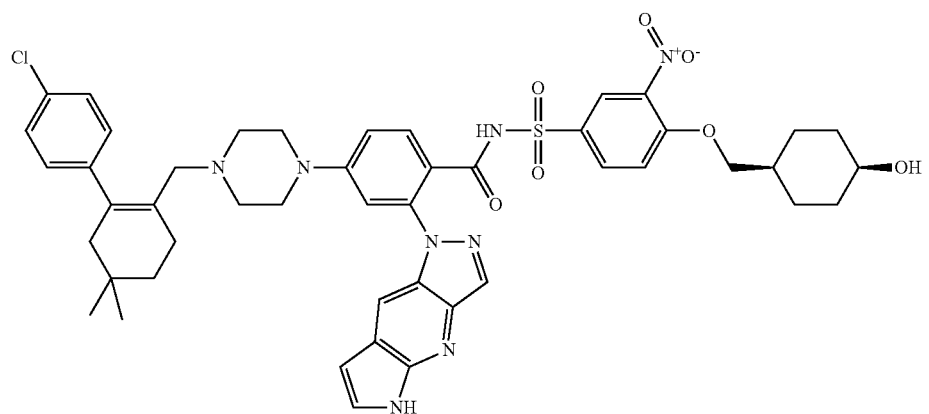
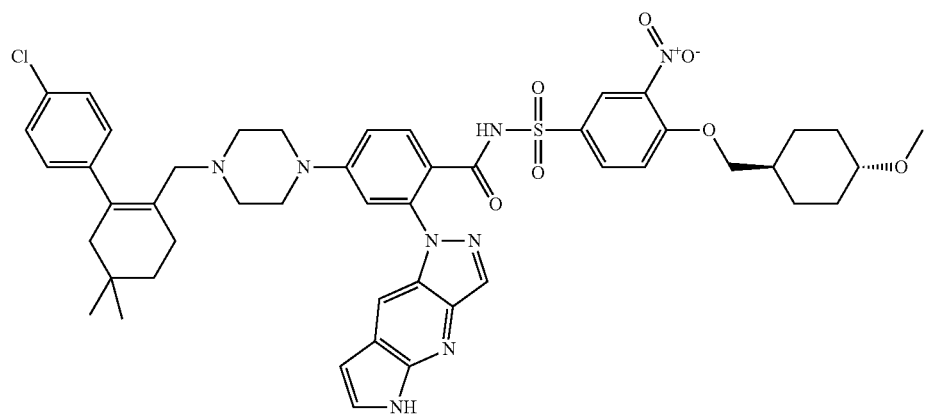
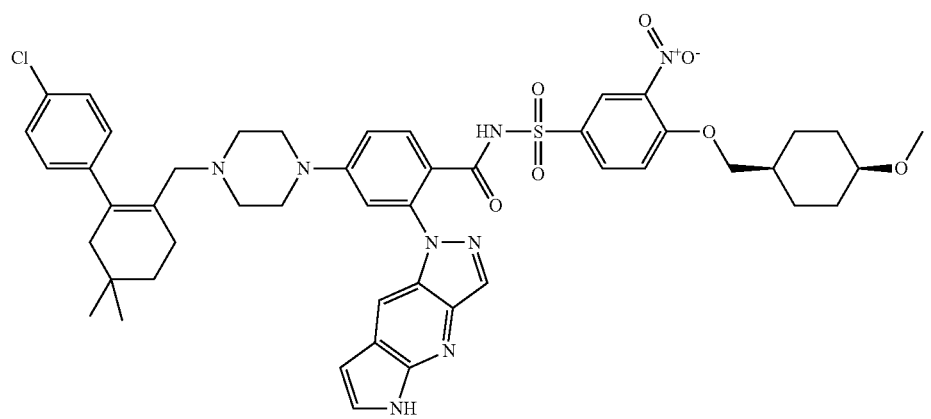

-continued
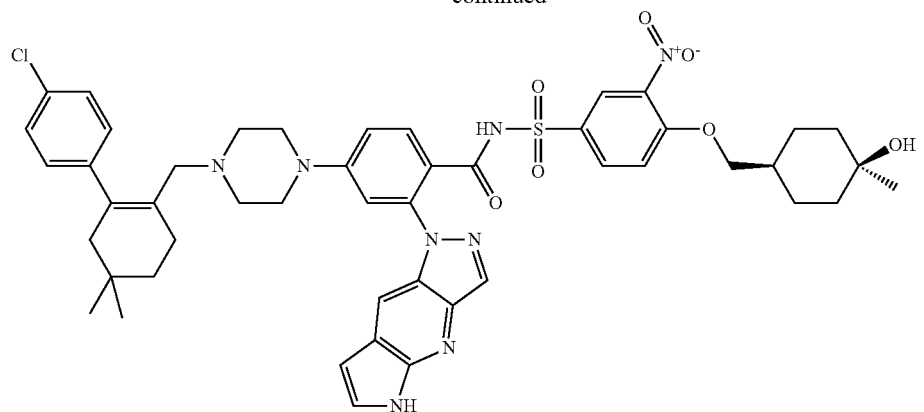
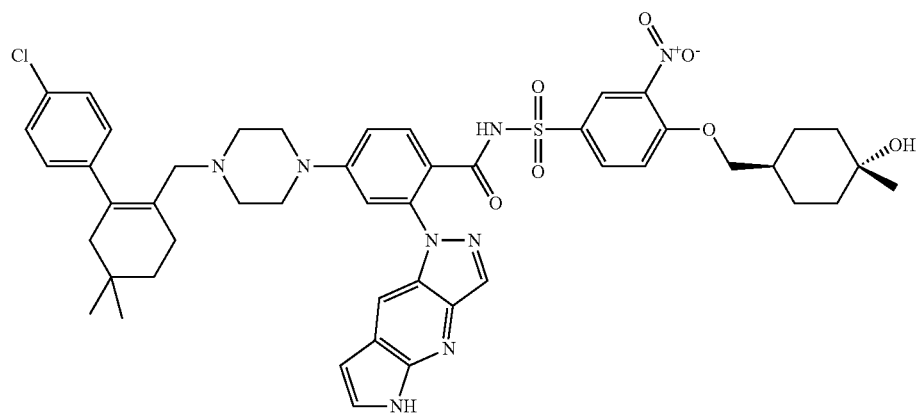
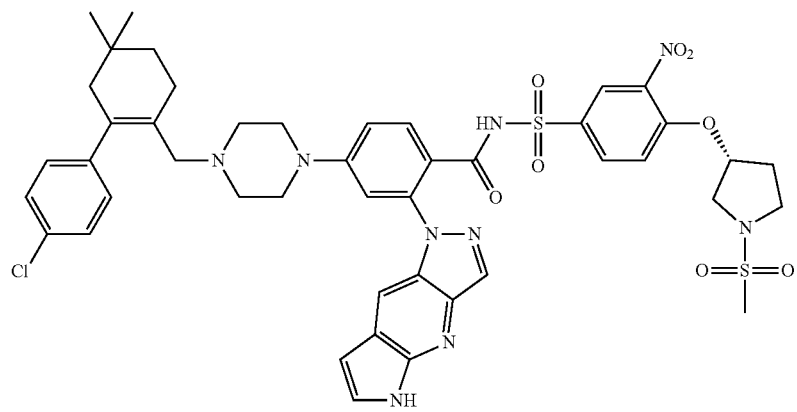
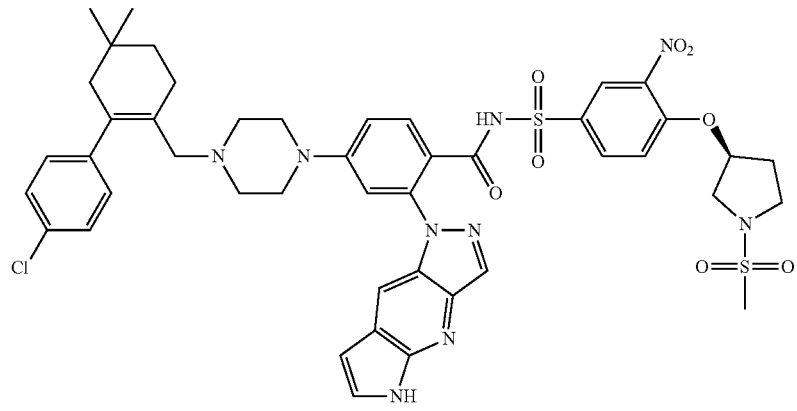

-continued
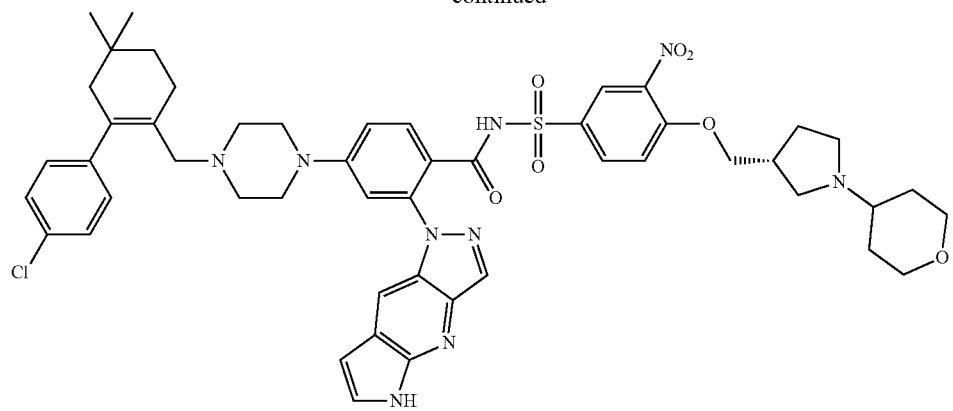
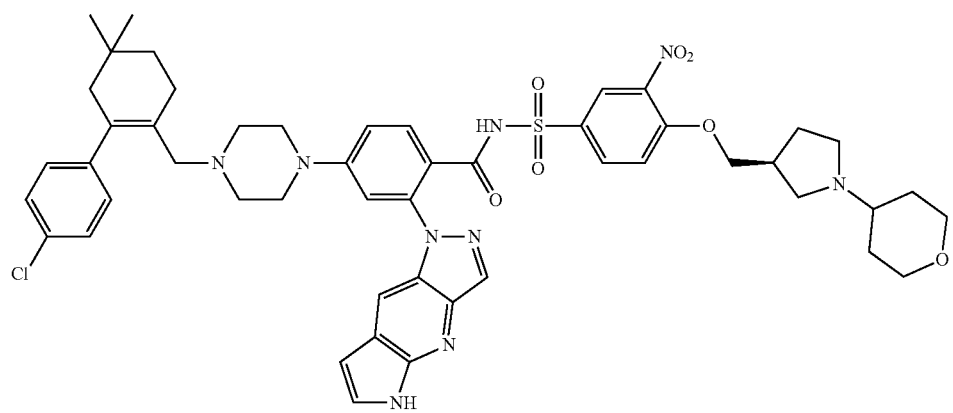
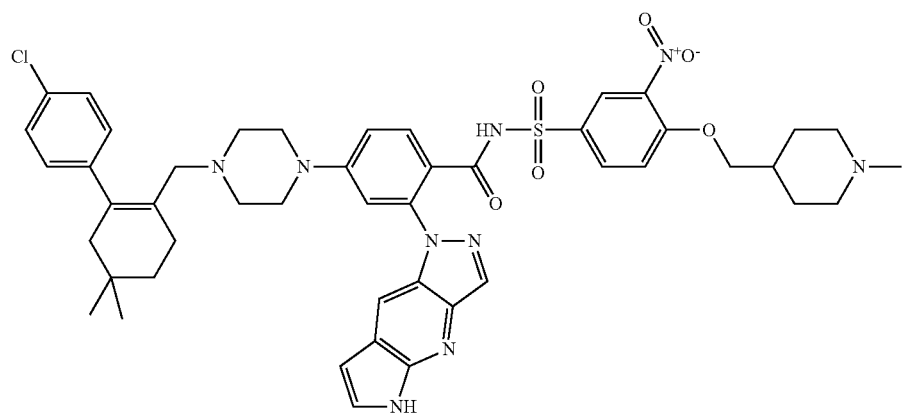
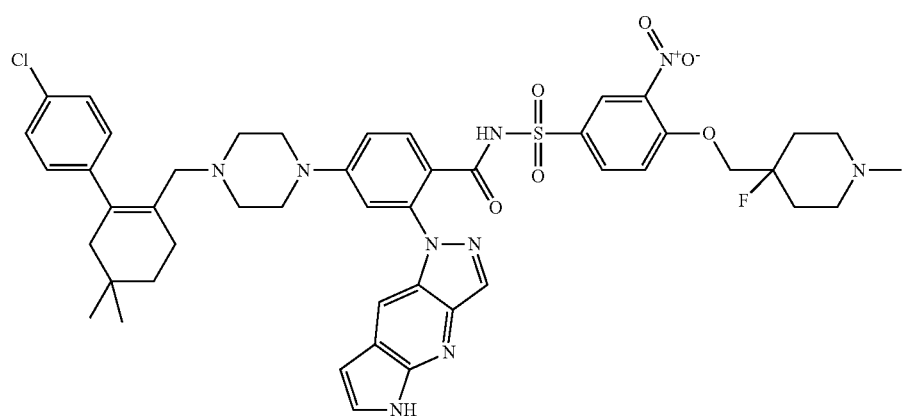

-continued
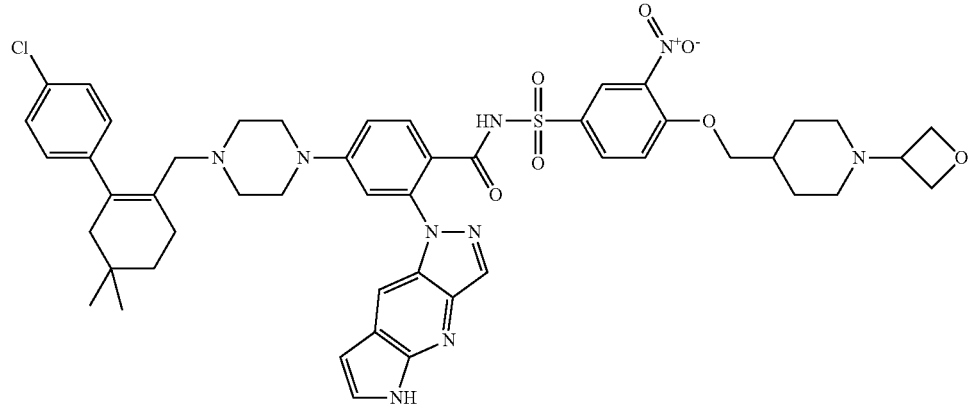
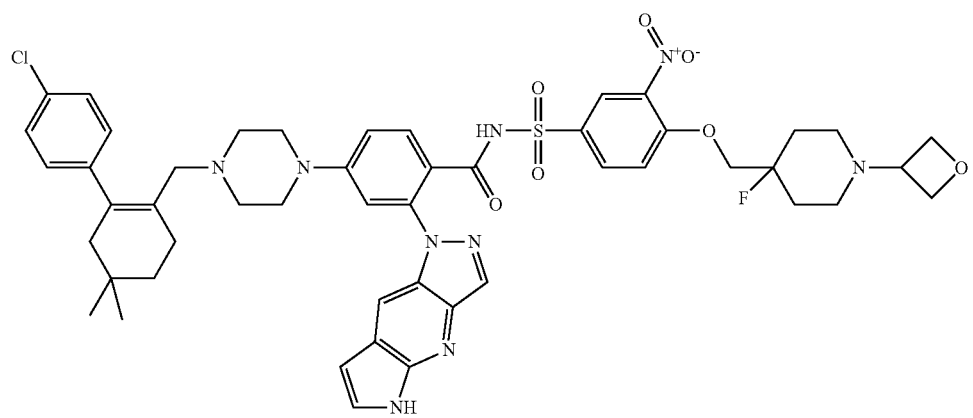
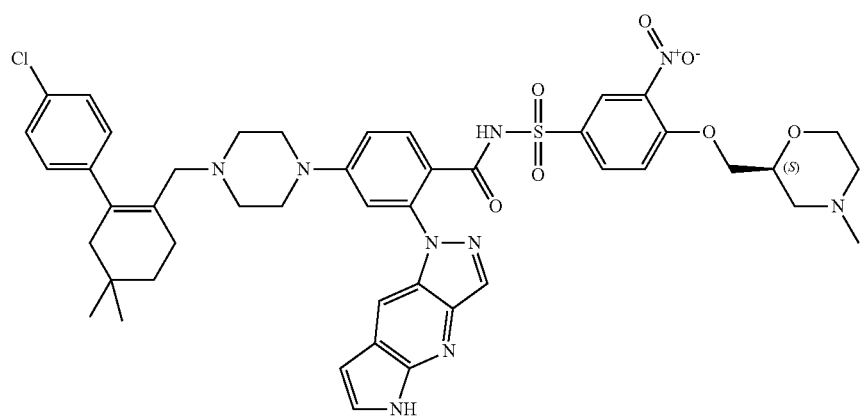
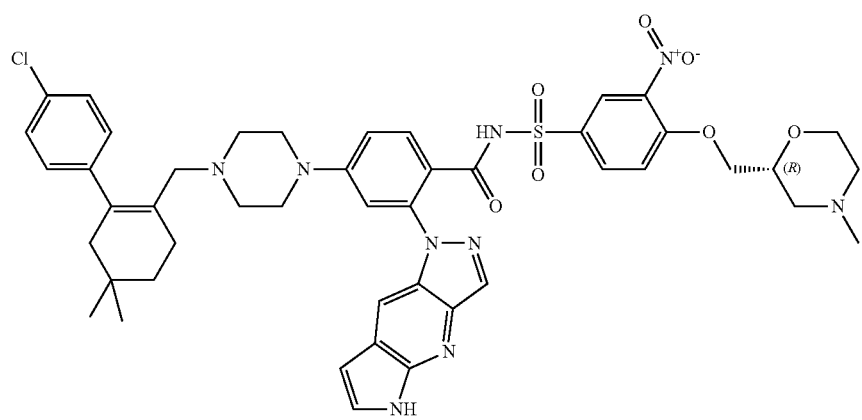

-continued
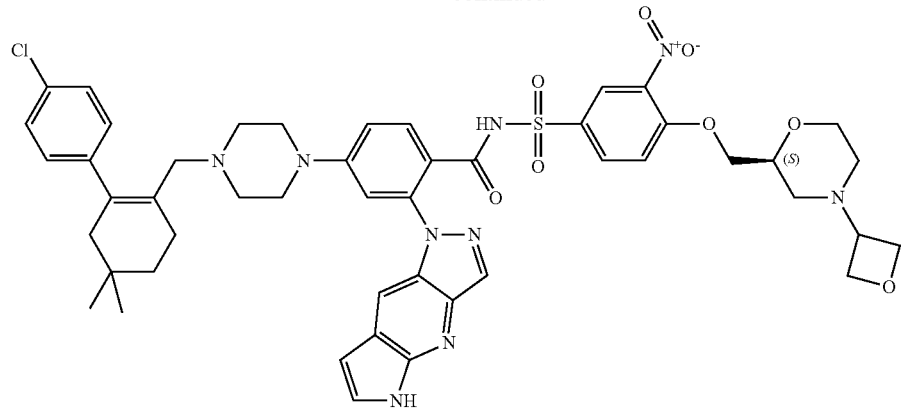
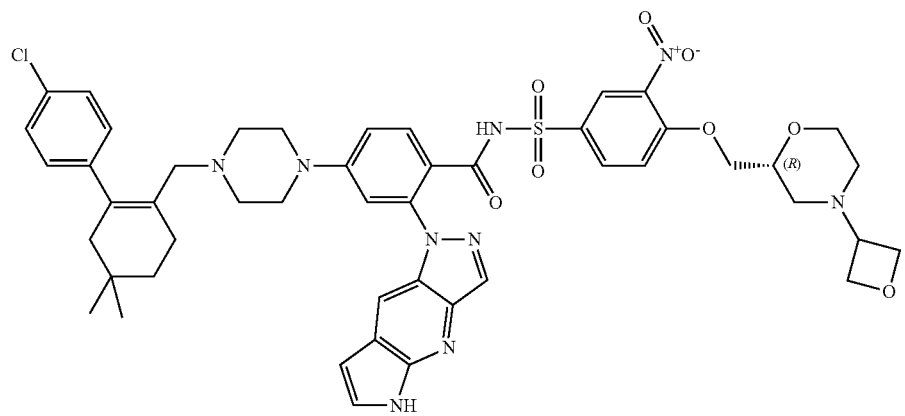
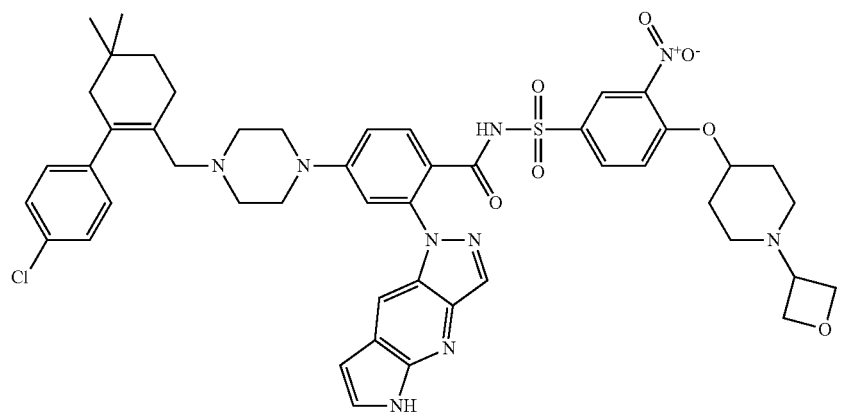
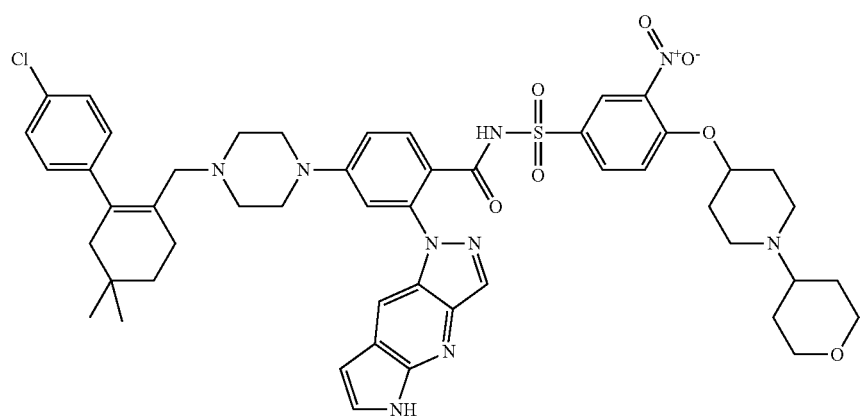

-continued
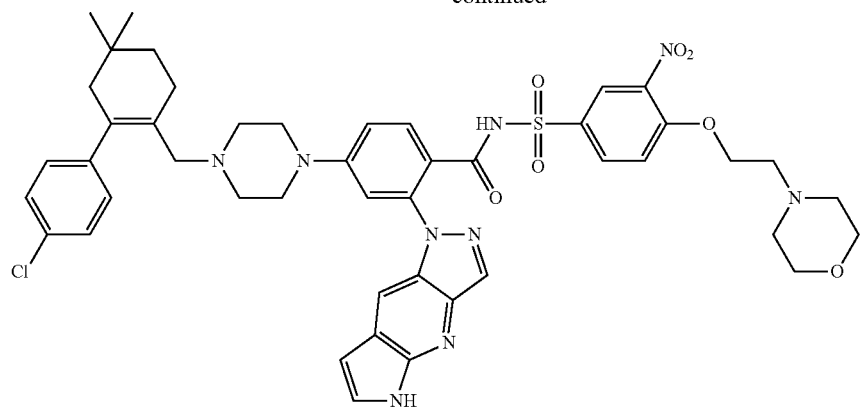
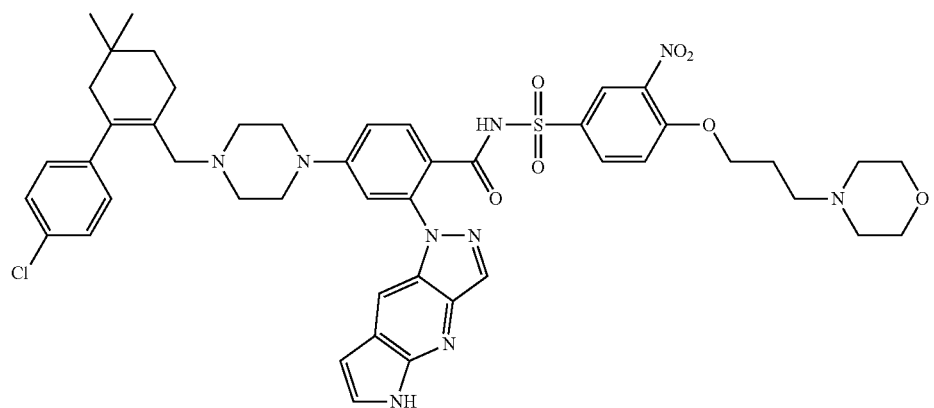
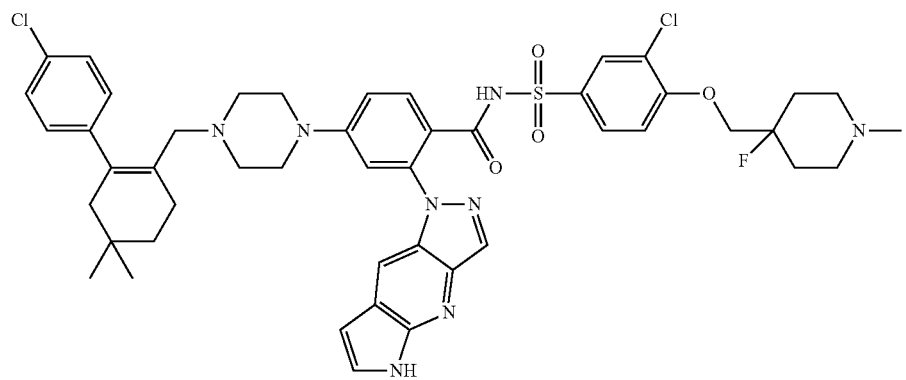
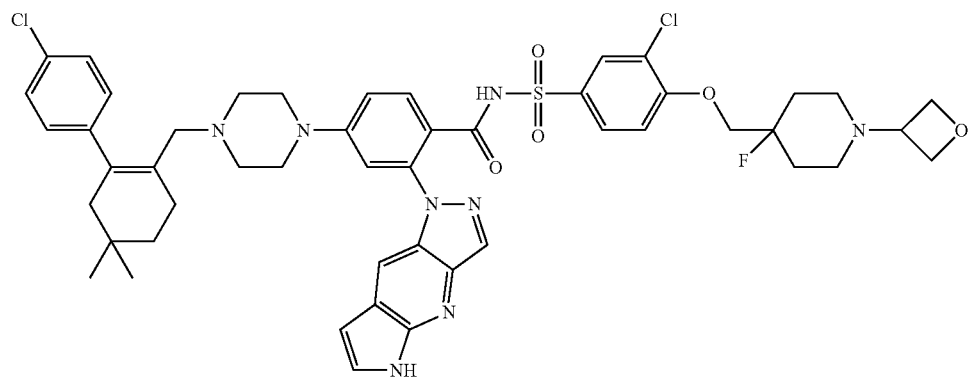

-continued

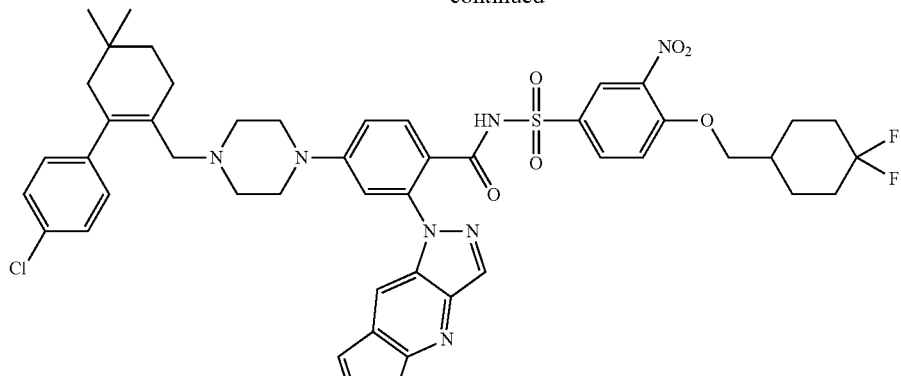

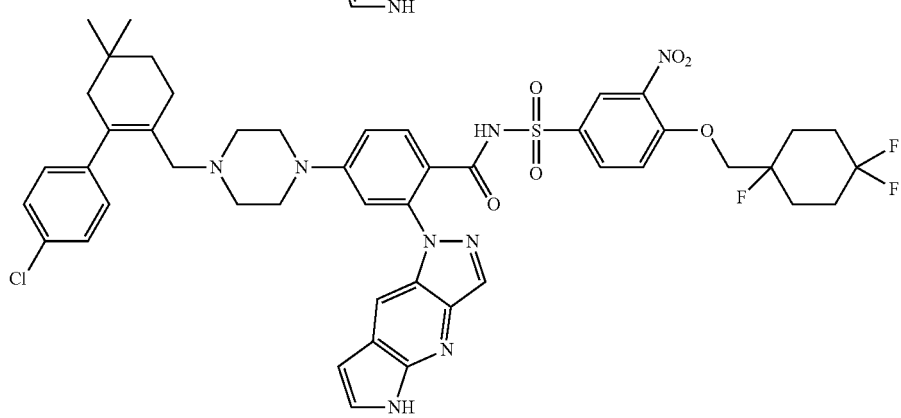

11. A pharmaceutical composition comprising a compound of Formula (I) or an N-oxide thereof as defined in claim 1, or a pharmaceutically acceptable salt, solvate, polymorph, tautomer, stereoisomer, an isotopic form, or a prodrug of said compound of Formula (I) or an N-oxide thereof, and a pharmaceutically acceptable diluent or carrier.

12. A method of treating a neoplastic disease or autoimmune disease which can be ameliorated by inhibition of bcl-2, comprising administering to a subject having such a disease an effective amount of a compound of Formula (I) or an N-oxide thereof as defined in claim 1, or a pharmaceutically acceptable salt, solvate, polymorph, tautomer, stereoisomer, an isotopic form, or a prodrug of said compound of Formula (I) or an N-oxide thereof.

13. The method according to claim 12, wherein the neoplastic disease is leukemia, lymphoma, or multiple myeloma.

* * * * *

UNITED STATES PATENT AND TRADEMARK OFFICE
CERTIFICATE OF CORRECTION

PATENT NO. : 10,377,755 B2  
APPLICATION NO. : 16/045736  
DATED : August 13, 2019  
INVENTOR(S) : Yi Chen et al.

Page 1 of 1

It is certified that error appears in the above-identified patent and that said Letters Patent is hereby corrected as shown below:

In the Claims

In Claim 2, Column 155, Line numbers 20-30, please replace the tricyclic structure:

" 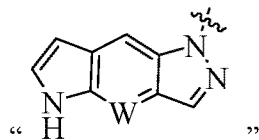 "

With the following structure:

-- 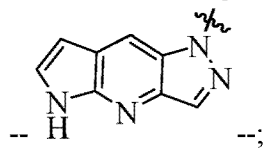 --;

In Claim 9, Column 170, Line number 64, please add a "." to the end of Claim 9; and In Claim 10, Column 179, Line number 34, please add a "." to the end of Claim 10.

Signed and Sealed this  
Twenty-fourth Day of September, 2019

Andrei Iancu  
*Director of the United States Patent and Trademark Office*